(12) United States Patent
Archibald et al.

(10) Patent No.: US 11,075,019 B2
(45) Date of Patent: Jul. 27, 2021

(54) SYSTEM FOR RADIOPHARMACEUTICAL PRODUCTION

(71) Applicant: The University of Hull, Hull (GB)

(72) Inventors: Stephen James Archibald, Hull (GB); Ping He, Hull (GB); Nathan Joel Brown, Hull (GB); Mark Duncan Tarn, Hull (GB); Stephen John Haswell, Hull (GB); Mohammad Mehdi Nasr Esfahani, Hull (GB); Nicole Pamme, Hull (GB); Richard Alexander, Hull (GB)

(73) Assignee: The University of Hull, Hull Humberside (GB)

( * ) Notice: Subject to any disclaimer, the term of this patent is extended or adjusted under 35 U.S.C. 154(b) by 0 days.

(21) Appl. No.: 15/521,205

(22) PCT Filed: Oct. 22, 2015

(86) PCT No.: PCT/GB2015/053173
§ 371 (c)(1),
(2) Date: Apr. 21, 2017

(87) PCT Pub. No.: WO2016/063072
PCT Pub. Date: Apr. 28, 2016

(65) Prior Publication Data
US 2018/0033510 A1    Feb. 1, 2018

(30) Foreign Application Priority Data
Oct. 23, 2014    (GB) ...................................... 1418899

(51) Int. Cl.
*B01J 19/00* (2006.01)
*C07B 59/00* (2006.01)
(Continued)

(52) U.S. Cl.
CPC ....... *G21G 1/0005* (2013.01); *A61K 51/0491* (2013.01); *B01J 19/0093* (2013.01);
(Continued)

(58) Field of Classification Search
None
See application file for complete search history.

(56) References Cited

U.S. PATENT DOCUMENTS 5,757,482 A * 5/1998 Fuchs .................... G01N 21/05
356/246
5,770,030 A    6/1998 Hamacher et al.
(Continued)

FOREIGN PATENT DOCUMENTS

CN    101035602 A    9/2007
CN    101146609 B    3/2008
(Continued)

OTHER PUBLICATIONS

Unqer et al., Chapter 3: Column Technology in Liquid Chromatography, *Liquid Chromatography: Fundamentals and Instrumentation*, pp. 41-86, Elsevier Inc. (Year: 2013).*
(Continued)

*Primary Examiner* — Jennifer A Leung
(74) *Attorney, Agent, or Firm* — Sheridan Ross P.C.

(57) ABSTRACT

Certain embodiments of the present invention relate to a system and a method for producing a radiopharmaceutical, wherein the system is formed from and/or provides a microfluidic flow system. In certain embodiments, the system comprises a radioisotope isolation module, a radiopharmaceutical production module, a purification module and a quality control module.

31 Claims, 16 Drawing Sheets

(51) Int. Cl.
*G21G 1/00* (2006.01)
*A61K 51/04* (2006.01)
*B01J 20/283* (2006.01)
*B01J 39/26* (2006.01)
*G01N 30/74* (2006.01)
*G01N 33/60* (2006.01)
*G01N 30/00* (2006.01)

(52) U.S. Cl.
CPC ............ *B01J 20/283* (2013.01); *B01J 39/26* (2013.01); *C07B 59/00* (2013.01); *G01N 30/74* (2013.01); *G01N 33/60* (2013.01); *B01J 2219/0081* (2013.01); *B01J 2219/0086* (2013.01); *B01J 2219/0097* (2013.01); *B01J 2219/00853* (2013.01); *B01J 2219/00862* (2013.01); *B01J 2219/00871* (2013.01); *B01J 2219/00916* (2013.01); *G01N 2030/77* (2013.01)

(56) References Cited

U.S. PATENT DOCUMENTS

| | | | |
|---|---|---|---|
| 6,030,552 | A | 2/2000 | Ambros et al. |
| 6,207,098 | B1 | 3/2001 | Nakanishi et al. |
| 6,827,095 | B2* | 12/2004 | O'Connor ............... B01F 5/064 137/15.01 |
| 7,670,559 | B2* | 3/2010 | Chien ............... B01L 3/502715 422/504 |
| 8,077,311 | B1 | 12/2011 | Byrne et al. |
| 2004/0174657 | A1 | 9/2004 | Andelman et al. |
| 2005/0226776 | A1* | 10/2005 | Brady ............... B01J 19/0093 422/400 |
| 2005/0232387 | A1* | 10/2005 | Padgett ............... A61K 51/0491 376/194 |
| 2005/0232861 | A1 | 10/2005 | Buchanan et al. |
| 2006/0160209 | A1 | 7/2006 | Larson et al. |
| 2006/0228812 | A1 | 10/2006 | Higashino et al. |
| 2007/0138076 | A1 | 6/2007 | Daridon et al. |
| 2007/0166199 | A1 | 7/2007 | Zhou et al. |
| 2008/0064110 | A1 | 3/2008 | Elizarov et al. |
| 2008/0093300 | A1 | 4/2008 | Clarke et al. |
| 2008/0153155 | A1 | 6/2008 | Kato et al. |
| 2008/0224072 | A1 | 9/2008 | Sonnenhol et al. |
| 2009/0036668 | A1 | 2/2009 | Elizarov et al. |
| 2009/0079409 | A1 | 3/2009 | Chang |
| 2009/0095635 | A1 | 4/2009 | Elizarov et al. |
| 2010/0069600 | A1 | 3/2010 | Morelle et al. |
| 2010/0101943 | A1 | 4/2010 | Iwata et al. |
| 2011/0070160 | A1 | 3/2011 | Nutt et al. |
| 2011/0100840 | A1 | 5/2011 | Nakanishi et al. |
| 2011/0150714 | A1 | 6/2011 | Elizarov et al. |
| 2012/0142118 | A1 | 6/2012 | Brenna et al. |
| 2012/0301372 | A1 | 11/2012 | Watanabe et al. |
| 2013/0248366 | A1 | 9/2013 | Haswell et al. |
| 2013/0337493 | A1* | 12/2013 | Hansteen ............... G01N 21/31 435/34 |
| 2014/0030800 | A1 | 1/2014 | Moses et al. |
| 2014/0316130 | A1 | 10/2014 | Brady et al. |
| 2015/0152206 | A1* | 6/2015 | Keng ............... B01J 20/3204 522/185 |
| 2017/0368534 | A1 | 12/2017 | Archibald et al. |
| 2018/0025801 | A1 | 1/2018 | Archibald et al. |
| 2018/0033510 | A1 | 2/2018 | Archibald et al. |

FOREIGN PATENT DOCUMENTS

| | | |
|---|---|---|
| CN | 102245305 B | 11/2011 |
| CN | 104039166 A | 9/2014 |
| EP | 1933330 A1 | 6/2008 |
| WO | 2003078358 A2 | 9/2003 |
| WO | 2004093652 A2 | 11/2004 |
| WO | 2006071470 A2 | 7/2006 |
| WO | WO 2007/122819 | 11/2007 |
| WO | 2008001098 A1 | 1/2008 |
| WO | 2008091694 A9 | 11/2008 |
| WO | 2008157801 A2 | 12/2008 |
| WO | 2009015048 A2 | 1/2009 |
| WO | 2011006166 A1 | 1/2011 |
| WO | 2012009666 A2 | 1/2012 |
| WO | 2013012798 A1 | 1/2013 |
| WO | 2013049577 A1 | 4/2013 |
| WO | 2013054129 A1 | 4/2013 |
| WO | 2013188446 A1 | 12/2013 |
| WO | 2014009379 A1 | 1/2014 |
| WO | 2015039170 A1 | 3/2015 |
| WO | 2016063068 A2 | 4/2016 |
| WO | 2016063069 A1 | 4/2016 |
| WO | 2016063070 A1 | 4/2016 |
| WO | 2016063072 A1 | 4/2016 |

OTHER PUBLICATIONS

International Search Report and Written Opinion] issued in PCT/GB2015/053173, dated Feb. 2, 2016, 10 pages.

Carrara et al. Multiplexing pH and Temperature in a Molecular Biosensor; Conference Paper, 2010, 4 pages.

Hamacher et al. Efficient Stereospecific Synthesis of No-Carrier-Added 2-[18F]-Fluoro-2deoxy-D-Glucose Using Aminop0lyether Supported Nucleophilic Substitution; J-Nuclear Medicine and Biology vol. 27, 1986, pp. 235-238.

Kugler et al. Optimizing the Transfer of[18F]Fluoride From Aqueous to Organic Solvents by Electrodeposition Using Carbon Electrodes Applied Radiation and Isotopes vol. 91, 2014, pp. 1-7.

Pascali et al. Dose-On-Demand of Diverse [18F] Fluorocholine Derivatives Through a Two-Step Microfluidic Approach; Nuclear Medicine and Biology vol. 38, 2011, pp. 637-644.

Alexoff et al. Recovery of [18F] Flouride From [18O] Water in an Electrochemical Cell Appl. Radiat. Isot. vol. 40 No. 1, pp. 1-6, 1989; Int. J. Radiat. Appl. Instrum Part 4.

Bruchet et al. Centrifugal Microfluidic Platform for Radiochemistry: Potentialities for the Chemical Analysis of Nuclear Spent Fuels; Talanta 116 (2013) pp. 488-494.

Elizarov et al. Design and Optimization of Coin-Shaped Microreactor Chips for PET Radiopharmaceutical Synthesis; Journal of Nuclear Medicine (2010) pp. 282-287.

Hamacher et al. Electrochemical Cell for Separation of [18F] Flouride From Irradiated 18O-Water and Subsequent No Carrier Added Nucleophilic Fluorinaton; Applied Radiation and Isotopes 56 (2002) pp. 519-523.

Hamacher et al. No-Carrier-Added Nucleophilic 18F-Labelling in an Electrochemical Cell Exemplified by the Routine Prodcution of [18F] AltansHerin; Applied Radiation and Isotopes 64 (2006) pp. 989-994.

International Preliminary Report on Paentability issued in PCT/GB2015/053171, dated Apr. 25, 2017, 6 pages.

International Preliminary Report on Patentability issued for PCT/GB2015/053170, dated Apr. 25, 2017, 6 pages.

International Preliminary Report on Patentability issued for PCT/GB2015/053173, dated Apr. 25, 2017, 5 pages.

International Preliminary Report on Patentability issued in PCT/GB2015/053167, report dated Apr. 25, 2017, 17 pages.

International Search Report and Written Opinion issued in PCT/GB2015/053167, dated May 23, 2016, 26 pages.

International Search Report and Written Opinion issued in PCT/GB2015/053170, dated Feb. 4, 2016. 11 pages.

International Search Report and Written Opinion issued in PCT/GB2015/053171, dated Feb. 9, 2016, 11 pages.

Ismail et al. Cationic Imidazolium Polymer Monoliths for Efficient Solvent Exchange, Activation and Fluorinaton on a Continuous Flow System; RSC Adv. (2014), 4, 25348-25356.

Saiki, H. et al. Electrochemical Concentration of No-Carrier-Added [18F] Flouride From [18O] Water in a Disposable Microfluidic Cell for Radiosynthesis of 18F-Labeled Radiopharmaceuticals; Applied Radiation and Isotopes 68 (2010) pp. 1703-1708.

UK Search Report Issued in Application No. GB1418893.2, dated Nov. 3, 2015, 5 pages.

(56) References Cited

OTHER PUBLICATIONS

UK Search Report Issued in Application No. GB1418895.7, dated Apr. 24, 2015, 5 pages.

UK Search Report Issued in Application No. GB1418897.3, dated Jul. 10, 2015, 6 pages.

UK Search Report issued in Application No. GB1418899.9, dated Apr. 24, 2015, 4 pages.

Fletcher, Paul D. I., et al. Permeability of silica monoliths containing micro- and nano-pores. J Porous Mater, 18:501-508, 2011.

Li, Z. and Conti, P.S. Radiopharmaceutical chemistry for positron emission tomography. Advanced Drug Delivery Reviews, 62:1031-1051, 2010.

Mewis, R.E. and Archibald, S.J. (2010). Biomedical applications of macrocyclic ligand complexes. Coordination Chemistry Reviews, Review, 254:1686-1712.

Phelps, M.E. (2000). Positron emission tomography provides molecular imaging of biological processes. PNAS, 97(16):9226-9233.

Silversides, J. D., Smith, R., Archibald, S. J. Challenges in chelating positron emitting copper isotopes: Tailored synthesis of unsymmetric chelators to form ultra stable complexes. Dalton Transactions, "Radiopharmaceuticals for Imaging and Therapy," 40:6289-6297, 2011.

Wood, Laura D., et al. The Genomic Landscapes of Human Breast and Colorectal Cancers. Sciencexpress, Research Article, Oct. 11, 2007, pp. 1-8 paginated and accompanying images.

James P. Grinias et al. "Advances in and prospects of microchip liquid chromatography". Trends in Analytical Chemistry. vol. 8, pp. 110-117. 2016.

Haroun, S.; et al. (2013). Continuous-flow synthesis of [11C]raclopride, a positron emission tomography radiotracer, on a microfluidic chip. Can. J. Chem. 91:326-332.

He, et al., "Monolith-based 68Ga processing: a new strategy for purification to facilitate direct radiolabelling methods," React. Chem. Eng., vol. 1 (2016), pp. 361-365.

Nakao, R. et al. "Improved radiometabolite analysis procedure for positron emission tomography (PET) radioligands using a monolithic column coupled with direct injection micellar/high submicellar liquid chromatography," Talanta 113(2013) 130-134; available online Mar. 15, 2013. (Year: 2013).

Phenomenex. "Onyx—Monolithic Silica HPLC Columns" brochure, 6 pages, 2013; downloaded from <https://phenomenex.blob.core.windows.net/documents/2791ff52-0585-4146-9c00-fbb700e390f0.pdf> on Oct. 24, 2019 (Year: 2013).

Rensch, C.; et al. (2013). Microfluidics: A groundbreaking technology for PET tracer production? Molecules, 18:7930-7956.

Tarn et al., "Positron detection in silica monoliths for miniaturised quality control of PET radiotracers," Chem. Commun., vol. 52 (2016), pp. 7221-7224.

Tarn, M.D. et al. "Purification of 2-[18F]fluoro-2-deoxy-d-glucose by on-chip solid-phase extraction," Journal of Chromatography A, 1280 (2013) 117-121; available online Jan. 15, 2013. (Year: 2013).

Official Action for U.S. Appl. No. 15/521,207, dated Sep. 11, 2020, 9 pages.

Meyer et al., "The stability of 2-[18F]fluoro-deoxy-D-glucose towards epimerisation under alkaline conditions," Applied Radiation and Isotopes, vol. 51, 1999, pp. 37-41.

Official Action for U.S. Appl. No. 15/521,198, dated May 29, 2020, 20 pages.

Official Action for U.S. Appl. No. 15/521,204, dated Mar. 28, 2019, 11 pages. Restriction Requirement.

Official Action for U.S. Appl. No. 15/521,204, dated Jul. 29, 2019, 11 pages.

Official Action for U.S. Appl. No. 15/521,204, dated Mar. 27, 2020, 12 pages.

Official Action for U.S. Appl. No. 15/521,198, dated May 15, 2019, 7 pages. Restriction Requirement.

Official Action for U.S. Appl. No. 15/521,198, dated Nov. 4, 2019, 21 pages.

Official Action for U.S. Appl. No. 15/521,207, dated Oct. 11, 2019, 10 pages. Restriction Requirement.

Official Action for U.S. Appl. No. 15/521,207, dated Feb. 6, 2019, 9 pages.

Official Action for U.S. Appl. No. 15/521,207, dated Jun. 20, 2019, 10 pages.

Official Action for U.S. Appl. No. 15/521,207, dated Oct. 10, 2019, 9 pages.

Official Action for U.S. Appl. No. 15/521,207, dated Mar. 18, 2020, 8 pages.

Official Acton for U.S. Appl. No. 15/521,204, dated Oct. 5, 2020, 9 pages.

* cited by examiner

| Characteristic/analyte | Threshold (European Pharmacopoeia) | Method of Detection |
|---|---|---|
| Appearance / clarity | Clear, colourless or slightly yellow | Absorption spectroscopy and Raman spectroscopy |
| pH | 4.5 - 8.5 | Colourimetric assay with universal pH indicator; absorption spectroscopy |
| Kryptofix 2.2.2 | 2.2 mg/V (or 50 ppm in USP) | Colourimetric assay with iodoplatinate; absorption spectroscopy |
| Residual solvents | Ethanol = 5000 ppm<br>Acetonitrile = 410 ppm | Raman spectroscopy |
| Bacterial endotoxins | 175 IU/V | Colourimetric endpoint LAL assay (three reagents added sequentially: (i) LAL reagent, (ii) chromogenic substrate, (iii) dilute acetic acid); absorption spectroscopy |
| FDG | 0.5 mg/V | Anion exchange liquid chromatography on a strong anion exchange (SAX) monolithic column; sodium hydroxide mobile phase; positron detection and pulsed amperometric detection (PAD) |
| ClDG | 0.5 mg/V | Anion exchange liquid chromatography on a strong anion exchange (SAX) monolithic column; sodium hydroxide mobile phase; positron detection and pulsed amperometric detection (PAD) |
| [18F]FDM | Max. 10% of total activity | Anion exchange liquid chromatography on a strong anion exchange (SAX) monolithic column; sodium hydroxide mobile phase; positron detection and pulsed amperometric detection (PAD) |
| [18F]fluoride+<br>[18F]ACY-FDG+<br>[18F]ACY-FDM | Max. 5% of total activity | Liquid chromatography on a silica or C18 monolithic column; mobile phase of acetonitrile/water mixture; positron detection |
| [18F]FDG+<br>[18F]FDM | Min. 95% of total activity | Liquid chromatography on a silica or C18 monolithic column; mobile phase of acetonitrile/water mixture; positron detection |

V = maximum recommended dose in millilitres

FIG. 7

SYSTEM FOR RADIOPHARMACEUTICAL PRODUCTION

FIELD OF THE INVENTION

Certain embodiments of the present invention relate to a system and a method for producing a radiopharmaceutical, wherein the system is formed from and/or provides a microfluidic flow system. In certain embodiments, the system comprises a radioisotope isolation module, a radiopharmaceutical production module, a purification module and a quality control module.

BACKGROUND TO THE INVENTION

Positron emission tomography (PET) has become a very powerful and widely used medical imaging modality for the diagnosis and monitoring of a variety of diseases and conditions. The technique relies on the (typically) intravenous injection of a radiotracer—a targeting molecule labelled with a short-lived radioisotope—into a patient, and the subsequent scanning of the patient in a PET scanner to image the biodistribution of the tracer.

Because of its appropriate half-life (109.8 min), allowing sufficient time for multistep synthetic labeling reactions and transportation of doses to sites several hours away, and a low positron energy giving high resolution images, $^{18}F$ has become the most widely used and commonly available radioisotope for PET imaging. Currently, 2-[$^{18}F$]fluoro-2-deoxy-D-glucose ([$^{18}F$]FDG) is the most frequently used radiotracer for PET investigations.

Historically, PET tracers were produced in large batches at centralised cyclotron or decay generator facilities and then transported as multiple doses to the imaging sites, usually a hospital, to be administered to multiple patients during pre-arranged PET clinics. However, this does not enable targeting of specific patients with specific conditions, but is more economical since it is easier to produce large volumes of [$^{18}F$]FDG than multiple smaller doses of other radiotracers. Recent technological advances have meant that individual imaging sites are able to have mini-PET cyclotrons on site thus allowing small volumes of radioisotopes such as $^{18}F$ to be produced for the on-demand synthesis of a single dose of radiotracer i.e. "dose-on-demand".

Radiotracers such as [$^{18}F$]FDG can be synthesized by nucleophilic substitution of a precursor compound. The process usually starts with recovery of $^{18}F$ fluoride ions from $^{18}O$-enriched water produced by a cyclotron into an appropriate solvent using an anion exchange separation cartridge, followed by azeotropic evaporation to remove any residual water. Such processes are time-consuming, require complex automation and reduce radiochemical yield. Alternative methods based on an electrochemical cell have been reported in which $^{18}F$ is trapped and then directly released into organic solvent for the preparation of radiotracers without the need for an evaporation step. However, disadvantages of the known processes include low efficiency of trapping and/or release, reliance on high voltages and the use of complex electrochemical cells.

There is an ongoing need for improved preparative methods with regard to synthetic and/or analytical methods in this field.

Clearly, the injection of a solution containing the radiotracer into a human patient necessitates that the injectable dose be sterile, at a physiological pH, be free of particulate matter, and not contain any potentially harmful starting materials or by-products that may be present as a result of the synthesis procedure. With this in mind, stringent quality control (QC) tests must be performed on injectable doses in order to ensure their suitability for human injection. The tests required for a specific radiotracer are listed in various pharmacopoeia monographs, which detail the techniques/instrumentation to be used and the limits allowed for the different molecules present in the dose.

With changes in radiosynthesis technologies comes the need for quality control systems to monitor the radiotracers being produced. While the pharmacopoeia tests set the current standards, they require the use of a variety of different techniques and instrumentation, including thin-layer chromatography (TLC), high performance liquid chromatography (HPLC), and gas chromatography (GC), among others. Nonetheless, there are continuing efforts to lower the limits of detection, shorten the testing times, and reduce the sample volumes required. Recently, efforts have also been made to integrate multiple QC tests into a single technique in order to streamline the QC process, thus reducing the instrumentation required and the radiation exposure experienced by technicians. More generally, streamlining of quality control processes of other compounds which are for in vivo use e.g. pharmaceuticals is also desired.

It is an aim of aspects of the present invention to at least partially mitigate the problems associated with the prior art.

It is an aim of certain embodiments of the present invention to provide a system which is capable of producing and purifying the radiopharmaceutical, and testing the radiopharmaceutical for quality control purposes, wherein the system is suitable for producing a single unit dose of the radiopharmaceutical.

SUMMARY OF CERTAIN EMBODIMENTS OF THE INVENTION

It is an aim of certain embodiments of the present invention to provide, and there is provided, a system for producing a radiopharmaceutical in a microfluidic quantity.

It is an aim of certain embodiments of the present invention to provide a "dose-on demand" system which produces a radiopharmaceutical in a single unit-dose form.

In a first aspect of the present invention, there is provided a microfluidic system for the production of a radiopharmaceutical composition comprising:
 a) a Radioisotope Isolation Module (RIM) configured to receive an aqueous solution comprising a radioisotope;
 b) a Radiopharmaceutical Production Module (RPM) configured to receive a first sample which comprises a concentrated and activated radioisotope from the RIM;
 c) a Purification Module (PM) configured to receive a second sample which comprises a radiopharmaceutical and one or more further components from the RPM; and
 d) a Quality Control Module (QCM), configured to receive a third sample from the PM which comprises a purified radiopharmaceutical and which is further configured to determine one or more characteristics of the third sample, wherein each of the modules is a microfluidic component.

Aptly, the system is configured to produce per run a single (one) unit dose of the radiopharmaceutical composition. Aptly, the system has a total volume capacity of less than about 2 ml. Aptly, the system has a total volume capacity of less than about 1 ml, e.g. 500 µl e.g. less than about 300 µl.

In one embodiment, the RIM comprises an apparatus, e.g. a microfluidic cell, for separating and recovering a radioactive isotope from an aqueous solution comprising the radioactive isotope, the apparatus comprising:
- an inlet;
- an outlet; and
- a chamber in fluid communication with the inlet and the outlet to form a fluid pathway, the chamber comprising a first electrode and a second electrode, wherein the first electrode is formed from a carbon rod;
wherein the chamber has a volume capacity of no greater than about 50 µL; and
wherein the distance between the first electrode and the second electrode is no greater than 0.5 mm.

Aptly, the surface area of the first electrode which comes into contact with the flow of aqueous solution is at least 20 mm². In one embodiment, the first electrode has a flat surface comprising a plurality of recesses. Aptly, the first electrode has a polished surface layer. Aptly, the apparatus is configured to receive fluid at a flow rate of at least 0.1 mL/min.

In one embodiment, the second electrode is made of platinum.

Aptly, the first electrode has a hardness of at least 2.0 on the Mohs scale. In one embodiment, the chamber has a volume capacity of no greater than about 30 µL. Aptly, the RIM further comprises a heater. Aptly, the RIM is or comprises a microfluidic cell.

In one embodiment, the RIM comprises a chromatographic monolithic body configured to separate the radioactive isotope from the aqueous based solution, wherein the monolithic body is an inorganic monolithic body.

In one embodiment, the system comprises an RPM which comprises a chromatographic monolithic body configured to separate the radioactive isotope from the aqueous based solution, wherein the monolithic body is an inorganic monolithic body.

In one embodiment, the system comprises a PM comprises a chromatographic monolithic body configured to separate the radioactive isotope from the aqueous based solution, wherein the monolithic body is an inorganic monolithic body. Aptly, the PM comprises a plurality of chromatographic monolithic bodies.

Aptly, the monolithic body comprises a composition selected from a silicon based composition, an aluminium based composition and a titanium based composition, wherein each composition is optionally chemically functionalised. Aptly, the composition is selected from a silica-based composition, an alumina-based composition and a titania-based composition, wherein each composition is optionally chemically functionalised. Aptly the monolithic body comprises a silicon based composition selected from silica, silicon imido nitride, silicon imide and silicon nitride, wherein each composition is optionally chemically functionalised.

Aptly, the monolithic body comprises silica or silica chemically functionalised. In one embodiment, the monolithic body is a cation exchange monolithic body, for example the monolithic body comprises silica modified with propyl sulfonic acid groups.

In one embodiment, the monolithic body is an anion exchange monolithic body, for example the monolithic body comprises silica modified with quaternary ammonium. In one embodiment, the the monolithic body is a reverse phase monolithic body, for example the monolithic body comprises silica modified with octadecyl carbon groups.

Standard monolithic HPLC columns are commercially available for example from organisations such as Phenomenex, Merck, Thermo Scientific and Agilent.

In an alternative embodiment, the RPM comprises a serpentine mixing channel.

In one embodiment, the aqueous solution is produced from a cyclotron or a decay generator. Aptly, the radioactive isotope is $^{89}Zr$, $^{64}Cu$, $^{18}F$ or $^{68}Ga$ or cation thereof. (for example $^{88}Ga^{3+}$).

In an embodiment, the system further comprises one or more inlets in fluid communication with the RIM for introducing a radiopharmaceutical precursor or protected form thereof (for example acetylated [$^{18}F$]FDG).

In one embodiment, the Purification Module (PM) is configured to receive a second sample which comprises a radiopharmaceutical and one or more further components from the RPM and separate the radiopharmaceutical from the one or more further components.

Aptly, the radiopharmaceutical is selected from $^{18}F$-FLT ([$^{18}F$]fluoro thymidine), $^{18}F$-FDDNP (2-(1-{6-[(2-[$^{18}F$]fluoroethyl)(methyl)amino]2-naphthyl}ethylidene)malonitrile), $^{18}F$-FHBG (9-[4-[$^{18}F$]fluoro-3-(hydroxymethyl)butyl]guanine or [$^{18}F$]penciclovir), $^{18}F$-FESP ([$^{18}F$]fluoroethylspiperone), $^{18}F$-p-MPPF (4-(2-methoxyphenyl)-1-[2-(N-2-pyridinyl)-p-[$^{18}F$]fluorobenzamido]ethylpiperazine), $^{18}F$-FDG (2-[$^{18}F$]fluoro-2-deoxy-D-glucose), $^{18}F$-FMISO ([$^{18}F$] fluoromisonidazole) and $^{18}F$-sodium fluoride.

In one embodiment, the one or more further components is an impurity. In one embodiment, the impurity selected is from [$^{18}F$]fluoride and endotoxin and the monolithic body is a normal phase monolithic body (for example comprising alumina or silica).

In one embodiment, the impurity is selected from acetylated [$^{18}F$]FDG, acetylated [$^{18}F$]FDM, CIDG, mannose triflate and K222, and the monolithic body is a reverse phase monolithic body (for example comprising silica modified with octadecyl carbon).

In one embodiment, the impurity is selected from K222 and sodium hydroxide and the monolithic body is a cation exchange monolithic body (for example silica modified with propyl sulfonic acid groups). In one embodiment, the impurity is selected from hydrochloric acid and the monolithic body is an anion exchange monolithic body (for example silica modified with quaternary ammonium).

In one embodiment, the system comprises a QCM which comprises a microfluidic chip for determining at least one characteristic of the third sample, the microfluidic chip comprising:
- a) a length (L1), a width (W1) and a thickness (T1) wherein T1<W1 and T1<L1;
- b) a supply component for introducing the sample into the chip;
- c) a fluid flow path in fluid communication with the supply component, and
- c) a detection channel in the fluid flow path, wherein the detection channel extends at least partially through the thickness (T1) of the microfluidic chip and wherein the detection channel is configured to provide both a fluid flow path and a path length along a long axis thereof.

Thus, the chip comprises a detection channel which extends at least partially through the thickness of the chip. Aptly, in use the detection channel provides an optical pathlength between a detector and a source, such that absorbance of a fluid in the detection channel may be determined. In one embodiment, the source is capable of emitting electromagnetic radiation at a wavelength of between about 2 nm to about 2 mm. In one embodiment, the path length and the fluid flow path are provided along the same axis of the detection channel. In one embodiment, the detection channel is approximately 2 mm to 4 mm in length. In one embodiment, the detection channel is approximately 3 mm to 4 mm in length.

In an embodiment, the chip comprises a plurality of layers e.g. two or three or more.

In one embodiment, the detection channel is enclosed within the microfluidic chip, and optionally wherein the chip further comprises one or more valve elements for directing and/or controlling fluid flow in the fluid flow path. Aptly, the detection channel is axially aligned with the light source and the detector in use. Aptly, the detector and/or the light source each comprise a connecting element for connecting the chip to the detector and/or source and wherein the detection channel is axially aligned with the connecting element(s) in use.

Aptly, at least a portion of the chip is composed of a material which is capable of optical transmission. Aptly, each portion of the chip which is positioned adjacent to the light source and the detector in use is capable of optical transmission.

In one embodiment, the fluid flow path comprises a first microchannel. Aptly, the microfluidic chip comprises at least one further microchannel. In certain embodiments, the first microchannel and/or the at least one further microchannel are provided in a different plane to the detection channel. In one embodiment, the detection channel comprises an upper opening and a lower opening, each contained within the chip, and wherein the detection channel is configured to permit flow of a fluid along a long axis thereof.

Aptly, an outlet is provided in fluid communication with the lower opening of the detection channel. Aptly, an outlet is provided in fluid communication with the upper opening of the detection channel. In one embodiment, the microfluidic chip comprises a plurality of detection channels. In one embodiment, the detection channel is a detection zone and the microfluidic chip further comprises one or more further detection zones.

In an embodiment, the QCM comprises a microfluidic chip comprising:
 a) a supply component for introducing the third sample to the microfluidic chip;
 b) a fluid flow path in fluid communication with the supply component;
 c) at least two detection zones, each detection zone comprising an component for performing an analytical technique;
 d) a plurality of isolation valve elements provided in the fluid flow path to control and/or direct fluid flow in the fluid flow path;
 wherein each isolation valve element is movable from an open position to a closed position such that a portion of the third sample is isolated for direction to a detection zone.

In one embodiment, the fluid flow path comprises a first microchannel which comprises a plurality of isolation valve elements. In one embodiment, the chip comprises at least one further microchannel, wherein each further microchannel is in fluid communication with a different portion of the first microchannel provided between a pair of isolation valve elements. Aptly, a portion of the third sample is isolated between pairs of the isolation valve elements and wherein the at least one further microchannel intersects the first microchannel at a junction between a pair of isolation valve elements.

In one embodiment, the at least one further microchannel comprises a pair of further isolation valve elements, one of the pair of further isolation valve elements being provided at a first location upstream of the junction and the other of the pair of further isolation valve elements being positioned at a location downstream of the junction. Aptly, the pair of further isolation valve element provided in the at least one further microchannel are configured to be in a closed position when the pair of isolation valve elements of the first microchannel are in an open position.

Aptly, the isolation valve element is a valve assembly as described herein below.

According to a yet further aspect of the present invention, there is provided a valve assembly for a microfluidic chip, comprising:
 a valve member having a valve axis, a first end region and a further end region; and
 a valve housing engagable with a microfluidic chip to locate the further end region of the valve member in a fluid flow path of the microfluidic chip;
 wherein the further end region of the valve member comprises at least one through conduit and the valve member is rotatable about the valve axis with respect to the valve housing to selectively move the at least one through conduit between an open position and a closed position relative to the fluid flow path of the microfluidic chip.

Aptly, the valve member is translatable in a direction along the valve axis with respect to the valve housing.

In certain embodiments, the valve assembly further comprises a biasing element to bias the further end region of the valve member away from the valve housing in a direction along the valve axis.

Aptly, the valve member is substantially elongate and comprises an annular shoulder portion disposed between the first end region and the further end region for engagement with the biasing element.

Aptly, the valve housing comprises an annular wall portion and an upper portion having a central aperture to receive the valve member and to locate the biasing element between the upper portion and the annular shoulder of the valve member.

In certain embodiments, the annular wall portion comprises a first screw thread for engagement with a further screw thread of the microfluidic chip.

Aptly, the biasing element comprises a compression spring. Aptly, the compression spring has a spring force associated with a predetermined threshold pressure of fluid transportable in the fluid flow path of the microfluidic chip.

Aptly, the valve assembly further comprises an adjuster for adjusting a length of the compression spring.

Aptly, the valve member comprises a valve shaft extending from a valve head portion comprising the at least one through conduit. In certain embodiments, the valve shaft is received in a central bore of the valve head portion. Aptly, the valve shaft and the valve head portion are connected by at least one of an adhesive, a friction fit, and a screw thread.

Aptly, the valve shaft comprises the annular shoulder portion and an upper surface of the valve head portion abuts a lower surface of the annular shoulder portion. In certain embodiments, the valve head portion comprises a substantially resilient material. Aptly, the substantially resilient material comprises a biomedical grade elastomer. In certain embodiments, the biomedical grade elastomer comprises a silicone rubber.

Aptly, the valve shaft and valve housing each comprise a metal or polymer material. In certain embodiments, the at least one through conduit comprises at least one channel disposed in a lower surface of the further end region of the valve member.

Aptly, the channel comprises a width of about 100 μm to about 200 μm e.g. about 150 μm and a depth of for example about 50 μm deep.

Aptly, the first end region of the valve member comprises a spline for engagement with an actuator to drive the valve member relative to the valve axis.

In one embodiment, each of the at least one further microchannel is in fluid communication with a detection zone. In one embodiment, a plurality of further microchannels is in fluid communication with a single detection zone. In one embodiment, the at least one further microchannel comprises a downstream valve element to control and/or direct flow of a fluid from the plurality of further microchannels to the detection zone.

Aptly, the detection zone comprises one or more of the analytical components selected from:
a) an electrochemical cell;
b) a radiation detector;
c) a separation element; and
d) a detection channel.

Aptly, the chip comprises a plurality of detection zones, each detection zone comprising at least one analytical component.

Aptly, the analytical component is an electrochemical cell which comprises a working electrode, a counter electrode and a reference electrode.

In one embodiment, the working electrode is a gold electrode. Alternatively, the working electrode is formed from platinum, ITO (indium tin oxide) or carbon. Aptly, the counter electrode (also referred to as an "auxiliary electrode") is formed from silver, carbon or platinum. Aptly, the reference electrode is formed from silver.

Aptly, the electrochemical cell is a screen-printed electrode assembly.

In one embodiment, the separation element is a monolithic body, and optionally wherein the monolithic body is a normal phase monolithic body (for example comprising alumina or silica) and/or a strong anion exchange (SAX) monolithic body and/or a reversed phase (C18) monolith. In certain embodiments, the separable component comprises a plurality of monolithic bodies, which may be the same or different. Aptly, the separable component comprises two monolithic bodies.

Aptly, the detection zone further comprises one or more inlets for supplying a reagent or a mobile phase and optionally wherein the chip further comprises one or more outlets.

Aptly, the supply component is an inlet port. In one embodiment, the fluid flow path comprises at least one passive mixing element in at least a portion thereof, wherein optionally the passive mixing element is selected from staggered herringbone pattern, a straight ridge, an angled ridge, a chevron canal, a dome, a cone, a pit, a post and a combination thereof.

In one embodiment, the QCM is for determining:
a) pH of the sample;
b) clarity of the sample;
c) presence and/or concentration of bacterial endotoxin in the sample; and
d) presence and/or concentration of an impurity in the sample; and/or
e) radiation level of the sample.

In one embodiment, the system is a continuous flow system. In one embodiment, the system is a modular system and wherein each module is separable from all other modules. In one embodiment, the modules are in fluid communication by way of a microfluidic flow path.

In one embodiment, the system is an integrated system and the RIM, RPM, PM and QCM are provided on a unitary microfluidic device.

In one embodiment, the device comprises one or more microchannels configured to provide a microfluidic flow path between the modules and/or one or more valve elements to direct and/or control flow between the modules. Aptly, the PM is in fluid communication with an outlet configured to remove at least a portion of the third sample upstream from the QCM.

Aptly, the system further comprises:
a) a source; and/or
b) a detector.

Aptly, the source is a light source. In one embodiment, the detector is a spectrometer e.g. a visible-near infrared spectrometer, a UV-visible light spectrometer or a Raman spectrometer. Aptly, the system comprises one or more connecting elements for aligning the detector and/or the source to the microfluidic chip. Aptly, the source and the detector and/or the connecting element(s) are aligned such they are orthogonal to the chip of the QCM and aligned with a long axis of the detection channel such that the detection channel provides a path length between the source and the detector.

In a further aspect of the present invention there is provided a method of producing a radiopharmaceutical composition comprising:
a) supplying an aqueous solution comprising a radioisotope to a Radioisotope Isolation Module (RIM) and forming a first sample comprising a concentrated and activated radioisotope;
b) supplying the first sample which comprises a concentrated and activated radioisotope from the RIM to a Radiopharmaceutical Production Module (RPM);
c) supplying a second sample which comprises a radiopharmaceutical and one or more further components to a Purification Module (PM) configured to receive a second sample from the RPM;
d) supplying a third sample which comprises a purified radiopharmaceutical from the PM to a Quality Control Module (QCM); and
e) performing at least one analytical technique on the third sample or a portion thereof to determine at least one characteristic of the sample, wherein each of the modules is a microfluidic component.

Aptly, the RIM, the RPM and the QCM are microfluidic devices.

In one embodiment, step (a) comprises supplying the aqueous solution to a RIM comprising a chromatographic monolithic body and eluting the aqueous solution through a chromatographic monolithic body, wherein the monolithic body is an inorganic monolithic body and is part of a microfluidic flow system.

Aptly, step (a) comprises:
flowing the aqueous solution to the RIM, wherein RIM comprises a microfluidic cell comprising a chamber, the chamber comprising a first electrode and a second electrode;
generating a first electric field between the first and second electrodes, thereby trapping the radioisotope on the first electrode;
flowing an organic-based solution to the chamber comprising the first and the second electrodes; and
generating a second electric field between the first and the second electrodes, wherein the second electric field has an opposing polarity to the first electric field, thereby releasing the radioactive isotope from the first electrode into the organic based solution, wherein the first electrode is formed from a carbon rod or section thereof.

Aptly, the method of step (a) comprises providing a flow of the aqueous solution at a flow rate of at least 0.1 mL/min. Aptly, the method of step (a) comprises providing a flow of the organic-based solution at a flow rate of at least 0.05 mL/min.

In one embodiment, the first electric field is generated by applying a voltage of no greater than 30 V across the first and second electrodes and optionally applying a voltage of no greater than 10 V across the first and second electrodes. Aptly, the chamber has a volume of no greater than approximately 50 µL. Aptly, the first electrode has a flat surface comprising a plurality of recesses. Aptly, the distance between the first and second electrodes is no greater than 0.5 mm.

In one embodiment, in step (a) the radioisotope is trapped on the first electrode with an efficiency of at least 94% and/or the radioisotope is released from the first electrode with an efficiency at least 96%. Aptly, the method of step (a) further comprises removing the aqueous solution from the chamber prior to providing the flow of the organic-based solution to the chamber. In one embodiment, the method of step (a) further comprises washing the chamber after trapping the radioisotope on the first electrode and before providing the flow of an organic-based solution to the chamber.

Aptly, the organic-based solution comprises an organic solvent, wherein optionally the organic solvent further comprises from 1% to 10% $H_2O$. Aptly, the method of step (a) further comprises heating the chamber and/or the organic based solution to a temperature of from 50 to 100° C. prior to generating the second electric field.

In an embodiment, step (b) further comprises reacting the radioisotope of the first sample with a precursor or protected form thereof to provide the second sample comprising a radiopharmaceutical or an intermediate and optionally one or more further components. Aptly, said reacting step is carried out on a chromatographic monolithic body.

In an embodiment, step (c) comprises purifying the second sample and wherein the purification is carried out on one or more chromatographic monolithic bodies, wherein optionally the method comprises separating the radiopharmaceutical from an impurity.

In an embodiment, step (c) comprises purifying the second sample and wherein the purification is carried out on one or more chromatographic monolithic bodies, wherein optionally the method comprises removing impurities selected from [$^{18}$F]fluoride, endotoxin and other polar impurities to form the third sample and wherein the monolithic body is a normal phase monolithic body (for example comprising alumina or silica).

In one embodiment, step (c) comprises purifying the second sample and wherein the purification is carried out on one or more chromatographic monolithic bodies, wherein optionally the method comprises separating the radiopharmaceutical from an impurity selected from acetylated [$^{18}$F]FDG, acetylated [$^{18}$F]FDM, mannose triflate, K222 and other non-polar impurities, to form the third sample and wherein the monolithic body is a reverse phase monolithic body (for example comprising silica modified with octadecyl carbon).

In one embodiment, step (c) comprises purifying the second sample and wherein the purification is carried out on one or more chromatographic monolithic bodies, and optionally wherein the method comprises separating the radiopharmaceutical from an impurity selected from K222, sodium hydroxide and other cationic impurities to form the third sample and the monolithic body is a cation exchange monolithic body (for example silica modified with propyl sulfonic acid groups).

In one embodiment, step (c) is carried out on one or more chromatographic monolithic bodies, and optionally wherein the method comprises separating the radiopharmaceutical from an impurity selected from hydrochloric acid and other anionic impurities to form the third sample and the monolithic body is an anion exchange monolithic body (for example silica modified with quaternary ammonium).

In one embodiment, step (d) comprises performing at least one analytical technique on the third sample or the portion thereof on a detection zone. Aptly, step (d) comprises:

a) determining pH of the sample;
b) determining presence and/or a concentration of an impurity in the sample;
c) determining the concentration of bacterial endotoxin in the sample; and/or
d) determining the clarity and/or appearance of the sample or a portion thereof.

In certain embodiments, the method comprises performing a plurality of analytical techniques on the sample or portion thereof. Aptly, the analytical techniques are performed simultaneously or sequentially. Aptly, step (d) further comprises performing a spectroscopic technique on the third sample or a portion thereof or a mixture comprising the third sample or a portion thereof. Aptly, the method comprises performing visible-near infrared spectroscopy, UV-visible spectroscopy or Raman spectroscopy on the third sample or a portion thereof. In one embodiment, the method comprises positioning a light source and a detector such that the detection zone is provided between the light source and the detector and provides a path length for light emitted by the light source to be transmitted to the detector and performing a spectroscopic technique.

Aptly, the detection zone comprises a detection channel extending at least partially through a thickness of the microfluidic chip, wherein the detection channel provides a path length for light from the light source to be transmitted to the detector.

In one embodiment, the method comprises determining a radiation level of the sample. Aptly, the microfluidic chip comprises a plurality of detection zones, wherein one or more characteristics are determined at each detection zone.

In certain embodiments, the method is performed using the system described herein. Aptly, the method produces a single (one) unit dose of the radiopharmaceutical composition per run.

The content of UK Patent Application No. 1418895.7, UK Patent Application No: 1418897.3, UK Patent Application No 1418893.2 and UK Patent Application No 1418899.9 are hereby incorporated herein by reference.

DETAILED DESCRIPTION OF EMBODIMENTS OF THE INVENTION

Certain embodiments of the present invention will now be described by way of example and with reference to the accompanying drawings in which:

FIG. 7 is a table of certain characteristics determined by the QCM of certain embodiments of the present invention.

Figure 16A:
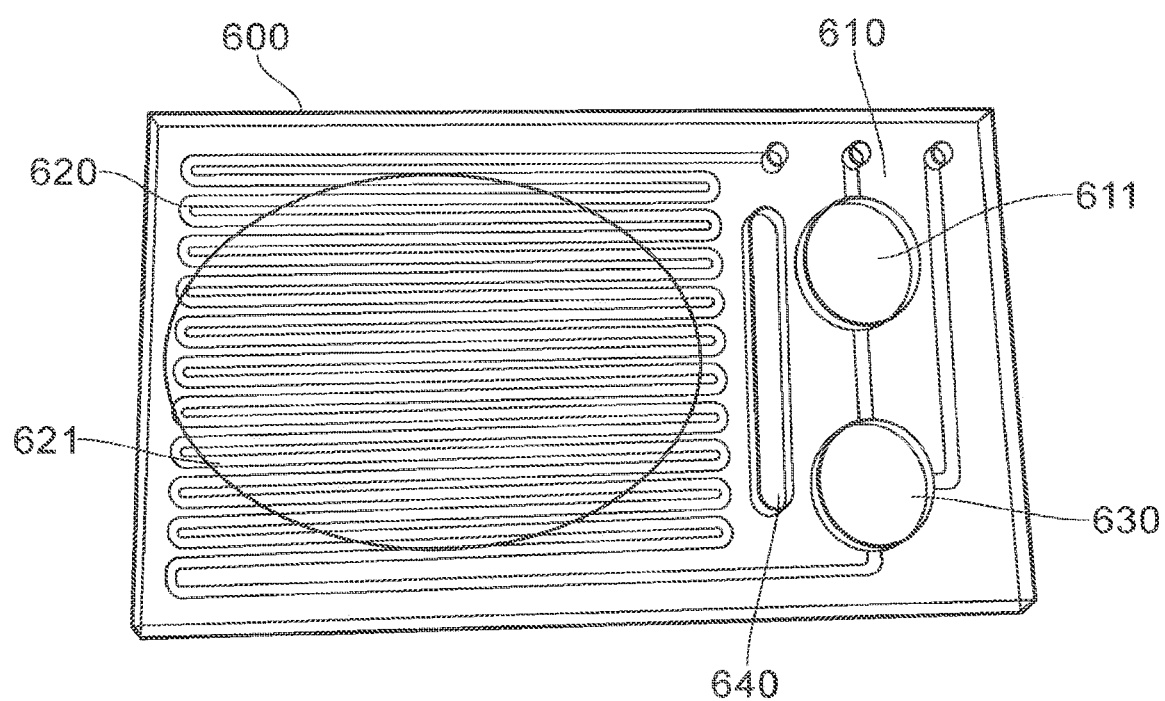
FIG. 16a illustrates a combined RIM and RPM module according to certain embodiments of the present invention.
Figure 16B:
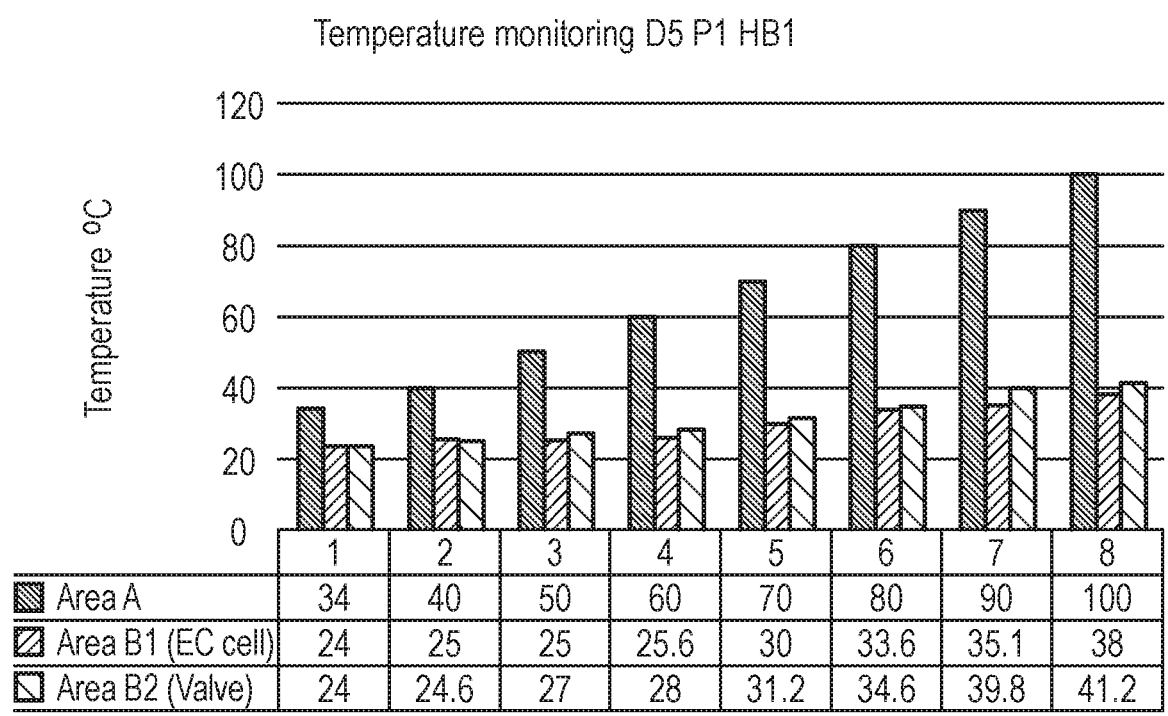
Figure 17:
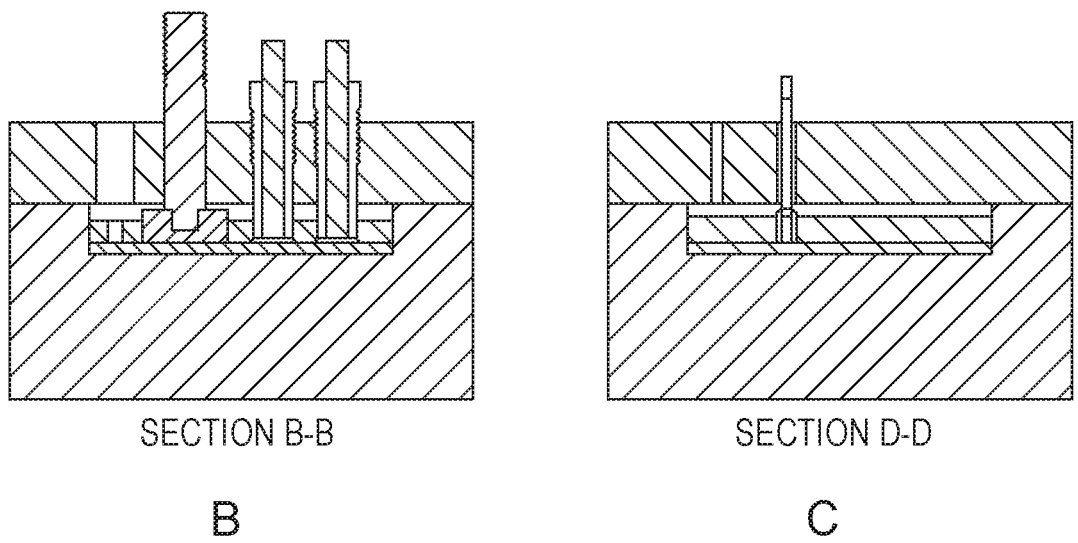

FIG. 16b is a graphical representation of the temperature difference between an RPM and an RIM as measured by an infrared thermometer following direct heating of the RPM according to certain embodiments; and FIG. 17 illustrates the combined RIM and RPM module of FIG. 16a provided in a holder. The combined system may further comprise one or more valve assemblies as described herein for controlling flow of a sample solution between or within the RIM and RPM.

As used herein, like reference numbers refer to like parts.

It will be appreciated that many of the terms and phases used within this specification will be known to the person skilled in the art. Definitions provided herein are intended as embodiments of the invention separately and in any combination with any other embodiments and/or definitions herein.

As used herein, an "analyte" is one or more substance(s) to be selected out of or separated from a sample. When an analyte is separated from a sample by a chromatographic monolithic body, it may be retained on the body or it may elute more slowly through the body than other substance(s) in the sample. An analyte may be a substance of interest, for example a compound or isotope of interest, or it may be an impurity to be removed from a composition of substances. In some embodiments, an analyte may be a reactant.

As used herein, the "sample" is the material to be investigated or analysed by a chromatographic method. The sample may comprise a single component of a mixture of component. The sample comprises the analyte and optionally other substances from which the analyte is to be separated. In some embodiments, a sample may comprise a reactant and may be eluted through a chromatographic monolithic body to effect a chemical reaction, for example a solid phase chemical reaction on the surface of the monolithic body.

As used herein, the "eluent" is the solvent that carries the analyte and any substances that the analyte is to be separated from. The eluent carries the sample.

As used herein, the "eluate" is the mobile phase flowing out of the chromatographic body, in particular, after the analyte has been separated from the sample.

As used herein, the "mobile phase" comprises the phase flowing through the chromatographic body. The mobile phase comprises the sample dissolved in the eluent flowing into the chromatographic body.

Certain embodiments of the present invention relate to a microfluidic system and microfluidic components thereof. A fluid flow can be described as "microfluidic" (i.e. "microfluidic fluid flow") if a fluid passes through a channel having at least one dimension of less than 1 mm, in particular a channel having a dimension of less than 1 mm, e.g. less than 500 µm, less than 250 µm, less than 200 µm, or less than 150 µm. This creates laminar flow characteristics (generally having a Reynolds number of less than 100) where diffusion is the dominant cross stream chemical interaction. Consequently, microfluidic fluid flow occurs during the manipulation of small volumes, for example from 1 nl to 100 µl, within microstructured devices that features dimensions of the order of 10's to 100's µm.

The microfluidic system of certain embodiments of the invention may be a modular system composed of a plurality of separate components, wherein one or more of the components are in fluid communication in use. The system may alternatively be an integrated system wherein one or more e.g. all of the components are provided on a single platform such as for example a microfluidic device e.g. a device comprising a chip. The device may comprise or be comprised in a microfluidic flow system.

A "microfluidic flow system" comprises a system having at least one channel for fluid flow, the channel having at least one dimension of less than one 1 mm, for example less than 500 µm, e.g. 300 µm, 200 µm, 150 µm, 100 µm, 50 µm or less. The microfluidic flow system comprises a microfluidic device but may also comprise other components that are in fluid communication with the microfluidic device.

In one embodiment, the system comprises one or more channels having a width of, for example, between about 100 µm to about 200 µm e.g. about 150 µm and a depth of for example about 50 µm deep.

A "microfluidic chip" can be identified by the fact that it has one or more channels with at least one dimension less than 1 mm, for example, less than 500 µm, e.g. 300 µm, 200 µm, 150 µm, 100 µm, 50 µm or less, in particular a channel having a dimension of less than 1 mm, e.g. for example, between about 100 µm to about 200 µm e.g. about 150 µm and a depth of for example about 50 µm deep. The microfluidic chip may be part of a microfluidic flow system. The one or more channels may form a fluid flow path in the chip.

As used herein, the term "microfluidic chip" refers to a device which can be used for synthetic or analytical purposes for samples having a volume of from about 10 nl and 10 ml. In one embodiment, the microfluidic chip is used to process, synthesise and/or analyze samples having a volume of between about 1 µl and 2000 µl e.g. about 1000 µl or less e.g. 500 µl. In one embodiment, the microfluidic chip is a microfluidic device and/or comprised within a microfluidic device. In certain embodiments, the microfluidic chip may comprise one or more separable modular components e.g. components comprising an electrochemical cell and the like. Aptly, the modular component may comprise a detection zone as described herein.

As used herein, the term "pathlength" refers to a distance travelled by light through a fluid e.g. a sample. Aptly, the microfluidic chip comprises a detection channel which is of a length suitable to provide a path length for a spectroscopic technique.

Aptly, the detection channel is at least 2 mm in length, e.g. 2.5 mm, 3 mm, 3.5 mm or greater. The Reynolds number which is used to characterise microfluidic flow (i.e. the flow of a fluid through a microfluidic channel is calculated according to equation 1:

$$Re = \frac{LV_{avg}\rho}{\mu} \quad \text{equation 1}$$

wherein:
L is the most relevant length scale;
µ is the viscosity;
ρ is the fluid density; and
$V_{avg}$ is the average velocity of the flow.
For many microchannels:
L=4A/P wherein: equation 2
A is the cross sectional area of the channel; and
P is the wetted perimeter of the channel.

Due to the small dimensions of the channels in a microfluidic device, $R_e$ is usually less than 100, in particular less than 1.0. Fluid flow with a Reynolds number of this magnitude is completely laminar with very little or no turbulence such that molecular transport is relatively predictable.

A "radiopharmaceutical" is an isotopically labelled analogue of a pharmaceutical molecule, wherein the isotope label is radioactive. A radiopharmaceutical can be used for diagnostic or therapeutic purposes. The system of certain embodiments can be used to produce a radiopharmaceutical e.g. as described herein.

A "radiotracer" is a radiopharmaceutical having a largely unaltered metabolic pathway compared to the unlabelled analogue. It is therefore possible to follow and quantify processes on a particular metabolic pathway by detecting the radioactive decay of the labelling radioisotope. Radiotracers are used for diagnostic purposes.

Examples of radiotracers include, but are not limited to, $^{18}$F-FLT ([$^{18}$F]fluoro thymidine), $^{18}$F-FDDNP (2-(1-{6-[(2-[$^{18}$F]fluoroethyl)(methyl)amino]2-naphthyl}ethylidene)malonitrile), $^{18}$F-FHBG (9-[4-[$^{18}$F]fluoro-3-(hydroxymethyl)butyl]guanine or [$^{18}$F]penciclovir), $^{18}$F-FESP ([$^{18}$F]fluoroethylspiperone), $^{18}$F-p-MPPF (4-(2-methoxyphenyl)-1-[2-(N-2-pyridinyl)-p-[$^{18}$F]fluorobenzamido]ethylpiperazine), $^{18}$F-FDG (2-[$^{18}$F]fluoro-2-deoxy-D-glucose), $^{18}$F-FMISO ([$^{18}$F]fluoromisonidazole) and $^{18}$F-sodium fluoride.

$^{18}$F-FDG or [$^{18}$F]FDG is a radiolabelled sugar molecule. When used with PET imaging, images are produced that show the metabolic activity of tissues. In FDG-PET scanning, the high consumption of the sugar by tumour cells, as compared to the lower consumption by normal surrounding tissues, identifies these cells as cancer cells. FDG is also used to study tumour response to treatment. As used herein, the term FDG relates to the compound 2-fluoro-2-deoxy-D-glucose and the term $^{18}$F-FDG or [$^{18}$F]FDG relates to radiolabelled (2-[$^{18}$F]fluoro-2-deoxy-D-glucose.

Sodium $^{18}$fluoride is an imaging agent for PET imaging of new bone formation. It can assess changes both in normal bone as well as bone tumours. As a result, it can be used to measure response to treatment.

$^{18}$F-FLT or [$^{18}$F]FLT is a radiolabeled imaging agent that is being investigated in PET imaging for its ability to detect growth in a primary tumour. Studies may also measure the ability of FLT with PET to detect tumour response to treatment.

$^{18}$F-FMISO or [$^{18}$F]FMISO is an imaging agent used with PET imaging that can identify hypoxia (low oxygen) in tissues. Tumours with low oxygen have been shown to be resistant to radiation and chemotherapy.

Alternatively, the radiotracer is a radiopharmaceutical which incorporates a radioisotope selected from the group consisting of $^{89}$Zr, $^{11}$C, $^{68}$Ga and $^{64}$Cu.

Further examples of radiotracers include any which use bifunctional chelators to form conjugates of $^{68}$Ga-DOTA, $^{68}$Ga-NOTA and $^{68}$Ga-DTPA with peptides, antibodies and other targeting vectors. Examples of $^{68}$Ga based radiotracers include $^{68}$Ga-DOTA-TATE and $^{68}$Ga-DOTA-TOC which can be used to image neuroendocrine tumours through recognition of somatostatin receptors.

$^{68}$Ga-NOTA-bis (phosphonate) is PET radiotracer for bone imaging, $^{68}$Ga-DOTATOC is a PET radiotracer for imaging in patients with meningiomas.

$^{68}$Ga-DOTATATE is a PET radiotracer for imaging in patients with malignant phaeochromocytomas.

K222 is Kryptofix 2.2.2, referred to as "aminopolyether" in the BP. It is usually the phase transfer catalyst of choice in the synthesis of [$^{18}$F]FDG by nucleophilic substitution. However, other catalysts such as tetrabutylammonium and 4-(4-methylpiperidin-1-yl)pyridine could be employed.

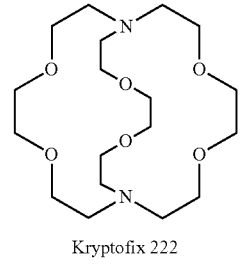 [SMILES: C1COCCN2CCOCCOCCN(CCO1)CCOCCOCC2]

Kryptofix 222

DOTA is 1,4,7,10-tetraazacyclododecane-1,4,7,10-tetraacetic acid.

DTPA is diethylene triamine pentaacetic acid.

NOTA is 1,4,7-triazacyclononane-1,4,7-triacetic acid.

CIDG is 2-chloro-2-deoxy-D-glucose. CIDG is an impurity that can be present particularly when using acid hydrolysis in which a chloride atom takes the place of the [$^{18}$F]fluoride label. A further source of chloride may be an anion exchange cartridge used to pre-concentrate the [$^{18}$F]fluoride label in many systems, depending on the counter ion present on the cartridge resin.

ACY-[$^{18}$F]FDG refers to the acetylated/unhydrolysed form of [$^{18}$F]FDG, which is 2-[$^{18}$F]fluoro-1,3,4,6-tetra-O-acetyl-D-glucose (also referred to as [$^{18}$F]TAG), while partially hydrolysed ACY-[$^{18}$F]FDG can also be present.

[$^{18}$F]FDM is 2-[$^{18}$F]fluoro-2-deoxy-D-mannose, a byproduct that can be produced during the [$^{18}$F]FDG synthesis process, and which can also be present in fully or partially hydrolysed form (ACY-[$^{18}$F]FDM).

A "radiopharmaceutical composition" comprises a radiopharmaceutical, or a pharmaceutically acceptable salt thereof, in association with a pharmaceutically acceptable adjuvant, diluent or carrier. In one embodiment, a radiopharmaceutical composition may comprise the radiopharmaceutical and an isotonic saline solution.

Figure 1:
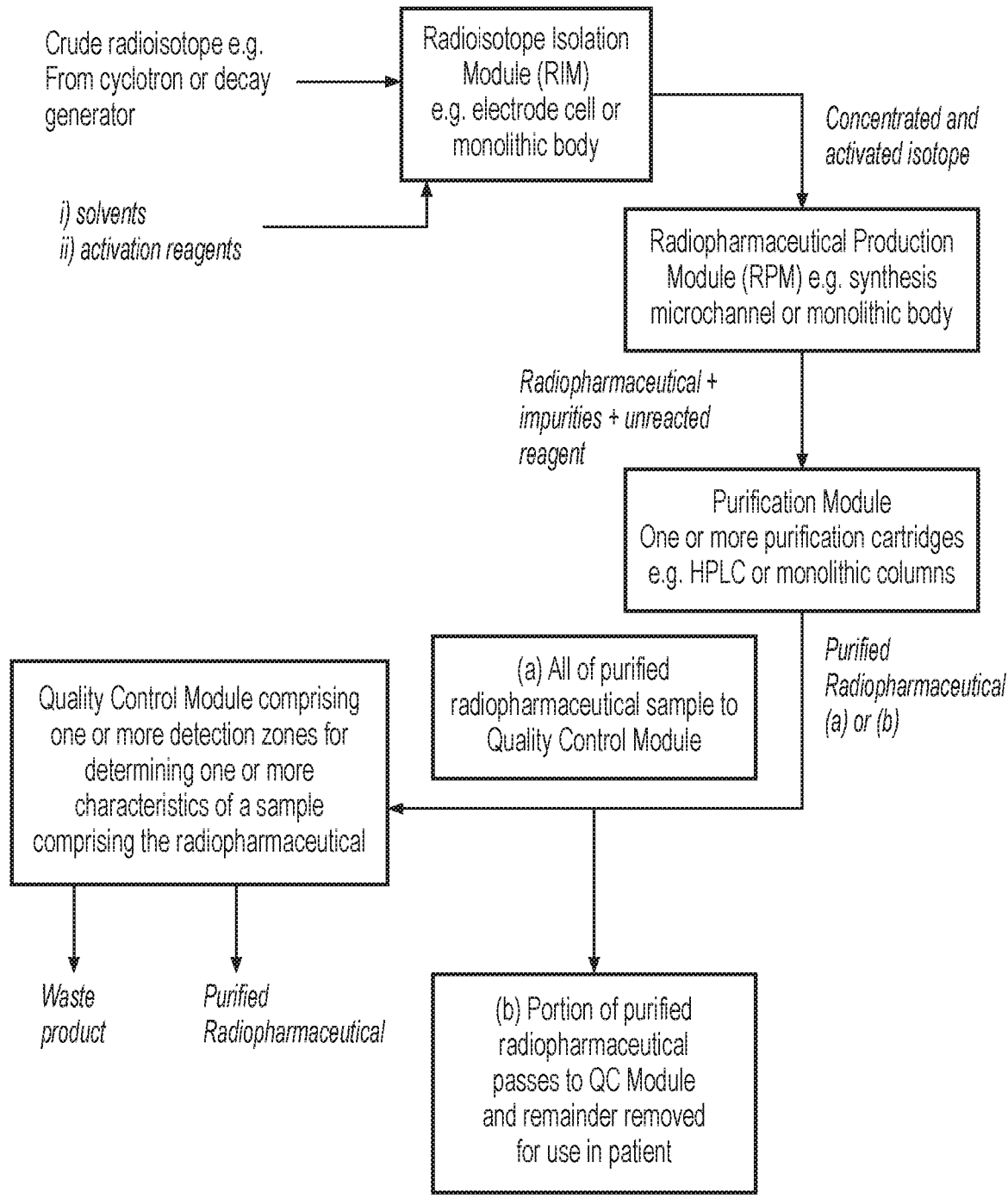
FIG. 1 is a schematic flow diagram of the system of certain embodiments of the present invention.

Turning to certain embodiments of the invention, FIG. 1 is a flow diagram illustrated the system of certain embodiments of the present invention. Each of the modules illustrated are aptly microfluidic components which are sized to accommodate microfluidic quantities of a sample e.g. less than about 2 ml, e.g. less than 1 ml.

Aptly, the system comprises a Radioisotope Isolation Module (RIM).

Radioisotope Isolation Module (RIM)

Aptly, the system comprises a RIM. In one embodiment, the RIM comprises an electrode trapping component to isolating and aptly concentrating a radioisotope for use in preparing a radiopharmaceutical. In some embodiments, the radioisotope is a radioactive fluoride isotope, also referred to herein as $^{18}$F-fluoride or $^{18}$F.

In some embodiments, the aqueous solution comprises $^{18}$O-enriched water. The $^{18}$O-enriched water may comprise $^{18}$F. The aqueous solution may be generated, and obtained from, a cyclotron. The cyclotron may be a miniaturised cyclotron.

In some embodiments the method comprises providing the aqueous solution at a flow rate of no greater than approximately 1 mL/min. In some embodiments the method comprises providing the aqueous solution to the RIM at a flow rate of no greater than approximately 0.5 mL/min. In some embodiments the method comprises providing the aqueous solution at a flow rate of at least 0.1 mL/min. The flow rate of the aqueous solution may be from approximately 0.1 mL/min to approximately 0.3 mL/min, for example approximately 0.2 mL/min. The total volume of aqueous solution flowed to and through the chamber may be from 0.1 to 0.5 mL, or from 0.2 to 0.4 mL, e.g. 0.3 mL.

In some embodiments, the chamber has a total volume capacity of no greater than approximately 50 µL, no greater than approximately 40 µL, no greater than approximately 30 µL, no greater than approximately 20 µL, no greater than approximately 15 µL, no greater than approximately 10 µL, or no greater than approximately 8 µL. A high ratio of the solution volume to cell volume is believed to improve the release efficiency.

The chamber may form a part of a microfluidic cell, which comprises the RIM. The RIM may be provided in an integrated microfluidic system, e.g. as part of the same microfluidic device as one or more other modules described herein. Aptly, the use of a microfluidic cell enables the manipulation of low volumes and is thus beneficial in that it generates less waste, reduces reagent costs and requires lower sample volumes compared to known batch processes. A microfluidic cell additionally enables faster response times due to short diffusion distances, small heat capacities and better process control due to the faster response of the system. A microfluidic cell may thus be particularly suited to the dose-on-demand production of radiopharmaceuticals.

In one embodiment, the first electrode may also be referred to as the working electrode. Aptly, the first electrode comes into contact with the flow of aqueous solution. The first electrode may be of any suitable shape, for example circular, ovoid, rectangular, square or triangular. Aptly, a cross sectional shape of the first electrode may be of any suitable shape, for example circular, oval, rectangular, square or triangular. Aptly, circular and rectangular electrodes have been shown to have excellent performance in both trapping and release of a radioisotope.

In some embodiments, the first electrode is formed from graphite. In some embodiments, the first electrode is formed from glass carbon. In some embodiments, the first electrode is a carbon disk. In some embodiments, the first electrode may be a carbon disk formed from a carbon rod. For example, the first electrode may be formed by slicing a thin section from a commercially available carbon rod, such as those sold by Goodfellow Cambridge Ltd. Aptly, the carbon rod is made of graphite but is hard, unlike normal graphite which is soft. Thus, in some embodiments the first electrode is not formed from standard graphite e.g. a layered graphite.

In some embodiments, the first electrode has a hardness of more than 1.0, for example more than 1.1, for example more than 1.2, for example more than 1.3, for example more than 1.4, for example more than 1.5, for example more than 1.6, for example more than 1.7, for example more than 1.8, for example more than 1.9 or for example more than 2.0 on the Mohs scale. In certain embodiments, the first electrode has a hardness of more than 2.0 on the Mohs scale e.g. 2.1, 2.2, 2.3 or greater.

SEM images have shown that, unlike soft graphite which has a layered structure, a section of carbon rod has a flat surface comprising a plurality of recesses. Thus, the first electrode may comprise an irregular surface. Aptly, this irregular surface comes into contact with the flow of aqueous solution. This surface structure of the carbon rod is believed to be favourable for trapping and release. It has also been found that, unlike soft graphite, the first electrode formed from the carbon rod is not deformed after trapping, thereby significantly increasing the performance of the electrode. Thus, in some embodiments, the first electrode is not deformed in use. In further embodiments, the first electrode is capable of retaining its original form when a voltage of at least 0.5 V, at least 1 V, at least 3 V, at least 5 V, at least 10 V or at least 15 V or at least 20V is applied across the electrodes.

In some embodiments, the carbon rod has a purity of at least 99%, at least 99.5%, at least 99.8% or at least 99.9%. The carbon rod may comprise trace amounts of other elements such as, but not limited to, Al, B, Ca, Cu, Fe, Mg, Na and/or Si. Each of these elements may be present in an amount of no greater than 1%, no greater than 0.5%, no greater than 0.1%, no greater than 0.05% or no greater than 0.01%.

A circular first electrode of the electrode trapping cell may be formed by cutting a section of a desired thickness from a carbon rod. If a non-circular electrode is required (e.g. rectangular), the section can be shaped using sand paper. The first electrode may have a polished surface layer. This polished surface layer may come into contact with the flow of aqueous solution. Polishing is thought to clean the electrode surface and reduce the emission of particulates during use which can be adversely affect the performance of the electrode. The first electrode may have a thickness of from 0.1 mm to 0.5 mm, or from about 0.2 mm to 0.3 mm, e.g. 0.25 mm.

In some embodiments, the surface area of the first electrode which comes into contact with the flow of aqueous solution is at least 10 mm$^2$, for example at least 15 mm$^2$, for example at least 20 mm$^2$, for example at least 30 mm$^2$, for example at least 40 mm$^2$, for example at least 50 mm$^2$, for example at least 60 mm$^2$ or, for example at least 70 mm$^2$. In some embodiments, the surface area of the first electrode which comes into contact with the flow of aqueous solution is no greater than 100 mm$^2$, for example no greater than 90 mm$^2$, for example no greater than 80 mm$^2$, for example no greater than 75 mm$^2$, for example no greater than 55 mm$^2$, for example no greater than 35 mm$^2$ or for example no greater than 25 mm$^2$.

The second electrode may also be referred to as the counter electrode. The second electrode may be formed from a transition metal. Suitable transition metals include for example gold, silver, iron, zinc, copper and platinum. In some embodiments, the second electrode is formed from platinum, for example platinum foil. Platinum is particularly suitable due to its electrochemical stability.

In some embodiments, the distance between the first and second electrodes is no greater than 0.5 mm. In some embodiments, the distance between the first and second electrodes is from 0.1 to 0.5 mm, for example from 0.2 mm to 0.4 mm or for example from 0.25 mm to 0.3 mm. Aptly, the smaller the gap between the electrodes, the less the resistance, allowing a relatively low voltage to be used.

In some embodiments, the first electric field is generated by applying a voltage of no greater than 50 V, no greater than 30 V or no greater than 20 V across the first and second electrodes. In some embodiments, the first electric field is generated by applying a voltage of from 5 to 20 V, for example, 10 to 20 V, e.g. from 14 to 20 V, across the electrodes. When the first electric field is generated between the electrodes, the first electrode will have a positive charge (i.e. the first electrode functions as the anode) such that negatively charged radioisotope ions present in the aqueous solution are attracted to the first electrode, causing them to be trapped on the first electrode.

In certain embodiments, the efficiency of trapping of the radioisotope on the first electrode may be at least 94%.

In some embodiments, the method comprises removing the aqueous solution from the chamber prior to providing the flow of the organic-based solution into the chamber. The organic-based solution may comprise an organic solvent. Suitable organic solvents include acetonitrile, DMF, DMSO and N-methylformamide. Because some radioisotope ions such as $^{18}$F are insoluble in organic solvents, the organic-based solution may further comprise a phase transfer reagent. In some embodiments, the phase transfer reagent is kryptofix 222 (K222). The concentration of K222 may be from 0.027 to 0.08 M.

Aptly, the organic solution further comprises a source of counter ions. Aptly, if the radioisotope ions are negatively charged, the counter ions will be positively charged. The counter ions may be alkali metal ions, such as sodium or potassium ions. In some embodiments, the organic solution comprises a source of potassium ions, such as $K_2CO_3$ or $KHCO_3$. The concentration of $K_2CO_3$ or $KHCO_3$ may be from 0.01 to 0.04 M.

In some embodiments, the organic solution further comprises from 1 to 10%, for example from 2 to 8% or from 3 to 6% $H_2O$ by volume. In some embodiments, the $H_2O$ content of the organic solution is about 4%. Aptly, a small amount of water significantly increases the solubility of the insoluble radioisotope ions in the organic-based solution, thereby facilitating the release of the radioisotope from the first electrode. A water content of greater than 10% may have a detrimental effect on subsequent reactions of the released radioisotope.

In some embodiments the organic-based solution is provided to the RIM at a flow rate of at least 0.05 mL/min. The flow rate may be from 0.05 to 1 mL/min, e.g. 0.05 to 0.5 mL/min, from 0.08 to 0.3 mL/min or from 0.1 to 0.2 mL/min. In some embodiments, the method comprises providing the aqueous solution at a higher flow rate i.e. at a greater flow rate than the flow rate that the organic-based solution is provided at.

In some embodiments the method comprises providing the organic-based solution at a flow rate of at least 1 mL/min. The flow rate may be from 0.05 to 1 mL/min, for example 0.1 to 1 mL/min.

Aptly, the aqueous solution is provided at a flow rate of approximately 0.2 mL/min and the organic-based solution at a flow rate of approximately 0.1 mL/min. The total volume of the organic-based solution provided to the chamber may be from about 0.1 to 0.5 mL, or from about 0.2 to 0.4 mL, e.g. 0.3 mL.

In some embodiments, the method further comprises washing the chamber prior to providing the flow of an organic-based solution through the chamber. The wash step may be carried out after trapping the radioisotope on the first electrode. Washing may be carried out by flowing an organic solvent, or a solution comprising an organic solvent, through the chamber. The organic solvent may be the same as that comprised within the organic-based solution which is subsequently flowed into the chamber before release of the trapped ions is effected. The washing step helps to remove residual aqueous solution from the chamber. In some embodiments, the chamber is washed with acetonitrile.

In some embodiments the second electric field is generated by applying a voltage of no greater than 20 V e.g. no greater than 10 V e.g. no greater than 5 V across the first and second electrodes. In some embodiments the second electric field is generated by applying a voltage of from about 1 to 5 V or from about 1.5 to 4.5 V (e.g. from 1.6 to 4.1 V) across the electrodes. It will be understood that the voltages described herein in relation to the second electric field may also be expressed as negative values (e.g. −10 V or −5 V), since the second electric field has an opposite polarity to the first electric field. When the second electric field is generated, the first electrode gains a negative charge (i.e. it becomes the cathode). This causes the trapped radioisotope ions to be repelled and released from the first electrode.

The trapping of radioisotope ions from an aqueous solution on an electrode, followed by release of the ions into an organic-based solution as provided by certain embodiments of the present invention thus offers a convenient method of solvent exchange which is simpler, faster and easier to automate than conventional techniques based on anion exchange and azeotropic evaporation. Thus, the RIM of the system of certain embodiment may also act to concentrate the radioisotope.

In some embodiments, the RIM e.g. comprising the electrode trapping cell described herein may be heated and therefore the system may comprise a heating element. The heater may be configured for heating the chamber, or it may be configured for heating fluid before the fluid enters the chamber. In some embodiments, the heater comprises a hot plate, a heating element or a heat mat. In some embodiments, the chamber, or the entire apparatus or microfluidic cell, is positioned on the heater. The heater may be manually or automatically operable.

Heating may be carried out prior to applying the second electric field. It has been found that heating can facilitate the release of the radioisotope from the second electrode, particularly when using small volumes of solution. The chamber and/or organic-based solution may be heated to a temperature of from 40 to 100° C., e.g. 50 to 100° C., e.g. 40 to 80° C., from 60 to 90° C. or from 70 to 80° C.

In some embodiments, the chamber may be heated indirectly. For example, where the chamber is part of an integrated system, for example as part of a microfluidic system comprised on a microfluidic chip, it may not be necessary to place the chamber directly adjacent to or in direct contact with a heat source in order to heat the chamber. Heating may be achieved indirectly through heat transfer by heating another area of the integrated system, for example by heating another area of the microfluidic chip.

In some embodiments, a microfluidic system comprises a RIM and a RPM. The RIM comprises the chamber. The RPM comprises a microreactor and/or a micromixer. Where the organic-based solution comprising the released radioisotope is for transfer from the RIM to the RPM, heating of the chamber may be achieved by heating part or all of the RPM directly. The chamber is not heated directly but is heated indirectly through heat transfer from the RPM. The RPM may comprise a reactor. The reactor may be heated directly. The RPM may comprise a mixer. The mixer may be heated directly.

The RIM may further comprise leads which connect the electrodes to a circuit.

In an alternative embodiment, the RIM comprises a monolithic body as described below. In this embodiment, the analyte is a radioisotope or cation or anion thereof and may have been produced in a cyclotron or a decay generator. The monolithic body is used to isolate the radioisotope or anion or cation thereof from the radioactive aqueous solution (e.g. the sample) produced by the cyclotron or decay generator. In some embodiments, the aqueous solution comprises $^{18}$O-enriched water. The $^{18}$O-enriched water may comprise $^{18}$F. Aptly, the monolithic body is a strong anionic exchange monolithic body.

The analyte may be radioactive isotope [$^{18}$F]fluoride, (for example $^{18}$F$^-$) or the analyte may be radioactive isotope $^{68}$Ga or cation thereof (for example $^{68}$Ga$^{3+}$). In this embodiment, separation is carried out to concentrate the radiotracer.

The RIM is aptly in fluid communication e.g. by way of a conduit or a microchannel with a Radiopharmaceutical Production Module (RPM) in use. Details of exemplary RPM are provided below.

Radioisotope Isolation Module of Certain Embodiments

Figure 4:
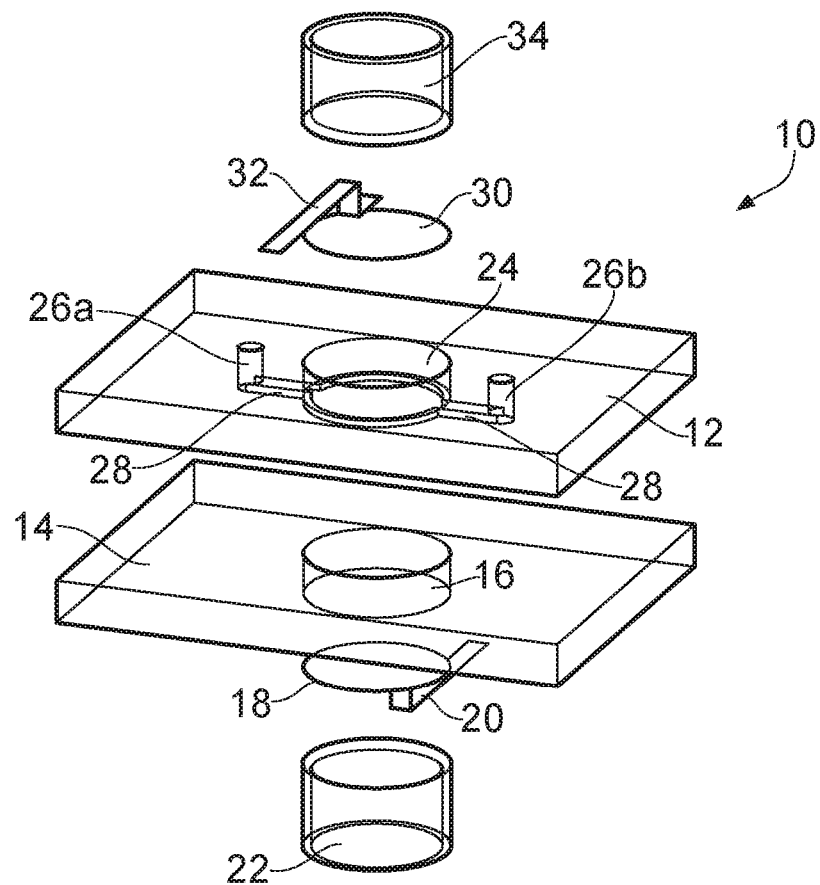
FIG. 4 illustrates an electrode trapping cell of the Radio-isotope Isolation Module (RIM) of certain embodiments of the present invention.

With reference to FIG. 4, a microfluidic cell which forms or is comprised in a RIM 10 comprises upper 12 and lower 14 rectangular glass plates, which have been machined to the desired size and shape. It will be appreciated that in alternative embodiments, the plates may be formed from other materials such as quartz or polymer. In the centre of the lower plate 14 there is a circular cut-out 16 which extends through the entire depth of the plate 14, and which receives a carbon disk (10 mm diameter) that forms the working electrode 18. The working electrode 18 is cut to size and polished. A first lead 20 connects the working electrode 18 to an electrical circuit (not shown). The working electrode 18 is secured in place by a first cylindrical glass liner 22 which is sized to fit into the cut-out 16 of the lower plate 14. The glass liner 22 may be a stock component, or it may be machined to the required shape and size.

The upper plate 12 has a circular cut-out 24 in a position corresponding to that of the cut-out 16 in the lower plate 14. The upper plate further comprises two holes 26, one either side of the cut-out 24, each of which is fluidly connected to the cut-out 26 via a channel 28. One of the holes 26a provides an inlet to allow fluids into the cell 10, while the other 26b provides an outlet. A circular platinum counter electrode 30 (10 mm diameter) is received in the cut-out 24 in the upper plate 12. The counter electrode 30 is connected to the circuit by a second lead 32. The counter electrode 30 is secured in place by a second cylindrical glass liner 34 which is sized to fit into the cut-out 24 in the upper plate 12. The glass liner 34 may be a stock component, or it may be machined to the required shape and size.

Figure 5:
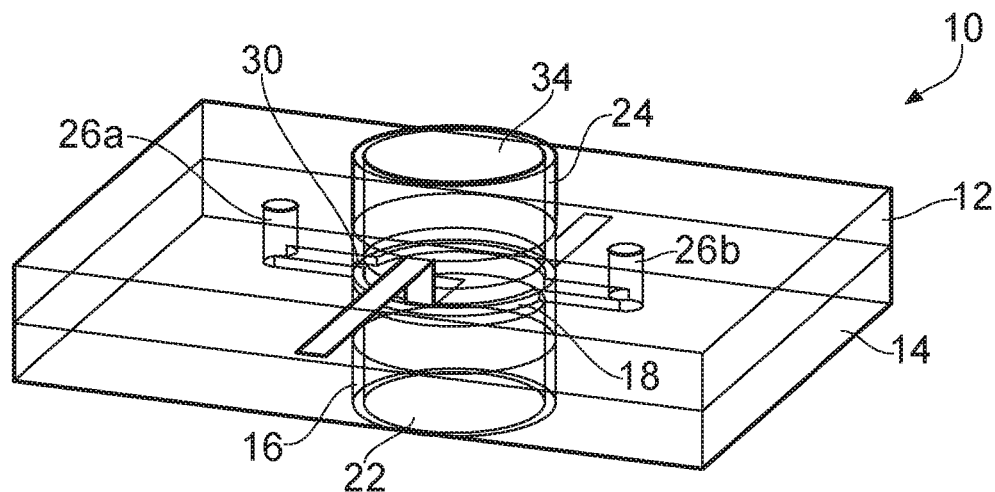
FIG. 5 illustrates an electrode trapping cell of the Radio-isotope Isolation Module (RIM) of certain embodiments of the present invention.

FIG. 5 shows the cell 10 of FIG. 4 with the components assembled. To assemble the cell, the upper and lower plates 12, 14 are aligned before being thermally bonded together. Once the plates 12, 14 are bonded the counter electrode 30 is placed within the cut-out 24 in the upper plate 12. The electrode lead 32 is inserted and a sealant is applied to the interior surface of the cut-out 24 before inserting the second glass liner 34. The sealant is allowed to set before the process is repeated for securing the working electrode 18 in the cut-out 16 in the lower plate 14.

Once assembled, the upper and lower plates 12, 14 together with the first and second glass liners 22, 34 define a chamber which houses the working electrode 18 and the counter electrode 30 in a face-to-face arrangement. The gap between the electrodes is 250 µm, and the volume of the chamber is 19.6 µL. Fluids can be flowed through the chamber via the inlet and outlet 26a, 26b.

Figure 6:
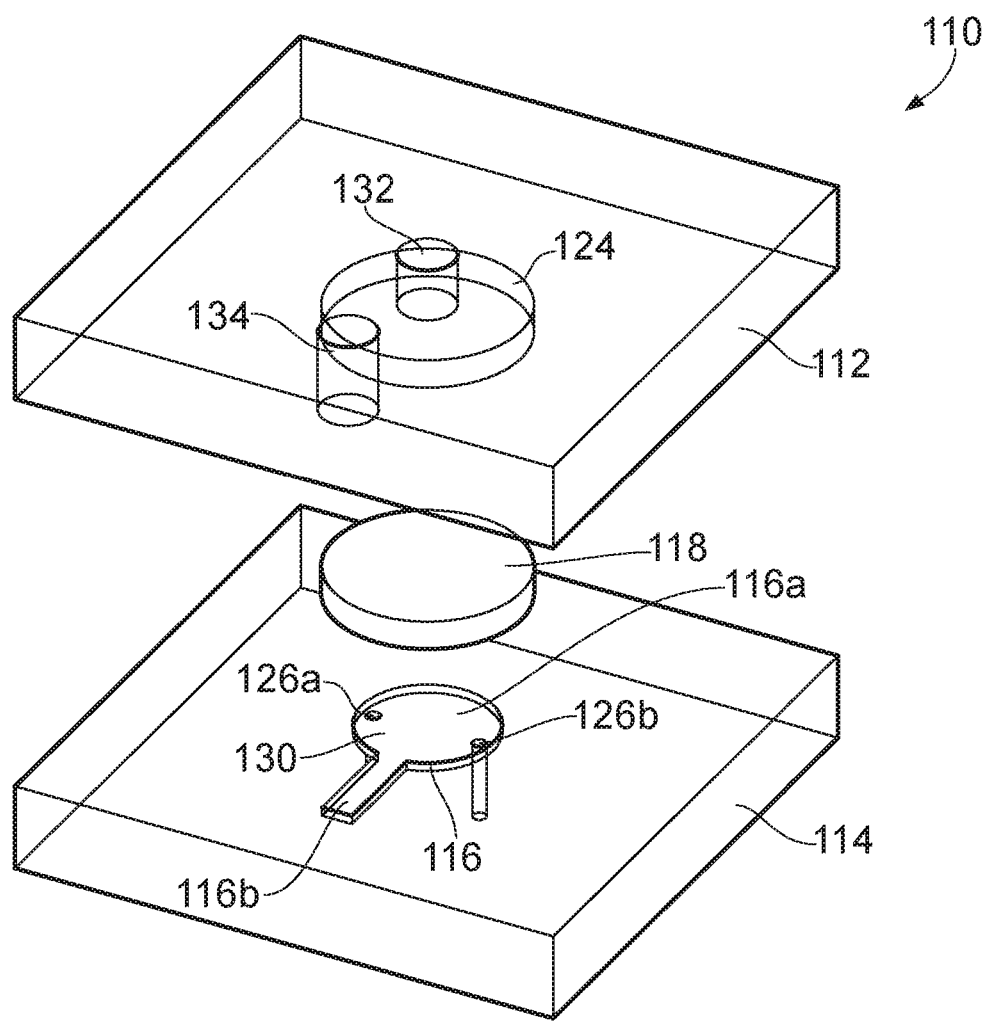
FIG. 6 illustrates an electrode trapping cell of the Radio-isotope Isolation Module (RIM) of certain embodiments of the present invention.

FIG. 6 shows an alternative embodiment of a microfluidic cell 110 comprising upper 112 and lower 114 glass plates which are substantially square. The lower plate 114 comprises a cavity 116 which provides a chamber for electrotrapping and release. The cavity 116 can be any depth or shape. In the embodiment shown, the cavity 116 is key-shaped, i.e. it comprises a circular portion 116a and an elongate portion 116b extending from the circular portion 116a. A sputter coated metallic layer formed on a surface of the cavity 116 provides the counter electrode 130. Two holes 126 extend through the lower plate 114 into the cavity 116, providing an inlet 126a and an outlet 126b for fluids.

The microfluidic cell 110 further comprises a disk-shaped working electrode 118 formed from a carbon rod. The working electrode 118 is greater in diameter than the circular portion 116a of the cavity 116 in the lower plate 114 which forms the chamber. The working electrode 118 is housed within a circular recess 124 in the upper plate 112. The upper plate 112 further comprises a first hole 132 in the approximate centre of the plate which extends into the recess 124, enabling electrical connection of the working electrode 118. A second hole 134 in the upper plate 112 is provided in a position corresponding to the elongate portion 116b of the cavity 116 in the lower plate 114, thereby enabling electrical connection with the counter electrode 130.

To assemble the cell 110, the upper plate 112, lower plate 114 and working electrode 118 are loosely assembled and the plates 112, 114 aligned before the plates 112, 114 are thermally bonded together. The electrical contacts (not shown) are then secured in the holes 132, 134 in the upper plate 112 using a sealant.

With reference to FIGS. 4-6, an embodiment of a method of radioisotope recovery (solvent exchange) by electrotrapping and release using a microfluidic cell in accordance with the present invention will now be described. The method first comprises flowing $^{18}$O-enriched water containing $^{18}$F into the chamber of the microfluidic cell 10, 110 via the inlet 26a, 126a. An electric field is generated between the electrodes 18, 118, 30, 130 by applying a voltage across the electrodes such that the negatively charged $^{18}$F ions are attracted to the working electrode 18, 118, causing them to be trapped on the working electrode 18, 118. Waste $H_2^{18}O$ is removed from the cell 10, 110 via the outlet 26b, 126b. The chamber is then washed by flowing acetonitrile through the chamber. An organic-based solution comprising K222 and $K_2CO_3$ in acetonitrile (and optionally 4% $H_2O$) is introduced into the chamber via the inlet 26a, 126a. The polarity of the electric field is then reversed, causing the $^{18}$F ions to be released from the working electrode 18, 118 into the organic-based solution. The organic-based solution containing the released $^{18}$F ions can then be removed from the chamber via the outlet 26b, 126b, and transferred to a separate reactor where the $^{18}$F ions are reacted with a precursor to generate a radiotracer. Alternatively, the precursor may be provided in the organic-based solution so that the nucleophilic substitution reaction between the precursor and the $^{18}$F ions occurs within the chamber.

Example 1

Radioisotope Isolation Module Comprising an Electrode Cell

Microfluidic RIM cells were fabricated by clamping together two glass plates, a pair of electrodes (including a platinum counter electrode) and a silicon spacer comprising a channel. Details of the cells are provided in Table 1.

The cells were tested with a low volume of $^{18}$O-water comprising $^{18}$F from an ABT cyclotron. Trapping and release efficiencies were probed at different voltages with variation of the flow rate. The results are shown in Tables 2 and 3. Efficiencies of up to 99% in trapping (Table 2) and up to 98% in release (Table 3) were observed.

TABLE 1

| Cell design | Working electrode | Cell volume (µL) |
|---|---|---|
| 1 | Graphite (15x4 mm) | 30 |
| 2 | Carbon disk (10 mm diameter) | 32 |
| 3 | Carbon disk (10 mm diameter) | 16 |
| 4 | Carbon 8x3x0.25 mm | 6 |

TABLE 2

| | Trapping conditions | | | |
|---|---|---|---|---|
| Cell design | Volume $^{18}$O-water (mL) | Flow rate (mL/min) | Voltage (V) | Trapping efficiency % |
| 1 | 0.2 | 0.2 | 20 | 99 |
| 2 | 0.3 | 0.2 | 20 | 99 |
| 3 | 0.3 | 0.2 | 15-20 | 98 |
| 4 | 0.3 | 0.2 | 14-20 | 96-99 |

TABLE 3

| | | Release conditions | | | Release |
|---|---|---|---|---|---|
| Cell design | Solvent | Volume (mL) | Flow rate (mL/min) | Voltage (V) | Temperature | efficiency % |
| 1 | Water | 0.2 | 0.1 | 1.6-3.8 | r.t. | 44-69 |
| 2 | Water-K222 | 0.3 | 0.1 | 1.6-3.8 | r.t. | 94 |
| 2 | K222-K$_2$CO$_3$ MeCN-4% H$_2$O | 0.3 | 0.1 | 1.6-3.8 | r.t. | 85 |
| 2 | K222-K$_2$CO$_3$ MeCN | 0.3 | 0.1 | 1.6-4.1 | r.t. | 73 |
| 3 | K222-K$_2$CO$_3$ MeCN-4% H$_2$O | 0.1 | 0.1 | 1.6-4.1 | r.t. | 76 |
| 3 | K222-K$_2$CO$_3$ MeCN-4% H$_2$O | 0.1 | 0.1 | 1.6-4.1 | 80° C. | 98 |
| 4 | K222-K$_2$CO$_3$ MeCN-4% H$_2$O | 0.1 | 0.1 | 1.6-4.1 | r.t. | 82 |
| 4 | K222-K$_2$CO$_3$ MeCN-4% H$_2$O | 0.1 | 0.1 | 1.6-4.1 | 80° C. | 96-98 |

In cell design 1 graphite was used as the anode (the working electrode). A trapping efficiency of 99% was achieved at 20 V within 1 minute but only 44-69% release efficiency could be obtained within 3 minutes. The low release efficiency was thought to be due to deformation of the graphite electrode. The cell was modified by replacing the graphite electrode with an electrode formed from a carbon rod (cell design 2, 3 and 3) and a significant improvement in the release efficiency was observed (Table 3). No significant difference in performance of the cells 2 and 3 was observed over more than 40 runs, demonstrating excellent stability.

Monolithic Body

In an alternative embodiment, the RIM comprises a monolithic body. The system of certain embodiments comprises one or more modules comprising a chromatographic monolithic body. Aptly, the RIM, RPM, PM and/or QCM may comprise a chromatographic monolithic body as described herein. Aptly, the monolithic body may be part of a monolithic module.

It is believed using a monolithic body may be advantageous because there is less potential for contamination of the monolithic body and thus less potential for contamination transfer from the monolithic body, and/or because there is less potential for failure of the monolithic body, for example failure as a result of leakage from or blockage in the monolithic body or microfluidic flow system, and/or because more efficient separation may be achieved. Other advantages may also be envisaged.

The methods described herein may include a process for separating an analyte from a radioactive sample which process comprises the step of:

a) eluting the sample through a chromatographic monolithic body;

wherein the monolithic body is an inorganic monolithic body and is part of a microfluidic flow system. The monolithic body may be part of a monolithic module.

The sample may be for example the first sample which is supplied from a RIM to the RPM.

Thus, the monolithic body may be utilised in one or more of the following steps:

i) concentrating a radioisotope; e.g. in the RIM;
  ii) optionally, where necessary, activating the radioisotope, for example by solvent exchange; e.g. in the RIM;
  iii) synthesizing the radiopharmaceutical, for example by labelling a non-radioactive analogue of the radiopharmaceutical with the radioisotope; e.g. in the RPM;

iv) purifying the radiopharmaceutical, e.g. in the PM; and
v) analysing the radiopharmaceutical, e.g. in the QCM;
wherein at least one of steps i), ii) iii), iv) and v) comprises a process for separating an analyte from a radioactive sample. The process for separating an analyte from a radioactive sample comprises the step of:
   a) eluting the sample through a chromatographic monolithic body;
wherein the monolithic body is an inorganic monolithic body and is part of a microfluidic flow system. The monolithic body may be part of a monolithic module.

It will be appreciated that the "monolithic body" described herein may be used not only in the RPM, but also in the RIM, PM and QCM and the following description of the monolithic body is not restricted to use in the RPM unless explicitly stated. For the avoidance of doubt "separate" as used herein means the separation or removal of an analyte from a sample, for example, for the purposes of concentration, purification, synthesis and/or analysis.

A "monolithic body" or "monolith" is a single solid structure comprising open pores which pores together form an interconnected network of channels. In one embodiment, a monolithic body is single solid structure comprising a bimodal pore structure wherein the pores comprise macropores and mesopores. In one embodiment, within the single solid structure, open macropores together form an interconnected tortuous network of channels and mesopores produce a high functional surface area. The monolithic body may be shaped in the form of a column, a tube, a rod, a disc or the like. In one embodiment the monolithic body is in the shape of a cuboid. In one embodiment, the monolithic body is in the shape of a cylinder. In one embodiment, the monolithic body comprises a silica-based composition, for example silica, for example functionalised silica. In another embodiment, the monolithic body comprises a mesoporous gel which gel may be partially or completely pyrolysed to form a ceramic material, for example the monolithic body may comprise silicon diimide mesoporous gel which is optionally partially pyrolysed to form a silicon imido nitride, or completely pyrolysed to form a silicon nitride ceramic material. A monolithic body referred to herein is inorganic. Typically the monolithic body of the invention is highly porous. Typically the monolithic body has a high surface area, for example at least 100 $m^2/g$, in particular at least 150 $m^2/g$ used and more particularly 100 to 300 e.g. 100 to 250 $m^2/g$, for example 150 to 200 $m^2/g$.

A monolithic body may be prepared using a sol-gel procedure. For example, a polymer such as PEO is added to an aqueous solution of acid, cooled and stirred. Silicon alkoxide, (for example TEOS) is added with stirring to form a transparent solution. This solution is injected into a mould and heated (40° C., 3 days) to form a wet semi-solid gel monolith. The gel is removed from the mould, washed with water and then added to ammonium hydroxide for further post-treatment (90° C., 16 hours). The monoliths are washed and dried (40° C., 1 day).

A "monolithic module" comprises one or more monolithic body/bodies hermetically sealed in a unit comprising at least one inlet and at least one outlet. The monolithic module may be adapted for incorporation into a monolithic flow system. The monolithic module may be prepared by an injection moulding process. Aptly, the monolithic body is inorganic.

A "micropore" is a pore having a pore diameter of less than 2 nm, in particular between 0.1 nm and 2 nm. A "mesopore" is a pore having a pore diameter of between 2 nm and 50 nm. A "macropore" is a pore having a pore diameter of greater than 50 nm, in particular between 50 nm and 1 micrometer.

In one embodiment, the monolithic body is inorganic and is comprised as part of a monolithic module as defined herein. A monolithic module comprises an inorganic monolithic body within an injection moulded polymer. The monolithic module comprises an inlet and an outlet.

In one embodiment, the monolithic body comprises a composition selected from a silicon based composition, an aluminium based composition and a titanium based composition, wherein each composition is optionally chemically functionalised. In particular, the composition is selected from a silica based composition, an alumina based composition and a titania based composition, wherein each composition is optionally chemically functionalised. In another embodiment, the monolithic body comprises a silicon based composition selected from silica, silicon imido nitride, silicon imide and silicon nitride, wherein each composition is optionally chemically functionalised. In particular, the monolithic body comprises silica or silica chemically functionalised. Processes for the chemical functionalization of silicon (for example silica), aluminium (for example alumina) and titanium (for example titania) based monolithic bodies are known to the person skilled in the art.

In one embodiment, the monolithic body is a cation exchange monolithic body, for example the monolithic body comprises silica modified with propyl sulfonic acid groups. In another embodiment, the monolithic body is an anion exchange monolithic body, for example the monolithic body comprises silica modified with quaternary ammonium. In another embodiment, the monolithic body is a reverse phase monolithic body, for example the monolithic body comprises silica modified with octadecyl carbon groups.

In one embodiment, the monolithic body is 10 to 80 mm in length, for example 10 to 40, e.g. 10 to 36 mm in length. In one embodiment, the monolithic body has a width of 2 mm to 6 mm, for example 3 mm to 5 mm in diameter, for example.

Example 2—Monolith Production

A mould is designed using SolidWorks software which was also used to program the CNC machine. The CNC machine was then used to mill the mould out of PTFE.

0.282 g polyethylene oxide (PEO) was added to a 50 mL falcon tube and cooled with ice. 2.54 mL nitric acid (1N) was added and the mixture stirred. 0.29 mL water was then added and the mixture left for 1 hour maintaining cooling. After 1 hour, 2.26 mL tetraethyl orthosilicate (TEOS) was added and stirring and cooling continued.

The PTFE mould in two halves was put together in a holder and heated at 40° C. for 1 hour, after which the holder was tightened to ensure no leakage. After 1 hour of stirring, the PEO/TEOS mixture was injected into the mould ensuring the mould was filled and all air escaped. A clamp with a parafilm layer was placed against the mould inlets and tightened to seal the mould and the whole apparatus heated to 40° C. for 72 hours. After this time, the clamp was removed and the two halves of the mould carefully separated.

The monolithic body formed in the mould was removed from the mould, rinsed with water and then soaked in water for 24 hours with regular replacement of the water to ensure the monolithic body was well washed. The silica-based monolith shows nanopore diameter of 16 nm, nanopore volume 0.7 $cm^3/g$, and specific surface area 209 $m^2/g$.

The monolithic body was added to a mixture of 40 ml water and 10 ml ammonium hydroxide (5M) and the mixture heated for 16 hours at 90° C. under reflux. After this time, the monolithic body was removed from the mixture and placed in water. The water was replaced regularly for the next 8 hours, after which the monolithic body was dried at 40° C. Finally the monolithic body was heated to 550° C. in a furnace for 3 hours. When cool the monolithic body was ready for use. For further details on the preparation of silica monoliths please see P. D. I. Fletcher, S. J. Haswell, P. He, S. M. Kelly, A. Mansfield, J Porous Mater. 2011, 18, 501.

2.a. Preparation of Cation-Exchange Monolithic Body

The desired amount of 3-mercaptopropyltrimethoxysilane is added to a solution containing 10 mL ethanol and 10 mL water, followed by the addition of a silica monolith. The mixture is refluxed overnight. The monolith supported thiols is recovered and washed with water to remove unreacted reagents. The obtained silica monolith is oxidized by reaction with 10 mL hydrogen peroxide (30%) in 10 mL water and 10 mL methanol overnight at 60° C. The monolith is recovered and washed with water, and treated with 10 mL of 1M $H_2SO_4$. The sulfonic acid modified monolith is washed with water and dried at 60° C. overnight. This cation-exchange monolith shows a CEC (cation exchange capacity) of 181 μeq/g.

2.b. Preparation of Anion-Exchange Monolithic Body

The desired amount of silica monolith is added to anhydrous toluene. To this is added a solution containing 0.12 mL methyltrichlorosilane and 0.3 M 3-chloropropyltrichlorosilane in anhydrous toluene. The reaction is conducted at 80° C. under nitrogen atmosphere for 24 hours. After this, the monolith is recovered and washed with dichloromethane, methanol, water and methanol to remove unreacted reagents and then dried at 60° C. overnight. Following this, the monolith is treated with N,N-dimethylethanamine in DMF at 80° C. for 24 hours to form positively charged groups on the surface of the silica monolith.

2.c. Preparation of Reverse Phase Silica Monolith

The desired amount of silica monolith is added to a solution of 1.57 mmol octadecyltrimethoxysilane in toluene. The reaction is conducted at 80° C. overnight. The monolith is recovered and washed with toluene and dried at 60° C. overnight.

For further details on the functionalization of silica monoliths please see C. S. Gill, B. A. Price, C. W. Jones, J Catal. 2007, 251, 145 or C. R. Silva, C. Airoldi, K. E. Collins, C. H. Collins, LCGL North America 2004, 22, 632.

Example 3: Synthesis of Silicon Nitride, Silicon Imido Nitride and Silicon Silicon Imide Monolithic Bodies Details for the preparation of certain silicon nitride materials can be found in WO 2006/046012 which describes a sol-gel procedure for the preparation of materials based on silicon nitride and silicon oxynitride. Monolithic bodies comprising silicon imido nitride, silicon imide and/or silicon nitride and processes for their preparation are disclosed in WO 2013/054129. Monolithic bodies comprising silicon imido nitride, silicon imide and/or silicon nitride as described herein can be prepared according to the preparation procedures described in WO 2006/046012 and WO 2013/054129.

Silicon diimide mesoporous gel is optionally partially pyrolysed to form a silicon imido nitride, or completely pyrolysed to form a silicon nitride ceramic material.

Example 4: Preparation of Monolithic Module 4.1 Preparation of Monolithic Module Using a Two Mould Process Once functionalised, the monolithic body must be hermetically sealed to ensure that, when administered, fluid flows through the monolithic body and not around the monolithic body, for example at the interface between the monolithic body and housing. This can be achieved by forming a monolithic module according to an aspect of the invention. In particular, the monolithic body may be placed in the first of two moulds with half of the monolithic body held in a recess. The monolithic body is secured in place by a protrusion at each end of the monolithic body which extends to the centre of the primary axis of the monolithic body and remains in contact during a first moulding step. Molten polymer is injected into the first mould and allowed to set forming a first module part over the monolithic body. This resulting first module part with integrated monolithic body is placed in a second mould with the module surface opposite the monolithic body and module sides held within a recess. Molten polymer is injected into this second mould over the exposed monolithic body surface and bonds to the surface of the first module part. After setting, the complete monolithic module is annealed in a furnace. Inlet and outlet holes can be moulded into the monolithic unit during the moulding process or may be machined into the monolithic module. A monolithic module prepared by this process comprises a monolithic body which is hermetically sealed except for the inlet and outlet.

4.2 Preparation of a Monolithic Module Comprising a Silicone Moulding

MDX4-4210 biomedical silicone was prepared by mixing 1 part of curing agent with 10 parts by weight of base elastomer. The mixture was then exposed to a vacuum of about 710 mm Hg for approximately 30 minutes to remove any trapped air from the silicone.

A monolithic module was prepared by moulding MDX4-4210 biomedical silicone around a monolithic body. A monolithic body was placed in a mould and positioned such that there was a distance of at least 1 mm from the surface of the monolithic body to the surface of the mould. The mould was provided with air holes to release air trapped within the uncured silicone. The mould was also provided with holes for tubing which tubing held the monolithic body in place and allowed for adjustment of the monolithic body within the mould.

The silicone mixture was added to the mould to cover the monolith and tubing within the mould and cured at 55° C. for 2 hours.

The resulting module was found to comply with leakage and stability requirements at a flow rate of 1 ml/min. Chemical compatibility was observed with acetonitrile and sodium hydroxide. No volume change was observed following immersion of the module in acetonitrile for 20 hours at 24° C. Volume changes following immersion in sodium hydroxide were observed as follows:
- +9% volume increase at 50% concentration for 7 days at 70° F.
- −2% volume increase at 20% concentration for 7 days at 70° F.
- +1.2% volume increase at 20% concentration for 3 days at 212° F.

Example 5: Use of Monolithic Body to Isolate $^{68}Ga$ in a Radioisotope Isolation Module A cation exchange monolith has been used to quantitatively trap and recover $^{68}Ga$ from a decay generator. Use of a commercial cation exchange resin has only recovered about 50% $^{68}Ga$.

An aqueous radioactive substance for example $^{68}$Ga solution is passed through a cation-exchange monolith column so that the $^{68}$Ga is trapped on the monolith. The monolith is then washed with organic based solution and the column eluted with small volume of organic based solution to release at least 95% $^{68}$Ga.

By addition of the required reagent i.e. DOTA, NOTA or DTPA to the obtained $^{68}$Ga solution, excellent labelling yield can be obtained, for example 99% for DOTA (20 μM DOTA, 95° C., 10-20 min), 99% for NOTA (100 μM NOTA, room temperature, 10 min), and 96% for DTPA (20 μM DTPA, 95° C., 20 min).

After labelling/or synthesis of radiotracer the reaction mixture then passes through a reverse phase (C18) monolithic column for purification.

Labelling/or synthesis of radiotracer is performed by adding the required reagent to the obtained solution in an RPM and then passing the reaction mixture through a reverse phase (C18) monolithic column for purification in a PM.

Example 6

Synthesis of Radiotracer [$^{18}$F]FDG Using a Monolith in a RPM and PM of the System 0.2-0.3 ml of an aqueous solution of $^{18}$F is passed through an electrode trapping cell at a flow rate of 0.2 ml/min under a constant electric potential (14-20V) applied between carbon and Pt electrodes. The cell is then flushed with anhydrous MeCN (0.5 mL/min, 1 min) while the voltage is disconnected. 0.1 ml of organic based solution containing the K222 and KHCO$_3$ in MeCN—H$_2$O (1-10%) is passed through the cell at flow rate of 0.1 ml/min under a reversed potential (2-4V) while the cell is heated to a preset temperature of 80° C. and the released solution is stored in a sample loop. The released solution containing $^{18}$F, K222 and KHCO$_3$ is pushed by MeCN at flow rate of 0.02 ml/min to mix with 0.1 ml of mannose triflate solution (0.02 ml/min) inside a Y-micromixer then together entering a microreactor (volume 0.05 ml) heated at 100° C. The reaction solution mixed with a flow of H$_2$O (0.04 ml/min) then passing through C18-monolith column for trapping the labelled precursor. The monolith is washed with water and dried with N$_2$. A 0.4 ml of 2 N NaOH solution is loaded into the monolith and hydrolysis is maintained at room temperature for 2 min and the product [$^{18}$F]FDG is eluted out with 1-5 ml of water, which is passed through cation-, anion-, silica- and C18-monoliths for purification of [$^{18}$F]FDG.

Radiopharmaceutical Production Module

Aptly, the system further comprises a Radiopharmaceutical Production Module (RPM) which is in fluid communication with the RIM in use. Aptly, the radioisotope released from the RIM is reacted with a precursor to form a radiopharmaceutical or a radiotracer or an intermediate produce in the synthesis of a radiopharmaceutical.

In some embodiments, the RPM comprises a micromixer and/or a microreactor.

The microfluidic system may further comprise a heater configured to heat all or part of the RPM. Aptly the heater may be configured to heat the micromixer and/or the microreactor. Aptly heating all or part of the RPM results in heat transfer to the chamber of the RIM. In some embodiments, the heater comprises a hot plate, a heating element or a heat mat. The heater may be manually or automatically operable.

Temperature plays an important role in the reaction rate and efficiency of chemical and electrochemical processes. Where one or more of these processes occurs within an integrated system, for example within a microfluidic system (e.g. in an integrated microfluidic chip), it may be advantageous to control and/or differentiate the temperature at which each process occurs. For example, it may be advantageous if the chamber is maintained at a temperature which is lower than that of all or part of the RPM.

Aptly, the microfluidic system may further comprise a heat reduction means. The heat reduction means operates to reduce heat transfer from the RPM to the chamber when the RPM is heated directly. In some embodiments, the heat reduction means is a slot formed in the microfluidic system (e.g. in a microfluidic chip comprising the RIM and the RPM) between the chamber and all or part of the RPM.

In some embodiments, there is a temperature difference of greater than 50° C. between the directly heated area of the RPM and the chamber, particularly when the RPM is heated to temperatures in excess of 90° C., for example to approximately 100° C.

It will be appreciated that the precursor will be selected in accordance with the desired radiotracer. The radiotracer may be any compound which is prepared by nucleophilic substitution using $^{18}$F for example. Examples of radiotracers include [$^{18}$F]-FDG, 3'-deoxy-3'-[$^{18}$F]fluorothymidine (FLT), [$^{18}$F]FMISO and $^{18}$F-sodium fluoride.

In embodiments wherein the desired radiotracer is [$^{18}$F]-FDG, the precursor is aptly mannose triflate. Suitable precursors for the preparation of other common radiolabelled substances will be known by those skilled in the art.

In some embodiments, the RPM comprises a reactor where the radioisotope is reacted with the precursor. The reactor may form a part of the same microfluidic device as the RIM or alternatively may be provided in a separate device. The reactor may comprise a mixing channel which may be for example a serpentine channel. Alternatively, the RPM may comprise a monolithic body or monolithic module as described herein.

In some embodiments, the RPM comprises a mixer where the radioisotope is mixed with the precursor. The mixture may then be transferred to the reactor where the reaction between the radioisotope and the precursor is effected, for example by heating.

Alternatively, the released radioactive isotope may be reacted with the precursor in the RIM prior to being provided to the RPM. In some embodiments, the organic-based solution may additionally comprise the precursor such that the radioisotope reacts with the precursor in the chamber upon release of the radioisotope from the first electrode.

Production of the radiopharmaceutical in the RPM may comprise additional chemical processing steps including for example hydrolysis, deprotection and/or purification. For example, in embodiments wherein the radioisotope is [$^{18}$F] fluoride and the precursor is mannose triflate, the nucleophilic substitution reaction generates acetylated [$^{18}$F]FDG which must then be hydrolysed to remove the protecting groups in order to produce the final radiotracer [$^{18}$F]-FDG. The appropriate chemical processing steps required for the synthesis of a desired radiopharmaceutical will be apparent to those skilled in the art.

In one embodiment the radiopharmaceutical is [$^{18}$F]FDG. The synthesis of [$^{18}$F]FDG is shown schematically below:

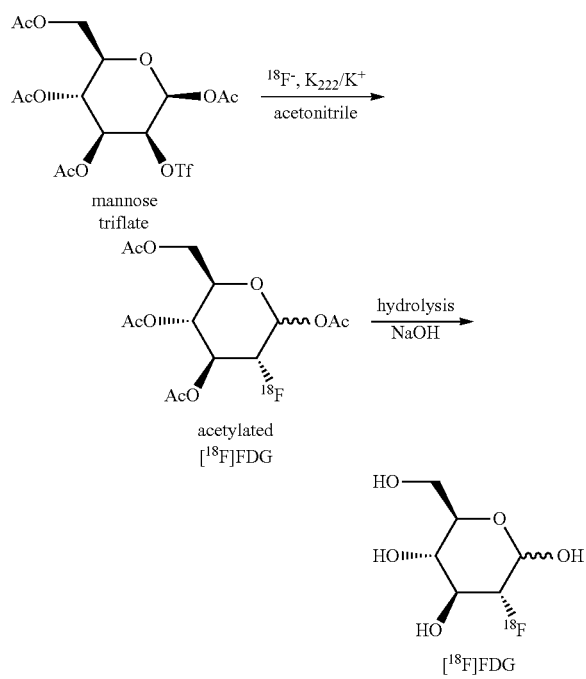

Synthesis of [$^{18}$F]FDG may follow the steps of:
1. [$^{18}$F]fluoride generation by proton bombardment of O-enriched cyclotron via a cyclotron;
2. Pre-concentration of aqueous [$^{18}$F]fluoride, for example using an ion exchange column, using a monolithic body or by electrochemical trapping.
3. Release of [$^{18}$F]fluoride in acetonitrile containing addition of phase transfer catalyst (typically Kryptofix 2.2.2) and potassium carbonate.
4. Radiolabelling reaction of mannose triflate with [$^{18}$F] fluoride via $S_N2$ nucleophilic substitution, producing the acetylated form of [$^{18}$F]FDG (i.e. unhydrolysed [$^{18}$F]FDG).
5. Solvent exchange from acetonitrile to water.
6. Hydrolysis of acetylated-[$^{18}$F]FDG to [$^{18}$F]FDG, either by acid hydrolysis (HCl) or base hydrolysis (NaOH).
7. Purification of the crude [$^{18}$F]FDG mixture, e.g. via solid-phase extraction (SPE), for example using a monolithic body.
8. Formulation of the [$^{18}$F]FDG dose as an isotonic saline (sodium chloride) solution.

Example 7—Synthesis of [$^{18}$F]-FDG

A system similar to that shown in FIG. 2 which is described in more detail below was fabricated and used to synthesise [$^{18}$F]-FDG in accordance with the following method. 0.2-0.3 mL of $^{18}$O-enriched H$_2$O containing $^{18}$F was passed through the cell at a flow rate of 0.2 mL/min under a constant electric potential (14-20 V) applied between the carbon and Pt electrodes. The cell was then washed by flushing with anhydrous MeCN (0.5 mL/min, 1 minute) while the voltage was disconnected. Next, 0.1 mL of organic-based solution containing K222 and KHCO$_3$ in MeCN—H$_2$O (1-10%) was passed through the cell at flow rate of 0.1 mL/min under a reversed potential (2-4 V). The cell was heated to a pre-set temperature of 80° C. and the released solution was stored in a sample loop. The released solution containing $^{18}$F, K222 and KHCO$_3$ was pushed by MeCN at flow rate of 0.02 mL/min to mix with 0.1 mL of mannose triflate solution (0.02 mL/min) inside a Y-micromixer. The mixture was then transferred to a microreactor (volume 0.05 mL) heated to 100° C. The reaction solution was mixed with H$_2$O at a flow rate of 0.04 mL/min and then passed through a C18-monolith column for trapping the labelled precursor. The monolith was washed with water and dried with N$_2$. 0.4 mL of 2 N NaOH solution was loaded into the monolith and hydrolysis was maintained at room temperature for 2 minutes. The product [$^{18}$F]-FDG was eluted out with 1-5 mL of water.

Using this system, $^{18}$F fluoride (initial activity up to 30 mCi) was trapped with an efficiency of 94-99% and subsequently released with a release efficiency of 90-95%. After basic hydrolysis on the deprotection column 98.3% [$^{18}$F]-FDG was obtained. Optionally, the [$^{18}$F]-FDG can be further purified by passing through cation-, anion-, silica- and C18-monoliths.

FIG. 16a shows a top view of a microfluidic system 600 for the preparation of a radiotracer. In the embodiment shown, the system comprises a microfluidic cell 610 comprising a chamber 611 for solvent exchange of $^{18}$F by electro-trapping and release. Adjacent to the microfluidic cell is valve 630. The system further comprises a microfluidic reactor 620. Area 621 of the microfluidic reactor is heated directly by means of a heater (not shown) positioned directly below area 621. Heat reduction mean is provided in the form of a slot 640. The slot reduces heat transfer from the directly heated area (621) to the chamber of the microfluidic cell.

FIG. 16b is a graphical representation of the temperature difference between area 621 and microfluidic cell 610 as measured by an infrared thermometer following direct heating of area 621.

The use of microfluidic cells for processing of low volume of heavy water feed from the cyclotron offers an excellent method for solvent exchange to carry out nucleophilic substitution reactions with standard precursors. In addition to the excellent trap and release performance, the benefits of the invention include the use of a low voltage, re-use of electrodes and simple operation. The present invention thus offers significant potential in efficient dose-on-demand radiotracer production.

Purification Module (PM)

The Purification Module (PM) may be in fluid communication with the RPM in use e.g. via a microchannel or conduit. The PM may be composed in the same microfluidic device as the RPM and one or more further modules or may be a separate component.

The Purification Module (PM) is configured to remove impurities and residual solvents from the radiopharmaceutical produced in the RPM. Aptly, the Purification Module comprises one or more High Performance Liquid Chromatography columns. Alternatively, the PM comprises one or more chromatographic monolithic bodies as described herein. Aptly, the monolithic body is comprised in a monolithic module.

Therefore in one embodiment, the analyte is an impurity and the sample is a solution of radiopharmaceutical generated by the RPM. Separation is carried out to purify the radiotracer (step iv, above).

Aptly, the table below illustrates the type of monolithic body which may be used to separate certain impurities;

| Type of resin | Removal of: |
| --- | --- |
| Cation (+ve ion) exchange | Cationic impurities Kryptofix 2.2.2 Metal radionuclides NaOH (neutralisation) |
| Anion (–ve ion) exchange | Anionic impurities Complexed metal radionuclides HCl (neutralisation) |
| Normal phase (alumina) | Polar impurities [$^{18}$F] fluoride Bacterial endotoxins |
| Reversed phase | Non-polar impurities Acetylated-[$^{18}$F]FDG Acetylated-[$^{18}$F]FDM Acetylated-CIDG Kryptofix 2.2.2 |

For example, the analyte is an impurity selected from [$^{18}$F]fluoride and endotoxin. The monolithic body used herein is, for example, a normal phase monolithic body (for example comprising alumina or silica). For example, the analyte is an impurity selected from acetylated [$^{18}$F]FDG, acetylated [$^{18}$F]FDM, mannose triflate and K222. The monolithic body used herein may be a reverse phase monolithic body (for example comprising silica modified with octadecyl carbon, (C18 or C18 monolithic body)). For example, the analyte is an impurity selected from K222 and sodium hydroxide. The monolithic body used herein may be a cation exchange monolithic body (for example silica modified with propyl sulfonic acid groups). For example, the analyte is an impurity selected from hydrochloric acid. The monolithic body as used herein may be an anion exchange monolithic body (for example silica modified with quaternary ammonium).

In one embodiment, the analyte is selected from [$^{18}$F] fluoride, [$^{18}$F]acetylated-FDG and [$^{18}$F]FDG. The monolithic body used herein may be a normal phase monolithic body (for example comprising alumina or silica) For example, the analyte may comprises analyte components [$^{18}$F]fluoride, [$^{18}$F]acetylated-FDG and [$^{18}$F]FDG and the analyte components are separated from each other by the monolithic body. The mobile phase may comprise acetonitrile and water, for example in a ratio of acetonitrile:water of for example 90:10 to 95:5, for example 90:10 or 95:5.

In one embodiment, the analyte is selected from mannose, glucose, [$^{18}$F]FDG, [$^{18}$F]FDM and CIDG. The monolithic body used herein may be a strong anion exchange (SAX) monolithic body. For example, the analyte comprises analyte components [$^{18}$F]FDG, [$^{18}$F]FDM and [$^{18}$F]FDG and the analyte components are separated from each other by the monolithic body. The sample may comprise one or more component selected from [$^{18}$F]FDG, [$^{18}$F]FDM, [$^{18}$F]FDG, acetonitrile and water. The mobile phase may comprise sodium hydroxide, for example, 20 to 200 mM, for example 20 to 100 mM, for example 50 mM.

Quality Control Module

The system aptly comprises a Quality Control Module which is for determining one or more characteristics of a sample comprising a radiopharmaceutical obtained from the Purification Module.

FIG. 7 comprises a table which lists certain criteria specified by the British Pharmacopoeia 2012 that must be satisfied for an exemplary radiotracer ([$^{18}$F]FDG). It will be understood by the person skilled in the art that embodiments of the present invention are not limited to the testing of [$^{18}$F]FDG. For example, certain embodiments of the present invention relate to devices, systems and methods which perform quality control testing of other radiotracers and/or other compounds which are for in vivo administration. In certain embodiments of the present invention, the devices, systems and methods are for use to determine at least one characteristic of a pharmaceutical compound.

In one embodiment, following purification, QC tests are performed on a sample of [$^{18}$F]FDG in order to ensure that all impurities have been removed and that the properties of the dose are suitable for injection. As used herein, the terms "[$^{18}$F]FDG" and "FDG" are interchangeable and relate to the compound 2-[$^{18}$F]fluoro-2-deoxy-D-glucose. A summary of the process for preparing [$^{18}$F]FDG is described above.

Prior to administration to a patient, the batch of [$^{18}$F]FDG has to undergo a number of quality control tests to ensure it meets the necessary safety requirements. Aptly, certain embodiments of the present invention provide a microfluidic system which can be used to perform the quality control tests of microfluidic quantities of a compound, e.g. [$^{18}$F]FDG. Certain embodiments of the present invention provide a measurement value which can be used to determine the characteristic of the sample. The measurement value can then be compared to a predetermined corresponding criterion value to determine whether the sample is suitable for administration to a patient. The predetermined corresponding criterion value can be identified using known literature such as for example although not limited to the current British Pharmacopeia, European Pharmacopoeia, International Pharmacopoeia, US Pharmacopeia and the like.

Aptly, certain embodiments of the present invention test the "appearance" and/or clarity of a sample comprising [$^{18}$F]FDG. In the BP, it is stated that the appearance of an [$^{18}$F]FDG should be a "clear, colourless or slightly yellow solution". However, it is generally considered that a slightly yellow solution is likely to contain impurities. Furthermore, other pharmacopoeias state that [$^{18}$F]FDG should be "colourless and free from particulate matter". Thus, it is often proposed that an [$^{18}$F]FDG solution should be clear, colourless, and free from particulate matter. Certain embodiments of the present invention determine the appearance of a compound for in vivo use e.g. a radiopharmaceutical and aptly determine if the radiopharmaceutical is suitable for administration.

In addition, the sample should be tested for the presence and amount of chemical impurities. In terms of chemical purity testing, CIDG refers to 2-chloro-2-deoxy-D-glucose, an impurity that can be present particularly when using acid hydrolysis in which a chloride atom takes the place of the [$^{18}$F]fluoride label. A further source of chloride may be an anion exchange cartridge used to pre-concentrate the [$^{18}$F] fluoride label in many systems, depending on the counter ion present on the cartridge resin.

Aptly, ACY-[$^{18}$F]FDG or alternatively ACY-FDG refers to the acetylated/unhydrolysed form of [$^{18}$F]FDG, which is 2-[$^{18}$F]fluoro-1,3,4,6-tetra-O-acetyl-D-glucose (also referred to as [$^{18}$F]TAG), while partially hydrolysed ACY-[$^{18}$F]FDG can also be present.

[$^{18}$F]FDM is 2-[$^{18}$F]fluoro-2-deoxy-D-mannose, a byproduct that can be produced during the [$^{18}$F]FDG synthesis process, and which can also be present in fully or partially hydrolysed form (ACY-[$^{18}$F]FDM).

Aptly, certain embodiments of the present invention determine the presence and/or quantity of impurities in the sample. In one embodiment, the chip, system and/or method may be used to determine the presence and/or quantity of residual solvents in the sample.

In one embodiment, the sample may comprise acetonitrile and/or ethanol. Aptly, the apparatus, systems and methods described herein may be used to determine the presence and/or quantity of acetonitrile and/or ethanol in the sample.

Acetonitrile is used as the solvent during [$^{18}$F]fluoride labelling. Ethanol is often used for cleaning systems and for conditioning of purification columns. Acetonitrile and ethanol concentrations must be <410 ppm and <5000 ppm respectively according to the British Pharmacopoeia (BP) and European Pharmacopoeia (EP).

In one embodiment, other impurities may be determined by the chip, system and/or method. Aptly, the impurity is a solvent. Aptly, the impurity is selected from diethyl ether, acetone and methanol. The method may also detect the presence and/or concentration of [$^{18}$F]fluoride and/or glucose.

pH

According to the BP, the pH of a dose of a compound for in vivo use, e.g. a [$^{18}$F]FDG dose should be in the range of 4.5 to 8.5, although this range can vary in other pharmacopoeias (e.g. pH 4.5 to 7.5 in the USP).

Kryptofix 2.2.2

The aminopolyether, Kryptofix 2.2.2 (4,7,13,16,21,24-hexaoxa-1,10-diazabicyclo[8.8.8] hexacosane), also known as cryptand 2.2.2, is a phase transfer catalyst used during [$^{18}$F]FDG synthesis. It incorporates a potassium ion into its cage-like structure, preventing the formation of potassium [F]fluoride in acetonitrile and thus leaving the [F]fluoride ion to react with the mannose triflate molecule by nucleophilic substitution. However, while an important aspect of the synthesis, Kryptofix 2.2.2, hereafter referred to as K222, is also very toxic, causing apnoea, ptosis and convulsions in patients, while the intravenous $LD_{50}$ in rats is 35 mg/kg. Thus, its removal from [$^{18}$F]FDG is important and its concentration in a dose must be determined.

The limit of K222 that can be present in [$^{18}$F]FDG depends varies between pharmacopoeias, with the EP and BP stating a limit of 2.2 mg per volume of dose (e.g. the maximum amount of K222 that could be in a 10 mL dose would be 2.2 mg, which would be equivalent to 220 µg mL$^{-1}$), while in the USP the limit is set at 50 µg mL$^{-1}$. Furthermore, K222 is essential for many radiolabelling processes involving [$^{18}$F]fluoride, and so is not limited to only [$^{18}$F]FDG.

While Kryptofix 2.2.2, referred to as "aminopolyether" in the BP, is usually the phase transfer catalyst of choice in the synthesis of [$^{18}$F]FDG by nucleophilic substitution, other catalysts such as tetrabutylammonium and 4-(4-methylpiperidin-1-yl)pyridine can also be employed instead, hence their inclusion in the BP. However, it is worth noting that the BP states that specific tests do not need to be performed if there is no source of the potential impurity (e.g. the test for tetrabutylammonium is not required if Kryptofix 2.2.2 is used as the phase transfer catalyst).

Bacterial Endotoxin

In the case of [$^{18}$F]FDG and other radiopharmaceuticals, the presence and/or quantity of bacterial endotoxin must be determined prior to the radiopharmaceutical being deemed safe for administration to a patient. Bacterial endotoxins can be introduced into the radiopharmaceutical manufacturing process by way of for example non sterile tubing, containers, chemicals and/or water.

Each of the above mentioned characteristics can be determined using certain embodiments of the present invention. Once the characteristics of the sample have been determined, a decision can be made as to whether or not the compound is suitable for in vivo use. In certain embodiments of the present invention, the sample has a volume which is only a small percentage greater than a single unit dose of the compound. Thus, a single unit dose of the sample comprising the compound exits the chip and is suitable for administration to a patient, providing all of the sample's characteristics meet the stated requirements for in vivo use.

Aptly, the QCM is comprised in or comprises a microfluidic chip. Aptly, the chip is prepared using photolithography and wet etching procedures. Furthermore, an integrated microfluidic devices comprising one or more modules as described herein may also be formed using these techniques. Aptly, glass wafers featuring a chromium layer and a photoresist layer are exposed to UV light through a photomask featuring a channel design. The region of photoresist exposed to light becomes soluble in photodeveloper solution, which is then used to strip away the exposed region, revealing the channel design on the chromium layer. The exposed chromium is then etched away, leaving the channel design visible on the glass. A solution of 1% hydrofluoric acid can then used to etch the channel design into the glass, after which access holes can be drilled into the glass. The remaining photoresist and chromium layers are then removed. The plate is then thoroughly cleaned and has an upper planar structure aligned with it. Both plates are placed in a furnace with a steel weight on top, and left for 4 hours at approximately 585° C. to allow the plates to thermally bond.

In certain embodiments the microfluidic device comprises three layers fabricated in glass (B270 coated with chromium and photoresist layers, Telic, USA) using the standard photolithography and wet etching procedures described above.

In embodiments which comprise a detection channel as described herein, the detection channel is formed by way of a hole being drilled into a middle or intermediate plate. Once the photoresist and chromium layers are removed, the three plates are washed thoroughly and then carefully aligned to match up (i) any inlet holes with the serpentine channel inlets, (ii) herringbone structures (if present) with the serpentine channel, (iii) the one or more detection channel (in the middle plate) with an outlet channel on the lower plate. They are then taped together and placed in the furnace at a temperature of approximately 585° C. for 4 h to thermally bond all three plates together.

In one embodiment the upper and the lower planar structures are 1 mm thick and approximately 30 mm by 30 mm. Other dimensions are encompassed by embodiments of the present invention. In one embodiment, the intermediate planar structure 106 has a thickness of between approximately 2 mm to 5 mm. Aptly, the intermediate planar structure has a thickness of between 2 mm to 4.5 mm. Aptly, the intermediate planar structure has a thickness of between 3 mm to 4 mm.

Microfluidic chips of other dimensions are also envisaged and encompassed by embodiments of the present invention.

The total volume capacity of the chip may vary depending on its use. In certain embodiments, the total volume capacity of the chip may be less than 2 ml. Aptly, the chip has a total fluid volume capacity of no more than about 500 µL. Aptly, the chip has a total fluid volume capacity of 200 µL or less. In one embodiment, the chip has a total fluid volume capacity of 75 µL or less, e.g. 70 µL or less, 60 µL or less or 50 µL or less. In certain embodiments of the present invention, the chip may have a total volume of 10 µL or less e.g. 5 µL or less. In certain embodiments, the chip has a total fluid volume capacity of less than 2 µL. Aptly, the chip is a microfluidic flow device and/or is part of a microfluidic flow device.

Each of the planar structures is made from a material through which light may be transmitted. For example, each planar structure may be formed from glass, plastic, cyclic olefin polymer (COP), quartz or a combination of these materials. In one embodiment, the planar structure is formed from glass.

Figure 8:
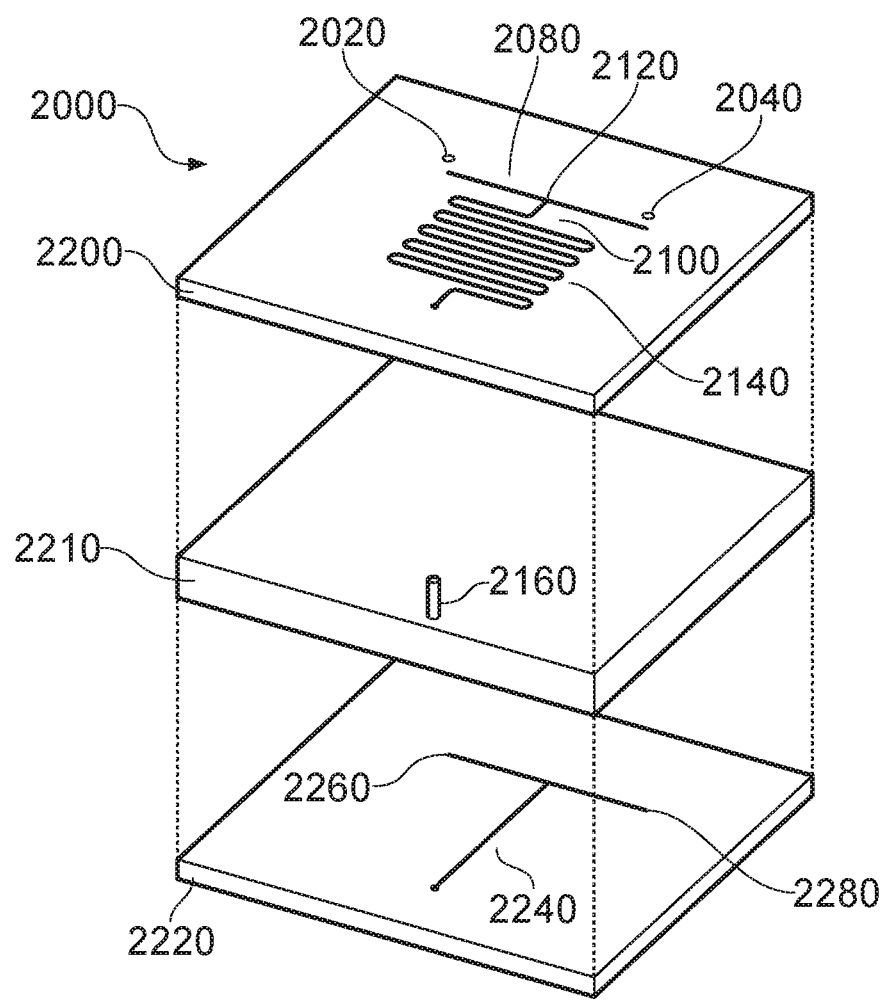
FIG. 8 illustrates a microfluidic chip comprising a Quality Control Module of certain embodiments of the present invention.

FIG. 8 illustrates a microfluidic chip 2000 which may form part of a QCM of the system. The microfluidic chip 2000 comprises an inlet port 2020 for a sample to be supplied to the chip. The inlet port 202 is provided on an upper surface 2040 of the chip. The upper surface may be provided by an upper planar structure in a layered chip as described above. In alternative embodiments, the chip may be formed from a single component and therefore only has a single layer. Such chips may be formed by techniques known in the art such as, for example, laser ablation, stereolithography and 3D printing.

The microfluidic chip 2000 also comprises a second inlet port 2060. The second inlet port can be used to introduce one or more reagents to the chip. The second inlet port 2060 is in fluid communication with the first inlet port via a first microchannel 2080. The microchannel 2080 is connected to a further microchannel 2100. In the illustrated embodiment the further microchannel 2100 is connected to the first microchannel at a junction 2120 which is generally at a midpoint of the first microchannel between the first inlet port and the second inlet port.

The further microchannel 2100 comprises a serpentine pathway portion 2140 in which the reagent and the sample mix prior to detection taking place. Thus, the further microchannel may be referred to as a mixing microchannel.

The mixing channel is connected to a detection channel 2160 which is provided at approximately right angles to the mixing channel at least partially through the thickness of the chip. The detection channel is provided as a bore in an intermediate planar structure 2210 positioned between an upper plate 2200 and a lower plate 2220.

The lower plate 2220 is provided with a T-shaped microchannel 2240 which is in fluid communication with an outlet 2260 for the sample/reagent mixture to be removed from the chip. In the illustrated embodiment, the chip comprises two outlets. In alternative embodiments, the chip may comprise a single outlet and the microchannel 2240 may be linear or L-shaped accordingly.

The chip, or a system comprising the chip, may also comprise one or more driving elements (not shown) such as for example syringe pumps to move the reagent and the sample from the respective inlet ports into the first microchannel. The driving elements may then be used to force the reagent and the sample into the mixing channel. In one embodiment, the sample and the reagent move along the first microchannel at substantially the same speed such that the fluids meet at the junction 2120.

In one embodiment, the driving elements force the mixture of the sample and the analyte along the detection channel and subsequently along the microchannel 2240 before exiting the chip via the outlet 2260 or the outlet 2280.

In use, the detection channel 2160 provides a path length between a source, e.g. a light source and a detector. The source may be positioned adjacent to or in contact with a first surface e.g. the upper surface of the chip in a position which is aligned with a long axis of the detection channel i.e. in a direction through the thickness of the chip.

The source may be a light source. In certain embodiments, the detector and/or the source is a potentiostat.

In certain embodiments, the system comprises a plurality of sources, for example, a potentiostat and one or more light sources.

In an embodiment, the system comprises a plurality of detectors, for example, a UV-visible light spectrometer, a visible/near infrared spectrometer, a Raman spectrometer and/or a potentiostat.

The light source may be connected to e.g. a fibre optic cable which is connected or is adjacent to a surface of the microfluidic chip.

The detector or a connecting element, e.g. a fibre optic cable, may be connected to or positioned adjacent to an opposing surface of the microfluidic chip to the light source. The detector or connecting element is aligned with the long axis of the detection channel and is therefore aligned with the light source. In some embodiments, the detector is provided at the same side of the chip as the source.

In use, an analyte e.g. a sample or a mixture comprising the sample or portion thereof provided in the path length may absorb some of the light provided by the source, thus meaning that the signal that reaches the detector e.g. a spectrometer will differ.

Each end of the detection channel is closed and therefore the upper surface and the lower surface of the chip which is provided immediately above and below the ends of the detection channel are composed of a material which permits transmission from the source to the detector. In one embodiment, the material is capable of transmitting UV-visible light and/or visible/near infrared from a light source to the detector e.g. a UV-visible spectrometer or a visible/near infrared spectrometer. Thus, in one embodiment, the chip is formed at least in part from an optically transparent material.

A chip which comprises a detection channel as described herein can be used to determine one or more characteristics of a compound. As described above, the detection channel provides a path length between a source and a detector and therefore characteristics which can be detected and/or measured by way of measuring e.g. absorbance. In certain embodiments, determining the characteristic of the compound involves analysing values of the characteristic at a particular wavelength.

A characteristic of the sample which can be determined using the microfluidic chip according to certain embodiments of the present invention is pH. pH can be detected using UV-visible spectroscopy or visible-near infrared spectroscopy. In one embodiment, the detector detects visible light.

Figure 9A:
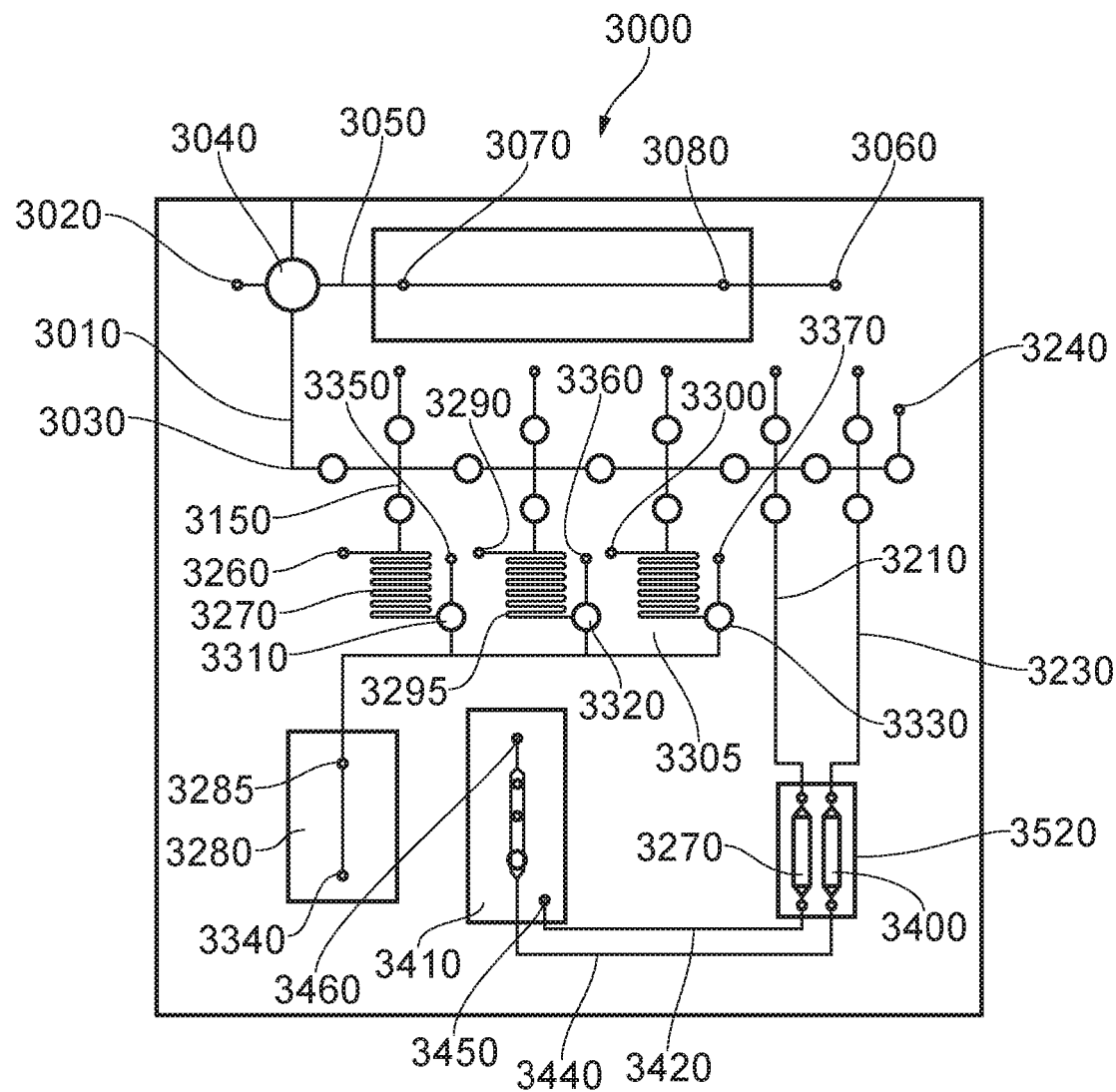
FIG. 9a illustrates a microfluidic chip comprising a Quality Control Module of certain embodiments of the present invention.
Figure 9B:
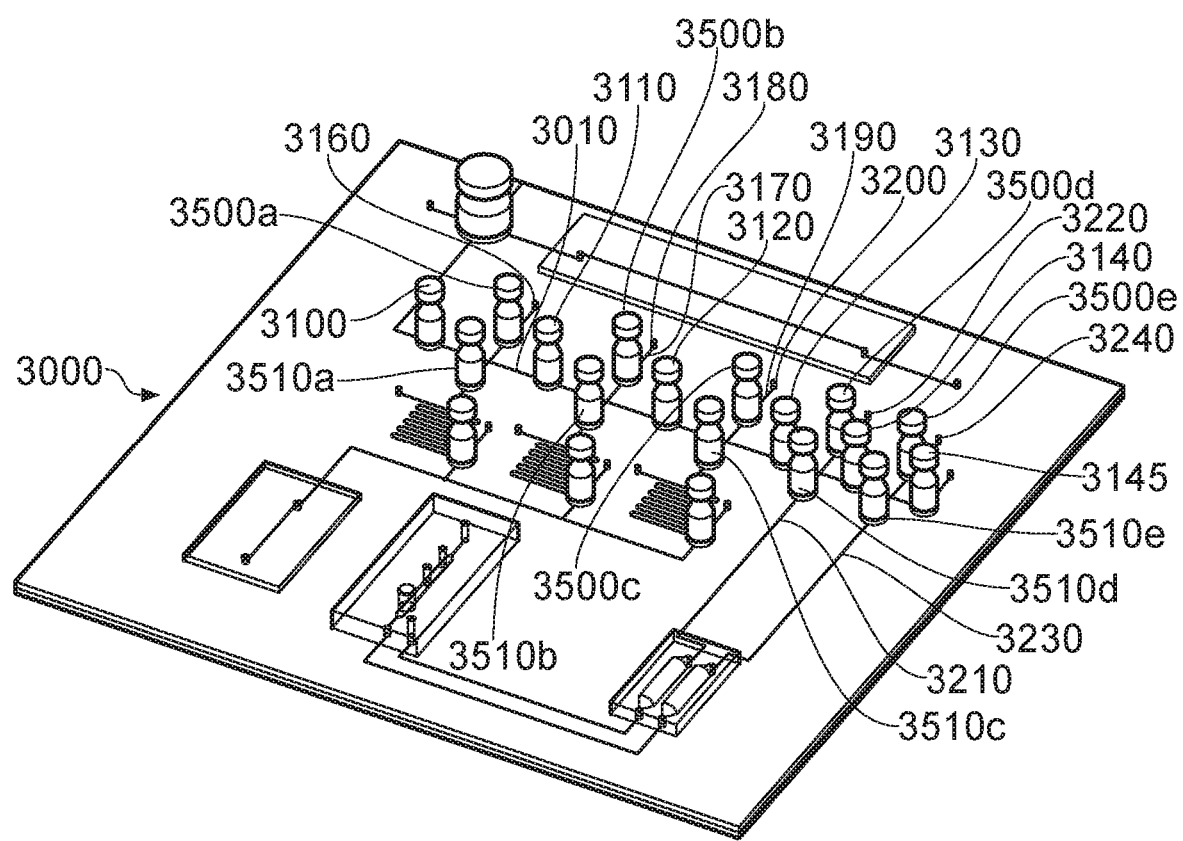
FIG. 9b illustrates an alternative view of the microfluidic chip comprising a Quality Control Module of certain embodiments of the present invention.

An alternative embodiment of the QCM is shown in FIG. 9. The microfluidic chip 3000 of FIG. 9 includes a first microchannel 3010 which is in fluid communication with an inlet port 3020. A sample fluid can be introduced into the microfluidic chip through the inlet port 3020.

The microfluidic chip may comprise a layered structure as described above. That is to say, the chip may include three layers formed from an upper planar structure, a lower planar structure (not shown) and an intermediate planar structure (not shown) which is positioned between the upper and the lower planar structures. The layers may be adhered or otherwise secured to each other in a fluid sealing way as described above.

The first microchannel 3010 comprises a first valve element 3040 which can control movement of a fluid e.g. the sample into the first microchannel.

The chip illustrated in FIG. 9 comprises an additional microchannel 3050, referred to as a sample channel. The sample channel is in fluid communication with the sample inlet port. The sample channel intersects the first microchannel. The first valve element may be a multidirectional valve which controls movement of the sample either to the sample channel or the first microchannel depending on the requirement of the user.

The sample channel is in fluid communication with an outlet 3060. Aptly, the sample channel is not connected to any further inlets. As such, no reagents are added to the sample in the sample channel and the sample may be suitable for administration to a patient in need thereof. Whether the sample is administered will be dependent on the outcome of the one or more tests carried out by the system of embodiments of the present invention and determination of the characteristics of the sample.

The sample channel may be in fluid communication with one or more detection channels as described herein. A first detection channel 3070 is provided which can be used to determine a characteristic such as for example clarity and/or appearance of the sample. A second detection channel 3080 may be provided downstream from the first detection channel.

Aptly, the first detection channel and the second detection channel may be in fluid communication via a portion of the sample channel which is provided in the lower planar structure. Thus, in use, a sample or portion thereof is flowed along the sample channel, down the first detection channel, along the sample channel in the lower planar structure and then upwardly along the second detection channel. The sample then exits via the outlet 3060.

Aptly, the first microchannel comprises a plurality of valve elements which can be used to direct flow of the sample and/or reagents and/or solutions from the first microchannel to other areas of the microfluidic chip. In addition the valve elements can be used to isolate portions of a fluid in the first microchannel from other areas of the first microchannel. Aptly, the valve elements are provided in series.

Thus, the first microchannel 3010 may comprise a second valve element 3100, a third valve element 3110, a fourth valve element 3120, a fifth valve element 3130, a sixth valve element 3140 and a seventh valve element 3145. Ultimately, the number of valve elements may depend on how many tests are to be provided on the chip and thus how many detection zones portions of the sample are to be directed to. The first microchannel may comprise a component 3600 for applying negative pressure to draw the sample through the first microchannel.

The first microchannel may comprise an approximately 90 degree change in direction (3030) between the first valve element and the second valve element. A first intersecting channel 3150 may be provided on the chip. The first intersecting channel 3150 is in fluid communication with a further inlet, referred to herein as the second inlet port 3160. The first intersecting channel intersects the first microchannel at a junction between the second valve element 3100 and the third valve element 3110.

As described herein, each intersecting channel may be provided with a pair of valve elements which prevent flow of fluid from the detection zones during filling of the first microchannel with the sample. Aptly, one of the pair of valve elements is provided in the intersecting channel upstream of the junction between the intersecting channel and one of the pair is provided downstream from the junction. The valve elements, indicated by 3500*a*, 3500*b*, 3500*c*, 3500*d*, 3500*e* and 3510*a*, 3510*b*, 3510*c*, 3510*d* and 3510*e* are placed in a closed position when the first microchannel is filled with the sample. Once flow of the sample or portion thereof to a detection zone is desired, the valves of the intersecting channel can be opened to provide a fluid flow path to the detection zone.

Figure 10:
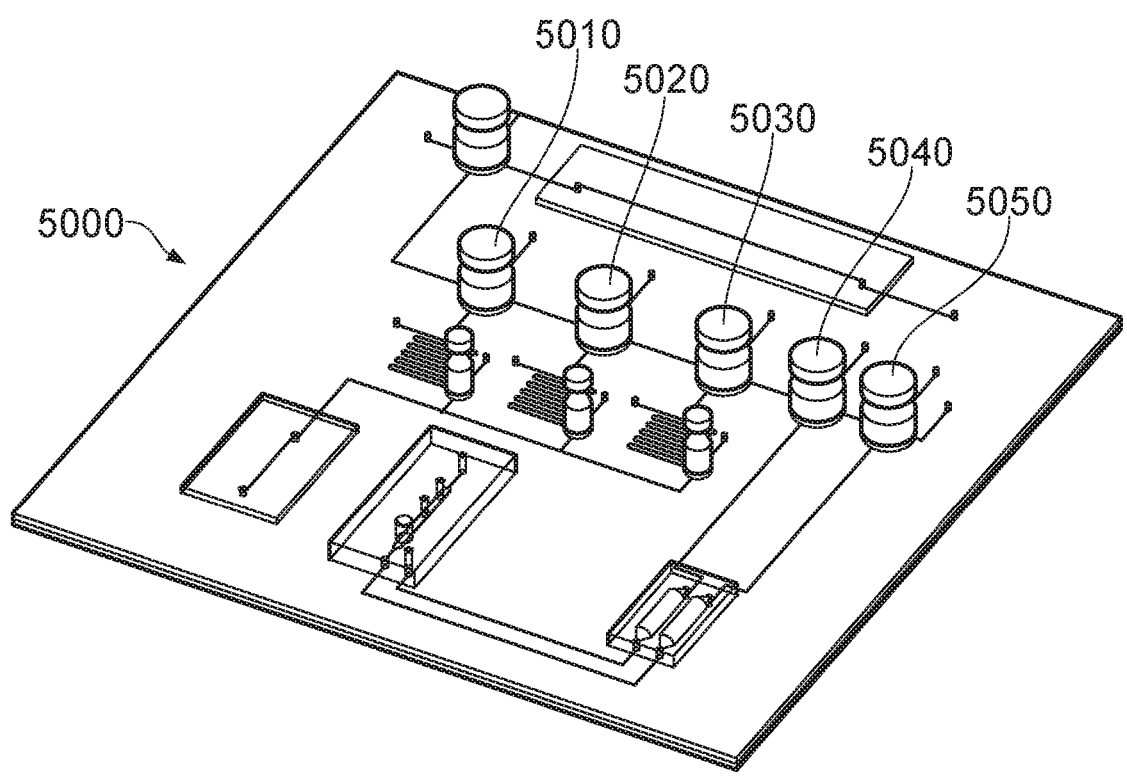
FIG. 10 illustrates a microfluidic chip comprising a Quality Control Module of certain embodiments of the present invention.
Figure 11:
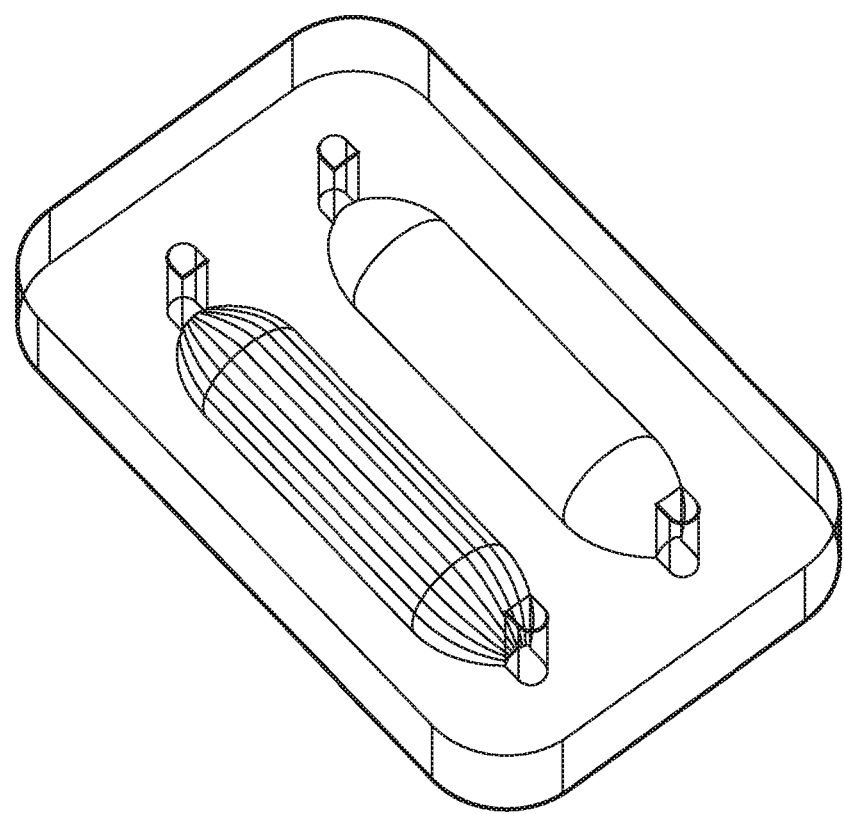
FIG. 11 illustrates a pair of chromatographic monolithic bodies comprised in a module according to certain embodiments of the present invention.

It will be appreciated that in certain embodiments, the first microchannel may be provided with an alternative valve element arrangement. For example, in one embodiment, the first microchannel can be provided with a single valve element which is positioned at an intersect between the first microchannel and an intersecting channel, in place of a pair of valve elements positioned adjacent to a junction between the first microchannel and an intersecting channel. The single valve element may comprise a through channel which is sized to accommodate a volume of the sample. This volume of sample can be isolated by turning the valve element. The isolated sample portion can be then be flowed from the valve channel by way of positive pressure supplied by a driving mobile phase. This embodiment is shown in FIG. 10.

Downstream from the junction, the first intersecting channel is in fluid communication with a reagent inlet port 3260. Further downstream from the reagent inlet port 3260, the first intersecting channel comprises a serpentine mixing portion 3270. The first intersecting channel is in fluid communication with a detection zone 3280. The detection zone aptly comprises a third detection channel 3285 which extends at least partially through the thickness of the chip and provides a path length between a source and a detector.

A second intersecting channel 3170 is provided on the chip. The second intersecting channel is in fluid communication with an inlet port 3180, referred to as a third inlet port. The second intersecting channel intersects the first microchannel 3010 at a junction between the third valve element 3110 and the fourth valve element 3120. In the illustrated embodiment, the second intersecting channel has a similar structure to the first intersecting channel. The second intersecting channel is in fluid communication with a second reagent inlet port 3290 at a position downstream from the junction. The second intersecting channel comprises a serpentine mixing zone 3295 in which a portion of the sample and a reagent introduced via the second reagent inlet port can be mixed together prior to entering the detection zone.

The chip may also comprise a third intersecting channel 3190. The third intersecting channel is in fluid communication with an inlet port 3200, referred to as a fourth inlet port. The third intersecting channel intersects the first microchannel at a junction between the fourth valve element 3120 and the fifth valve element 3130. The third intersecting channel is in fluid communication with a third reagent inlet port 3300 at a position downstream from the junction. The second intersecting channel comprises a serpentine mixing zone 3305 in which a portion of the sample and a reagent introduced via the second reagent inlet port can be mixed together prior to entering the detection zone.

One or more valve elements 3310, 3320, 3330 may be provided to control flow of a fluid in the first, second and/or third intersecting channels to the detection zone. Thus, the valve elements can be used to selectively move fluid e.g. a mixture of a portion of the sample and a reagent from one but not the other intersecting channels. Thus, only one mixture of sample and reagent is directed to the detection zone and into the detection channel at a time.

The microfluidic chip may additionally comprise one or more inlet ports for introducing a solution e.g. a washing solution or a standard solution through the detection zone. These inlet ports 3350, 3360 and 3370 are aptly provided upstream to the valve elements thus enabling flow of a fluid introduced through these inlet ports to the detection zone be controlled.

The detection zone may comprise an outlet 3340 for removing fluid which has travelled along the detection channel.

In alternative embodiments, each of the first, second and third intersecting channels may be in fluid communication with a detection channel. That is to say in place of the third detection channel depicted in FIG. 9, a plurality of detection channels, each connected to a single intersecting channel, may be provided. In such embodiments, determination of a plurality of characteristics using the detection channels may take place simultaneously.

The chip may also comprise a fourth intersecting channel 3210 which intersects the first microchannel at a junction between the fifth 3130 and sixth valve elements 3140. The fourth intersecting channel 3210 is aptly in fluid communication with an inlet port 3220, referred to as a fifth inlet port, provided upstream from the junction. The fourth intersecting channel is in fluid communication with a further detection zone 3520 which comprises a second separation element 3270. The second separation element may comprise a monolithic body as described above and/or prepared as indicated below.

Preparation of Cation-Exchange Monolithic Body as a Separation Element

The desired amount of 3-mercaptopropyltrimethoxysilane is added to a solution containing 10 ml ethanol and 10 ml water, followed by the addition of a silica monolith. The mixture is refluxed overnight. The monolith comprising thiol surface groups is recovered and washed with water to remove unreacted reagents. The obtained silica monolith is oxidized by reaction with 10 ml hydrogen peroxide (30%) in 10 ml water and 10 ml methanol overnight at 60° C. The monolith is recovered and washed with water, and treated with 10 ml of 1M $H_2SO_4$. The sulfonic acid modified monolith is washed with water and dried at 60° C. overnight.

Preparation of Anion-Exchange Monolithic Body as a Separation Element

The desired amount of silica monolith is added to anhydrous toluene. To this is added a solution containing 0.12 ml methyltrichlorosilane and 0.3 m 3-chloropropyltrichlorosilane in anhydrous toluene. The reaction is conducted at 80° C. under nitrogen atmosphere for 24 hours. After this, the monolith is recovered and washed with dichloromethane, methanol, water and methanol to remove unreacted reagents and then dried at 80° C. overnight. Following this, the monolith is treated with N,N-dimethylethanamine in DMF at 80° C. for 24 hours to form positively charged groups on the surface of the silica monolith.

Preparation of Reverse Phase Silica Monolith as a Separation Element

The desired amount of silica monolith is added to a solution of 1.57 mmol octadecyltrimethoxysilane in toluene. The reaction is conducted at 80° C. overnight. The monolith is recovered and washed with toluene and dried at 60° C. overnight.

For further details on the functionalization of silica monoliths please see C. S. Gill, B. A. Price, C. W. Jones, J Catal. 2007, 251, 145 or C. R. Silva, C. Airoldi, K. E. Collins, C. H. Collins, LCGL North America 2004, 22, 632.

Preparation of Monolithic Module

Once functionalised, the monolithic body must be hermetically sealed to ensure that, when administered, fluid flows through the monolithic body and not around the monolithic body, for example at the interface between the monolithic body and housing. This process is described above.

The second separation element may be comprised in a separate module which is provided on the upper surface of the upper planar surface in use. The second separation element is in fluid communication with a microchannel 3420 which flows to a detection zone comprising an electrochemical cell 3410. The second separation element is in fluid communication with an outlet 3450 provided in a detection zone also comprising the electrochemical cell.

The chip also comprises a fifth intersecting channel 3230 which intersects the first microchannel at a junction between the sixth valve element 3140 and the seventh valve element 3145. An inlet port 3240 referred to as a sixth inlet port, is provided in fluid communication with the fifth intersecting channel upstream from the junction.

The fifth intersecting channel 3230 is in flow communication with a first separation element 3400 provided in the further detection zone 3520. The first separation element comprises a monolithic body or module as described herein.

The first separation element 3400 is in fluid communication with a further microchannel 3420 which flows into a detection zone which comprises electrochemical cell 3410. The electrochemical cell may comprise a chamber approximately 50 μm deep, 150 μm wide and 20 mm long. A working electrode is comprised in the cell. In one embodiment, the working electrode is a platinum wire (0.25 mm diameter) encased in a glass tube (3 mm diameter). The electrochemical cell also comprises a counter electrode and a reference electrode. In one embodiment, the counter electrode comprises a platinum wire having a diameter of approximately 1 mm in diameter. In one embodiment, the reference electrode comprises a silver/silver chloride wire having a diameter of approximately 1 mm. Each of the electrodes are placed by way of holes in the cell. In an alternative embodiment, the working electrode is gold, the counter electrode is platinum wire and the reference electrode is palladium wire.

The chip may further comprise an outlet 3460 downstream from the electrodes of the electrochemical cell. In an alternative embodiment, the electrochemical cell comprises a screen-printed electrode. The screen-printed electrode may be adapted from commercially available electrodes such as those available from DropSens, Spain. The screen-printed electrode may be sealed to the microchip by way of an O-ring.

In certain embodiments, the QCM also incorporates a radiation detector. The radiation detector may be for example a positron detector or a gamma detector.

Aptly the QCM may also include or be connected in use to a fibre optic cable which is positioned generally aligned with the first detection channel 3070. The fibre optic cable may be connected to a source e.g. a light source (not shown). The system further comprises a cable which is generally aligned with the first detection channel on an opposite surface to the cable. The cable 4030 is connected to a detector e.g. a miniaturised UV-visible spectrometer or a visible-near infrared spectrometer.

Similarly, a pair of cables are positioned adjacent to the third detection channel and are connected to a source and a detector respectively. A further cable is positioned adjacent to and generally aligned with the second detection channel. The further cable may be a Raman spectrometry cable. The Raman spectrometry cable may act as a connector to a Raman probe which acts as both the source and the detector.

In certain embodiments of the present invention, one or more of the channels provided in the chip have a passive mixing structure. In one embodiment, one or more channels comprise a herringbone pattern on one or more surfaces thereof.

In use, a sample comprising a radiopharmaceutical is introduced into the QCM via the sample inlet port 3020. The sample can be introduced by means known in the art e.g. a syringe pump or the like. The sample is typically in a quantity which is equivalent to or slightly greater than a single unit dose. Aptly, the sample is introduced from a purification module (PM).

In use, a sample of a compound for in vivo use e.g. a radiopharmaceutical is provided to the microfluidic chip. The sample may be provided using a number of methods including for example via a syringe, or a dropper. The sample may be pumped into the microfluidic chip. Fluid, e.g. the sample, can be flowed through microchannels e.g. by applying negative pressure to an outlet connected to the microchannels or by way of a syringe connected to a syringe pump (e.g. Pump 11 Elite, Harvard Apparatus, UK). Other methods of directing flow of a fluid in a microfluidic are known to the person skilled in the art.

The sample input may be carried out automatically or manually. The sample may be provided to the chip in a microfluidic quantity. In one embodiment, the sample is provided in a quantity which is generally equivalent to a unit dose for use in a patient. In one embodiment the sample is supplied in a quantity which is equivalent to a single unit dose once the amount of sample required to perform the quality control analytical techniques have been removed.

The sample or a portion thereof may then be directed to the first microchannel and/or the sample channel. The first valve element 3040 may be provided in a first direction to direct a portion of the sample into the sample channel for example. When the desired quantity of the sample has been directed into the sample channel, the valve direction may be changed to prevent any more of the sample from entering the sample channel.

The portion of the sample in the sample channel 3050 may then flow along the sample channel. Negative pressure applied at an outlet 3060 can be used to cause the portion of the sample to flow along the sample channel and along the first 3070 and the second detection channels 3080. The source e.g. light via a fibre optic cable may be transmitted along the long axis of the detection channel at the same time as the sample or portion thereof is accommodated in the detection channel.

A light source such as a halogen light source (HL-2000-FHSA (Ocean Optics) can be provided in the system according to certain embodiments. A detector (USB2000+VIS-NIR-ES (Ocean Optics) is provided as detailed above. Optical fibres (QP400-1-UV-VIS (Ocean Optics) can be used to connect the light source and the detector to the chip at a position which is generally aligned to the long axis of the first detection channel. In certain embodiments, the detector may be for example an infra-red detector or a fluorescence detector.

In order to determine appearance and/or clarity, absorbance values of the samples are recorded. The presence of unexpected peaks in the spectra indicates contamination of the sample.

Raman spectroscopy can be performed on a portion of the sample which flows in to the second detection channel 3080 to determine the presence and optionally the quantity of impurities e.g. ethanol and/or acetonitrile in the sample. Aptly, the Raman spectroscopy setup comprises a 785 nm continuous wave laser (Laser-785-IP-LAB, Ocean Optics, UK) coupled into a fibre optic Raman probe (RPB, InPhotonics, Ocean Optics). The probe may have a working distance of 7.5 mm and yield a laser spot size of 160 µm, with a depth of field of 1.5 mm. Scattered light from the sample can be collected via the same probe and directed by the bifurcated optical fibre into a miniaturised spectrometer (QE65000, Ocean Optics).

The Raman probe may be fixed into a custom built holder that allows the laser to be focussed by moving the probe back and forth, before turning a screw to lock it into its final position. Raman spectra and other absorption spectroscopy results may be recorded using SpectraSuite software (Ocean Optics).

The microfluidic chip is placed into an aluminium holder, orientated vertically, and was positioned via an x-y translation stage such that the Raman laser was aligned with the 368 µm diameter detection channel in the chip. The probe was then focussed into the 3 mm long channel using the holder described above.

In one embodiment, for the sample (e.g. a sample comprising [$^{18}$F]FDG) to be considered suitable for in vivo use, it must contain no more than 5000 ppm in water of ethanol and no more than 410 ppm in water of acetonitrile. Aptly, the method of certain embodiments comprises calibrating the Raman spectrometer by recording the spectra of the ethanol and acetonitrile standards and comparing the peak intensities to those of the sample. Aptly, peak intensities will be taken at approximately 882 $cm^{-1}$ for ethanol and approximately 925 $cm^{-1}$ for acetonitrile.

No reagents are added to the portion of the sample directed into the sample channel. Therefore, this portion of the sample can be collected from the outlet 3060 and administered to a patient, provided the sample meets all of the quality control requirements. Thus, in certain embodiments, the portion of the sample which is directed into the sample channel is equivalent to a unit dose of the compound.

The remainder of the sample may be directed into the first microchannel. This may occur prior to or subsequent to the portion of the sample flowing into the sample channel. The portion of the sample may be flowed into the first microchannel by way of e.g. negative pressure applied to the outlet 3600. During this stage, all of the second to seventh valves are open to allow flow of the portion of the sample along the length of the first microchannel. Aptly, the valves in the intersecting channels are closed to avoid contamination from reagents pre loaded in the detection zones.

Once the portion of the sample is situated along the first microchannel, application of negative pressure is ceased. Aptly, each of the second to seventh valves are closed so as to isolate portions of the sample between pairs of valve elements. It is then possible to carry out a different analytical technique on each isolated sample portion so as to determine multiple characteristics of the sample.

Thus, aptly, portion of the sample isolated between the second and the third valve elements can be analysed to determine pH of the sample. A driving solution is introduced into the inlet port and thus into the first intersecting channel 3150. Introduction of the driving solution forces the portion of the sample isolated between the closed valve elements into the first intersecting channel to form a plug of sample. The driving solution causes entraining of the isolated sample such that substantially all of the sample isolated between the valves enters the first intersecting channel. The sample plug is then forced along the first intersecting channel downstream from the junction of this channel and the first microchannel. It will be appreciated that the valves of the intersecting channel must be open to allow movement of the sample and solution.

A reagent is introduced via reagent inlet port 3260. If pH is being measured, a universal pH indicator can be introduced. The universal pH indicator is then mixed with the sample plug in the mixing zone of the first intersecting channel. Aptly, the universal pH indicator solution (pH 3-10) is supplied by e.g. Fluke (code: 31282), diluted with ethanol in a 1:2 ratio of indicator/ethanol. A colourimetric reaction between the sample and the universal indicator takes place which can then be analysed using UV-visible or vis-NIR spectrometry. Aptly, the reaction and detection of pH of the sample is carried out at room temperature or in a temperature controlled environment.

A light source such as a halogen light source (HL-2000-FHSA (Ocean Optics)) can be provided in the system according to certain embodiments. A detector (e.g. USB2000+VIS-NIR-ES (Ocean Optics)) is provided as detailed above. Optical fibres (QP400-1-UV-VIS (Ocean Optics)) can be used to connect the light source and the detector to the chip at the third detection channel 3340. The system may be calibrated by mixing the universal indicator with a range of pH standards or alternatively pH standards at the allowed pH values only (e.g. 4.5 and 8.5 for FDG).

The pH of the sample can be detected by analysing the spectra recorded. Further determination of the pH can be carried out by plotting either a V-shaped plot which is generated from absorbance values at a wavelength taken in the 545-550 nm range to provide a pass/fail criteria or alternatively plotting a radar plot from wavelengths of 520, 540, 560, 600, 620 and 640 nm to allow pH determination based on shape recognition.

Once the portion of the sample has flowed down the third detection channel it may be collected from the outlet and then discarded.

The third detection channel can be used as a container to carry out a number of absorbance based tests e.g. determination of pH. Other characteristics which can be determined using the absorbance based set up include for example determination of the presence and/or quantity of bacterial endotoxin in the sample. In certain embodiments, e.g. when the sample is a radiopharmaceutical such as FDG, the characteristic may be the presence and/or quantity of Kryptofix 2.2.2.

Aptly, a driving solution is introduced into the second intersecting channel via the third inlet port when the third and fourth valves are closed. The driving solution forces the portion of the sample isolated between the third and the fourth valves to form a plug and flow along the second intersecting channel. A reagent which undergoes a colourimetric reaction with the sample e.g. an iodoplatinate reagent if the characteristic to be determined is the presence/quantity of Kryptofix 2.2.2 is introduced into the second reagent inlet port 3290 and mixing of the iodoplatinate reagent and the sample plug takes place in the serpentine mixing zone of the second intersecting channel. In one embodiment, the method comprises mixing the iodoplatinate solution with the sample in a chamber provided in the fluid flow path.

In one embodiment, the iodoplatinate reagent comprises 5% w/v chloroplatinic acid, 10% w/v potassium iodide and water in a ratio of 5:45:100.

In order to calibrate the system, a standard Kryptofix 2.2.2 solution can be added to the inlet 3290 and mixed with the iodoplatinate reagent in the mixing zone and subsequently detected in the detection channel. The Kryptofix 2.2.2 standard solution may comprise Kryptofix 2.2.2 dissolved in water to a concentration which is equivalent to a standard regulations e.g. 2.2 mg/V, wherein V is the maximum recommended injectable volume of a radiotracer volume in a patient or alternatively, 50 ppm.

Aptly, the analysis is performed at either 574 nm or 590 nm wavelength. The spectra values of the mixture of the iodoplatinate reagent and the sample can then be compared against those obtained for the standard and the amount of Kryptofix 2.2.2 in the sample determined.

Aptly, the QCM can be used to determine the presence and/or quantity of bacterial endotoxin in a sample. Aptly, a driving solution is introduced into the third intersecting channel at the fourth inlet port. A plug of the sample isolated between the fourth and fifth valve elements is formed and driven into the third intersecting channel. A LAL (limulus amebocyte lysate) reagent is introduced into the reagent port 3300 and mixed with the sample. Subsequently, a chromogenic substrate may be introduced via a further reagent port (not shown). Following further incubation (see below), a "stop" reagent e.g. 25% acetic acid may be added via a further inlet port (not shown) to quench the reaction. The mixture can then be analysed using the spectrometric set up described above. The absorbance readings are aptly taken at a wavelength of between 405-410 nm. Aptly, the reaction between the LAL reagent and the sample or standard is carried out at 37+/−1° C. Thus, in certain embodiments, the chip and system comprise one or more heating elements (not shown) to heat at least a portion e.g. the mixing zone of the third intersecting channel.

An exemplary protocol for performing the bacterial endotoxin test is as follows:
1. Mix the LAL reagent and the sample e.g. in the serpentine portion of the third intersecting channel and incubate for 10 min at 37° C.;
2. A chromogenic substrate is added to the channel and incubated for 6 min at 37° C.;
3. A "stop" reagent e.g. dilute acetic acid can then be added to quench the reaction;
4. The mixture is flowed along a detection channel;
5. Measurement at 405-410 nm is taken on a spectrometer.

Prior to sample analysis, the chip and system can be calibrated by introduced a standard into the third intersecting channel and mixed with the LAL reagent. The standard may have a concentration of 175 IU/V (where IU is international units and V is the maximum recommended injectable volume of the compound e.g. a radiopharmaceutical for a patient as per the European Pharmacopoeia).

It will be appreciated that the valves 3295, 3320, 3330 are positioned to allow flow of a fluid from a single intersecting channel to the detection zone only and thus prevents flow of the fluid in the other intersecting channels to the detection zone.

In an embodiment, the chip and the system may be used to determine the chemical purity of the sample. In embodiments in which the sample comprises a radiopharmaceutical e.g. FDG, the chip and system may be used to determine the presence and/or quantity of impurities such as for example FDM and CIDG. These impurities may be detected following separation of components in the sample using a strong anion exchange (SAX) stationary phase column which may be a monolithic body or a packed particle bed. Aptly, the mobile phase comprises sodium hydroxide.

A mobile phase can be provided to the fourth intersecting channel 3210 via inlet port 3220. A plug of a portion of the sample isolated in the first microchannel between the fifth and sixth valve elements is formed and forced into the fourth intersecting channel in a direction towards the separation element.

A radiation detector can then be used to determine the presence and/or quantity of these impurities. The radiation detector may be a gamma detector or a positron detector.

The SAX column can be used to separate the components of the sample. In embodiments in which the compound is FDG, impurities such as FDM, D-mannose, D-glucose and CIDG are separated on the column. The sample is then flowed through the electrochemical cell. Pulsed amperometric detection can then be carried out. In alternative embodiments, spectrometric or refractive index detection could be used in place of PAD detection.

PAD uses a triple-step potential waveform to combine amperometric detection followed by alternating anodic and cathodic polarizations to clean and reactivate the working electrode surface. Thus, a three-potential waveform is used. The waveform consists of a pulse containing three different voltages applied to the working electrode. The first voltage is used for measuring, the second voltage is for cleaning the working electrode after the measurement and the third voltage is for regenerating the working electrode. The waveform is continuously repeated to achieve detection of the impurities. A potentiostat such as PalmSens3 available from PalmSens, the Netherlands can be used to control the electrodes and voltages and measure the detection signals.

The fifth intersecting channel 3230 can be provided with a mobile phase introduced via the sixth inlet port 3240. Providing the sixth and seventh valves are in a closed position, the driving solution forces a plug of sample isolated between the valves to form and flow along the fifth intersecting channel towards a second separation element. The mobile phase may be for example a solution composed of acetonitrile:water in a ratio 90:10 or 95:10. In certain embodiments, e.g. if the separation element comprised C18-functionalised silica, the mobile phase may be a solution composed of acetronitrile:water in a ratio of between about 40:60 to about 60:40 e.g. 50:50.

The second separation element e.g. a silica monolithic column or a C18-functionalised monolithic column can be used to separate components of the sample. In the exemplified embodiment in which the compound is FDG, the second separation element can be used to separate components such as fluoride-18, FDG and acetylated-FDG within the sample. A radiation detector can then be used to determine the presence and/or quantity of these components in the sample.

It will be understood that analysis of the sample in the first, second and third detection channels may be carried out simultaneously or sequentially.

Figure 12:
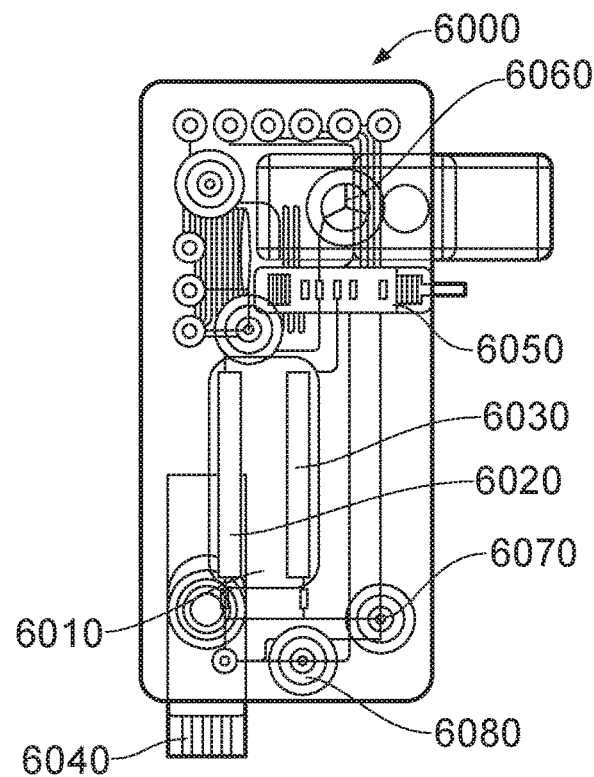
FIG. 12 illustrates a microfluidic chip comprising a Quality Control Module of certain embodiments of the present invention.
Figure 13:
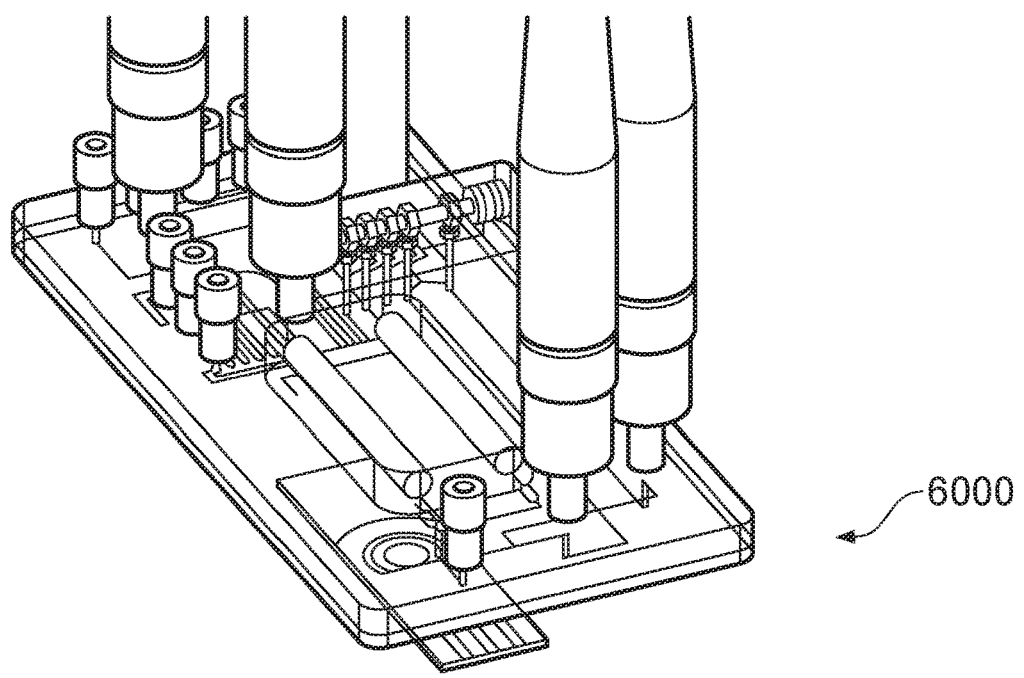
FIG. 13 illustrates a microfluidic chip comprising a Quality Control Module of certain embodiments of the present invention.

FIGS. 12 and 13 illustrate a chip 6000 according to certain embodiments of the invention. The chip comprises a separable component 6010 which comprises two monolithic bodies 6020 and 6030 as described herein. The chip also incorporates an electrochemical cell 6040 which in the illustrated embodiment is a screen printed electrode. The electrode may be slid into a recess in the chip.

The chip also comprises a Raman chamber 6060. A pin valve membrane 6050 is provided to control flow of a sample to the Raman chamber. The chip comprises a plurality of inlets and outlets as described herein. Furthermore, the chip is provided with a plurality of detection channels. Fibres, for example, the fibres 6070 and 6080 are positioned adjacent to an end of a respective detection channel for spectroscopic analysis of a solution, e.g. a portion of a sample, which is provided in the detection channel.

Figure 14:
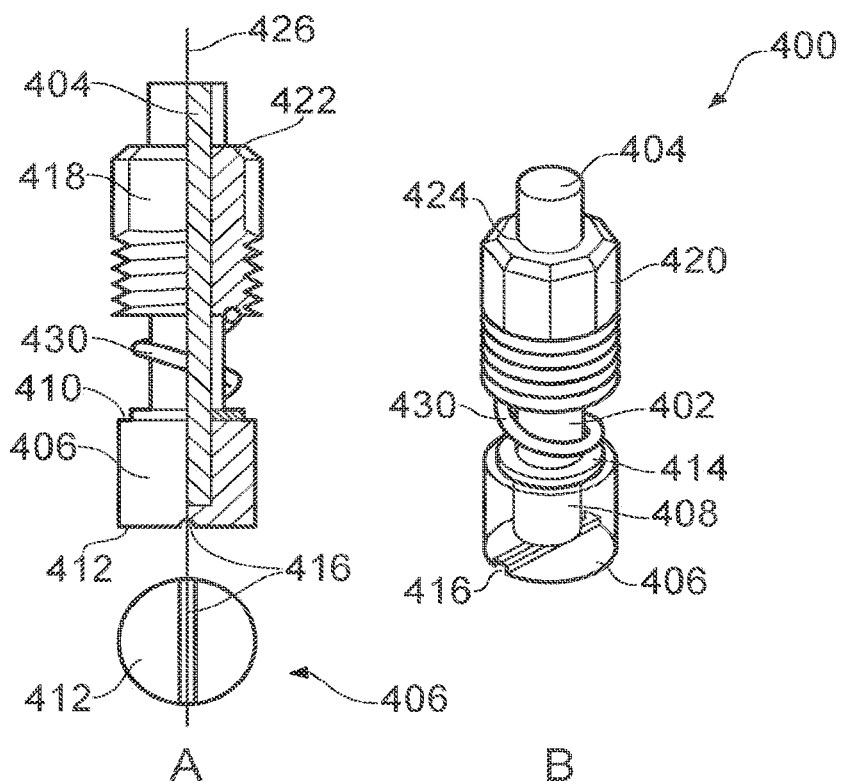
FIG. 14 illustrates a valve assembly for inclusion in a system according to certain embodiments of the present invention.
Figure 15:
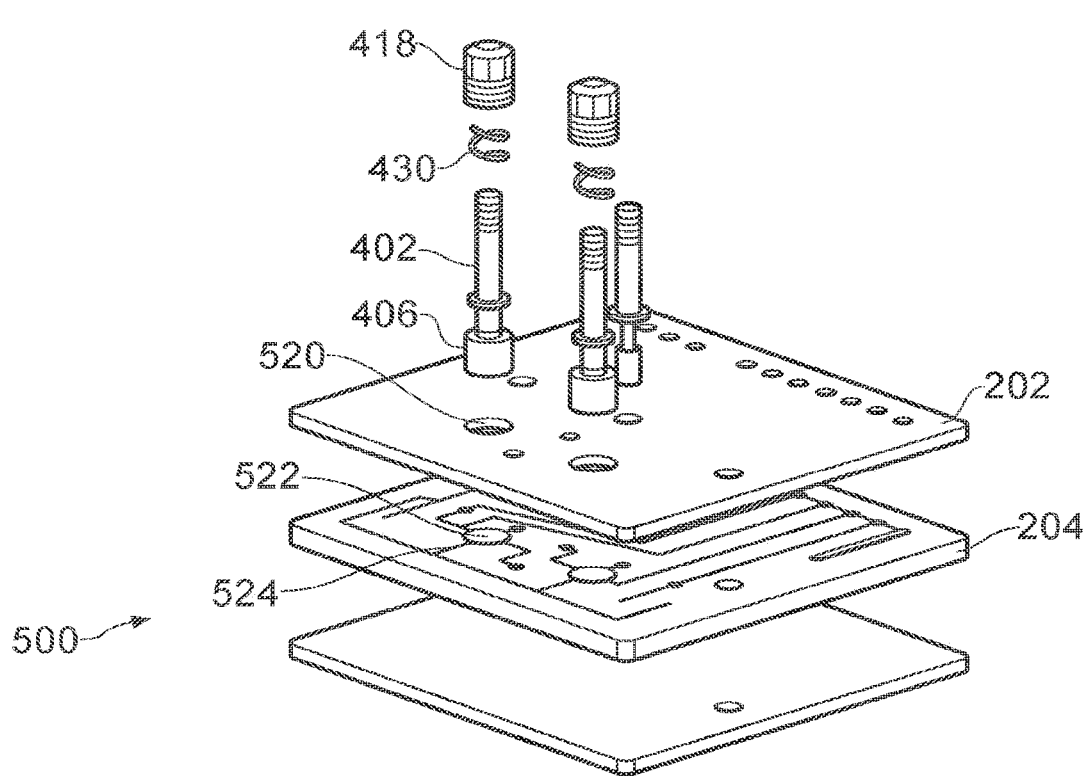
FIG. 15 is a schematic representation of a QCM comprising a valve assembly according to certain embodiments of the present invention.

In certain embodiments, the QCM and/or the RIM and/or the RPM may comprise one or more valve assemblies. FIG. 14 and FIG. 15 illustrate an embodiment of a valve element for use in directing and controlling fluid flow within and between modules described herein. Thus, FIG. 14 shows a valve assembly 400 according to certain embodiments of the present invention for a microfluidic chip includes a valve shaft 402 having a splined upper end region 404 and a valve head 406 attached to a lower end region 408. The valve head 406 has a substantially flat upper surface 410 and a substantially flat lower surface 412. The lower end region 408 of the valve shaft 402 is located in a central bore that extends downwardly into the valve head 406 from the upper surface 410 of the valve head 406. The upper surface 410 of the valve head abuts with a lower surface of an annular shoulder 414 of the valve shaft 402. The valve head 406 may be attached to the valve shaft 402 by adhesive, a mechanical fastener, friction fit, or corresponding screw threads, or the like.

A through conduit 416 in the form of a channel is disposed in the lower surface 412 of the valve head 406. Alternatively, the through conduit 416 may not be disposed in the lower surface 412 of the valve head 406 and may be a through hole disposed between the upper and lower surfaces 410, 412 of the valve head 406.

The valve assembly 400 includes a cap-like valve housing 418 having an annular wall portion 420 and an upper portion 422. The upper portion 422 has a centrally located aperture 424 for slidably receiving the valve shaft 402 such that the valve housing 418 can be slid on to the upper end region 404 and along a portion of the valve shaft 402. The central aperture 424 is substantially circular and the valve shaft 402 is substantially cylindrical such that it is rotatable about a valve axis 426 when located in a microfluidic chip whilst also being translatable in a direction along the valve axis 426 with respect to the valve housing 418.

The annular wall portion 420 of the valve housing 418 includes a screw thread 428 that corresponds to a screw thread in an upper layer of the microfluidic chip (as described hereinbelow). The annular wall portion 420 further includes a plurality of flat surfaces for engagement with a tool for driving the valve housing 418 and securing the same in the upper layer of the microfluidic chip. One end of a compression spring 430 sits on an upper surface of the annular shoulder 414 of the valve shaft 402 and the other end of the compression spring 430 abuts an inner surface of the upper portion 422 of the valve housing 418. The compression spring 430 biases the valve head 406 away from the valve housing 418. Aptly, the spring may sit directly on the shoulder which is formed from silicone or it could sit indirectly using washers between. Alternatively, the main shaft may comprise a shoulder To install the valve assembly 400 (e.g. a plug type valve assembly) in a microfluidic chip 500 according to certain embodiments of the present invention, as illustrated for example in FIG. 32, the valve head 406 is located through a correspondingly shaped and sized aperture 520 in an upper layer 502 of the microfluidic chip 500 to engage with a recessed valve seat surface 522 disposed in an intermediate layer 504 of the microfluidic chip 500. The compression spring 430 is placed over the upper end region 404 of the valve shaft 402 to sit on the annular shoulder 414 thereof. The valve housing 418 is then placed over the upper end region 404 of the valve shaft 402 and the screw thread 428 thereof is brought into engagement with a corresponding screw thread (not shown) surrounding the aperture 520 in the upper layer 502 of the microfluidic chip 500. A suitable tool, such as a hex spanner, is used to drive and securely attach the valve housing 418 to the upper layer 502 of the microfluidic chip 500. In turn, the compression spring 430 is compressed between the annular shoulder 414 and the valve housing 418 such that the spring 430 biases the valve head 406 against the valve seat surface 522. In certain embodiments, the valve could be fully assembled separately and later be inserted to the microfluidic device assembled layers.

In use, a suitable actuator, such as a stepper motor (not shown), is coupled to the upper splined end region 404 of the valve shaft 402 to selectively rotate the valve head 406, and in particular the through conduit 416, between an open position and a closed position relative to one or more fluid flow channels 524 disposed in the intermediate layer 504 of the microfluidic chip 500. This provides for selective delivery of at least a portion of a fluid sample from an input region of the microfluidic chip 500 towards a detection zone of the microfluidic chip 500.

The splined upper end region 404 of the valve shaft 402 further allows the valve shaft 402 to translate in a direction along the valve axis 426 with respect to the actuator that selectively rotates the valve shaft 402. The compression spring 430 is selected such that a spring force thereof corresponds to a maximum threshold pressure of fluid in at least an upstream portion of the fluid flow channels 524 relative to the valve assembly 400. When the fluid pressure exceeds the maximum threshold pressure, and thus a fluid force acting on the valve head 406 exceeds the spring force of the compression spring 430, the valve head 406 and valve shaft 402 are forced upwardly to place the valve in an open configuration and to allow upstream fluid to flow past the valve and towards an outlet channel for the excessive pressure to be safely relieved and damage to the microfluidic chip 500 to be minimised if not prevented. Aptly, the valve assembly 400 may include an adjuster (not shown) to allow a length of the compression spring 430 to be adjusted and thus in turn allow the spring force to be set as desired in accordance with a predetermined maximum threshold fluid pressure.

The valve head 406 is made of a substantially resilient material such as a biomedical grade elastomer. Aptly, the biomedical grade elastomer may be a silicone rubber e.g. medical grade silicone. Such a material improves the sealing engagement between the valve head 406 and the valve seat surface 522 and is suitable for use with fluids for medical applications. Furthermore, it is easily moulded, making it suitable for fabricating a variety of shapes and being medical-grade, there should be very little in the way of contamination of a dose caused by impurities leaching out of the material. The valve shaft 402 and valve housing 418 are made of a metal material, such as brass or aluminium or the like, or alternatively may be made from a relatively hard polymer material, such as nylon or PTFE or the like.

In certain embodiments, the channel in the lower surface of the valve head enables an amount of a sample to be collected. Rotation of the valve may then cause the valve to be disconnected from the microchannel e.g. a sample input channel and connected to a further channel e.g. a channel which is connected to an inlet for a mobile phase. Consequently, a plug of the sample will be injected out from the head of valve having mobile phase liquid behind it. In other words, the dimensions of the channel in the valve would determine the volume of sample contained in the valve, which could be filled with sample and then be isolate by turning the valve, allowing the known volume to be directed into a new channel.

In certain embodiments, the microfluidic chip does not comprise a detection channel as described herein. For example, in embodiments in which the chip is for use to carry out non-spectrometric techniques, the chip does not need to comprise the detection channel. Thus, in certain embodiments of the present invention, the microfluidic chip may comprise for example a plurality of valve elements as described herein which can be used to isolate portions of a fluid e.g. a sample or mixture comprising a sample, wherein the isolated portions of fluid are directed to a zone on the microfluidic chip where a non-spectrometric analytical technique is performed. An example of a non-spectrometric analytical technique comprises the use of the electrochemical detection cell as described herein. A further example of a non-spectrometric analytical technique is radiation detection using the radiation detector and separation elements described herein.

The system of certain embodiments of the present invention may further comprise computer hardware and software. The computer hardware and software may be used to determine the one or more characteristics or parameters measured on the microfluidic chip. In addition, the computer system may report results of tests carried out on the microfluidic chip. Such results may be reported as for example a simple "Pass/Fail". Alternatively, the results may be reported as a total numeric score which if it falls under or over a certain value can be considered as a "Fail" and therefore unsuitable for administration to a patient.

In certain embodiments, the system may further comprise one or more elements to calibrate and control the components of the system.

Aptly, each of the modular components are in fluid communication e.g. by way of a conduit or conduits or by way of one or more microchannels provided in a microfluidic device. The modules may be provided as separate components which may be fixed to a microfluidic chip prior to use. The system may be a fully automated system.

Systems

Figure 2:
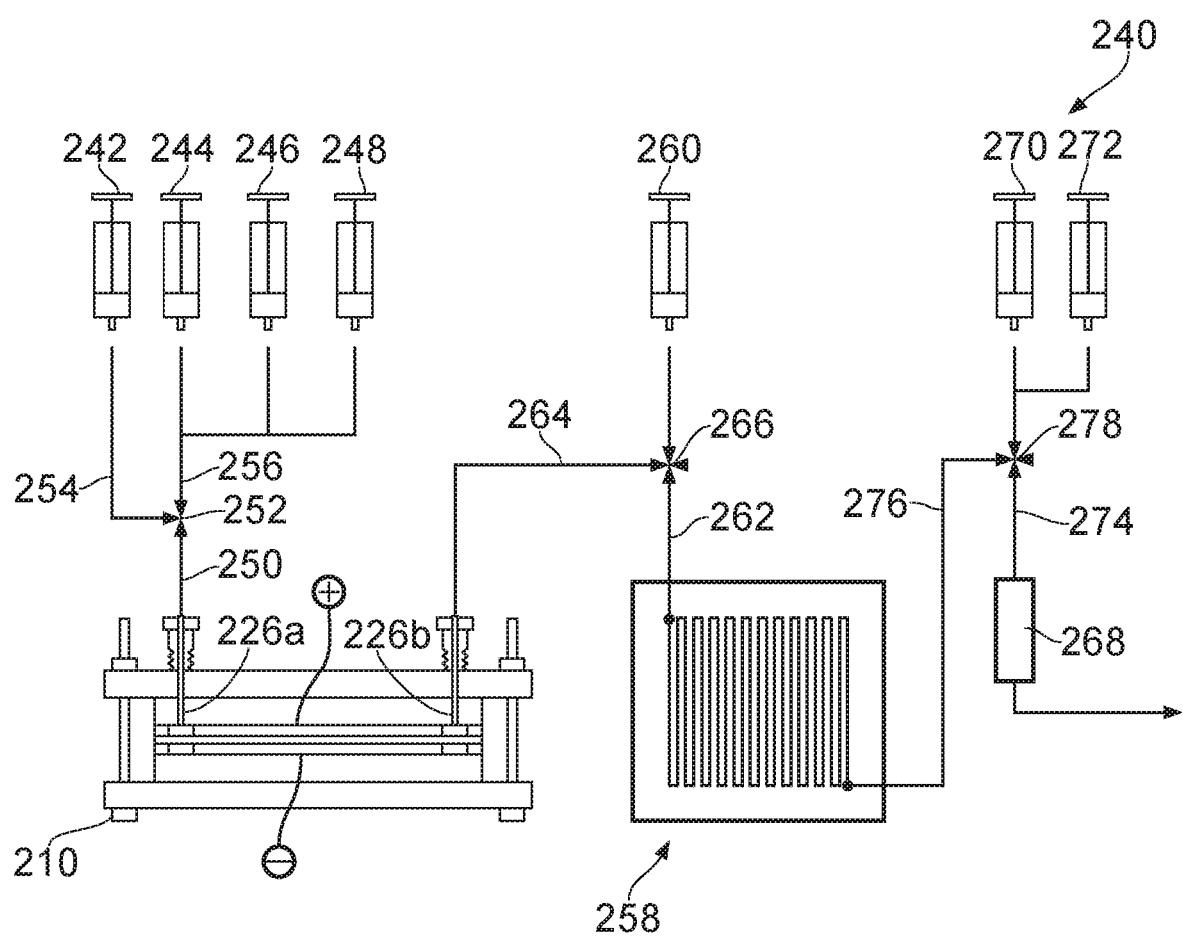
FIG. 2 is a schematic representation of the system of certain embodiments of the present invention.

FIG. 2 shows a microfluidic system 240 for the preparation of a radiotracer. In the embodiment shown, the system is set up for the synthesis of [$^{18}$F]-FDG, but it will be appreciated that the system could be used to prepare any desired radiopharmaceutical. The system eliminates evaporation steps for solvent exchange, and enables dose-on-demand production of radiotracers in an integrated system.

The system 240 comprises the microfluidic cell 210 for solvent exchange of $^{18}$F by electro-trapping and release. The microfluidic cell 210 is supplied with fluids from a set of four syringes, a first syringe 242 containing a source of $^{18}$F, a second syringe 244 containing acetonitrile for washing, a third syringe 246 containing an organic-based solvent and a fourth syringe 248 containing water. A line 250 connects the syringes 242, 244, 246, 248 to the inlet 226a of the microfluidic cell 210. The flow of fluids into the cell 210 is controlled by a first valve 252 positioned at a point at which the line 250 diverges between a first branch 254 leading to the first syringe 242 and a second branch 256 leading to the second 244, third 246 and fourth 248 syringes.

The system further comprises a microfluidic reactor 258 and a fifth syringe 260, which contains mannose triflate. A flow path 262 connects the fifth syringe 260 to the microfluidic reactor 258. A line 264 feeds fluids from the outlet 226b of the microfluidic cell 210 into the flow path 262. A second valve 266 is positioned at the junction of the line 264 with the flow path 262, and controls the flow of fluids into the microfluidic reactor 258.

The system additionally comprises a 018 deprotection column 268 (monolith), a sixth syringe 270 containing water for elution and a seventh syringe 272 containing sodium hydroxide for hydrolysis. A flow path 274 supplies fluids from the sixth and seventh syringes 270, 272 to the deprotection column 268. A line 276 feeds fluids from the microfluidic reactor 258 into the flow path 274. A third valve 278 is positioned at the junction of the line 276 with the flow path 274, and thus controls the flow of fluids into the deprotection column 268.

Recovery of $^{18}$F from an aqueous solution into an organic-based solution by electro trapping and release is carried out using the microfluidic cell 210, as described above. The organic-based solution containing the released $^{18}$F ions leaves the microfluidic cell 210 via the outlet 226b, and is transferred to the microfluidic reactor 258 via the line 264. Mannose triflate is supplied to the microfluidic reactor 258 from the fifth syringe 260 via the flow path 262. Within the microfluidic reactor 258 the mannose triflate undergoes a nucleophilic substitution reaction with the $^{18}$F ions, producing acetylated [$^{18}$F]-FDG. The acetylated [$^{18}$F]-FDG is then transferred to the deprotection column 268 via line 276 and flow path 274, where it undergoes hydrolysis in the presence of a sodium hydroxide solution to produce [$^{18}$F]-FDG.

Figure 3:
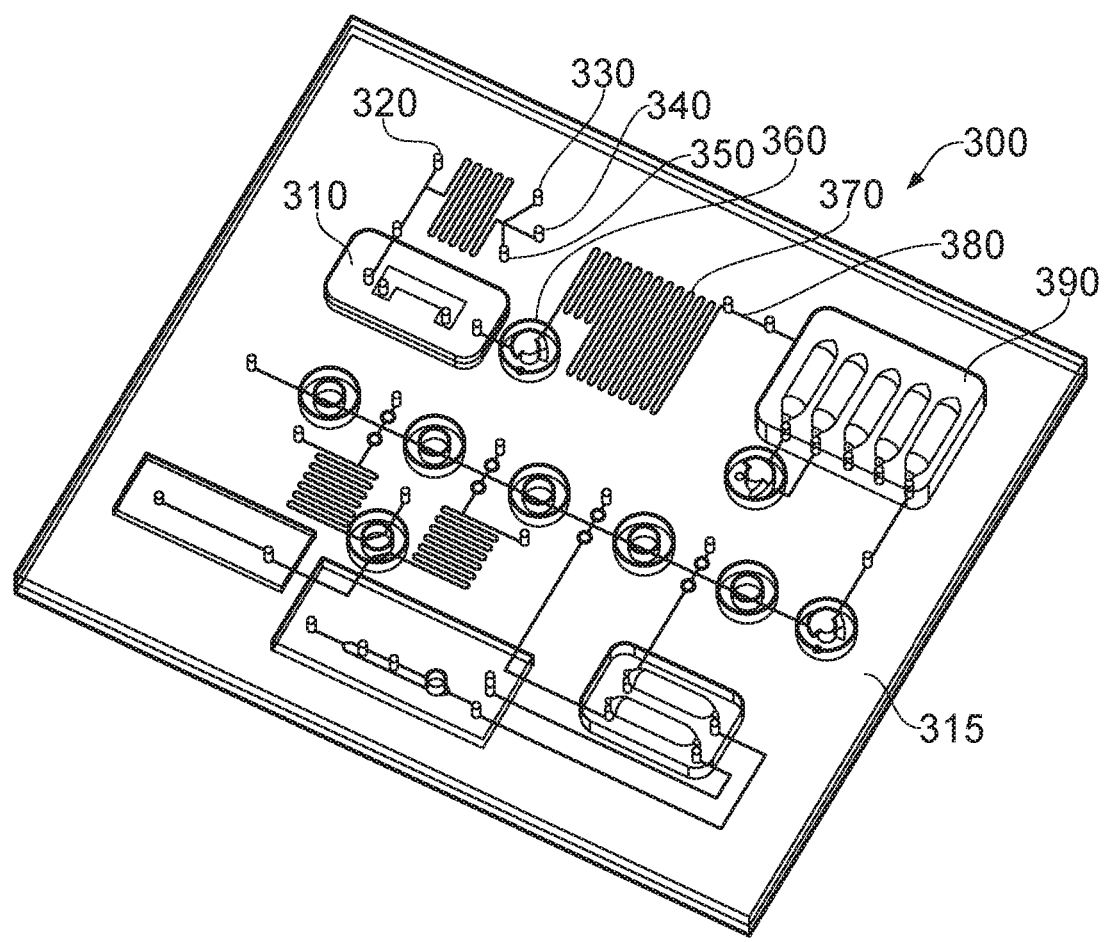
FIG. 3 illustrates an integrated microfluidic system of certain embodiments of the present invention.

FIG. 3 illustrates an integrated system 300 for producing a microfluidic quantity of a radiopharmaceutical. The system comprises a RIM 310 which comprises an electrode trapping cell as described herein. The RIM may be in fluid communication with one or more inlets 320, 330, 340, 350 for introducing an aqueous solution comprising a radioactive isotope and one or more reagents and/or solvents. The one or more reagents include for example mannose triflate in acetonitrile, Kryptofix 2.2.2 and potassium carbonate in acetonitrile and water, and acetonitrile.

The RIM is connected via a microchannel 360 to a RPM which in the illustrated embodiment comprises a serpentine mixing channel 370. The RPM is connected via a further microchannel 380 to a PM 390. The PM may comprise a plurality of monolithic bodies composed in a module as described herein. The PM may be in fluid communication with one or more inlets to provide a solvent or other mobile phase. The inlet holes may be to introduce for example water and sodium hydroxide.

The PM is connected to a QCM 315 which comprises one or more detection zones. Further details of exemplary QCM are provided herein.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A microfluidic system for the production of a radiopharmaceutical composition comprising:
   a Radioisotope Isolation Module (RIM) configured to receive an aqueous solution comprising a radioisotope;
   a Radiopharmaceutical Production Module (RPM) configured to receive a first sample which comprises a concentrated and activated radioisotope from the RIM;
   a Purification Module (PM) configured to receive a second sample which comprises a radiopharmaceutical and one or more further components from the RPM; and
   a Quality Control Module (QCM), configured to receive a third sample from the PM which comprises a purified radiopharmaceutical and which is further configured to determine one or more characteristics of the third sample;
   wherein:
   the RIM, RPM, PM and QCM are provided as an integrated system on a single microfluidic chip;
   the RIM, RPM, PM and QCM are each independently a microfluidic component of the integrated system having at least one channel for fluid flow of less than 500 µm; and
   the PM and the QCM each independently comprise a chromatographic inorganic monolithic body that is a cation exchange, anion exchange, normal phase, or reverse phase monolithic body comprising functionalized silica.

2. The system of claim 1, which is configured to produce per run a single (one) unit dose of the radiopharmaceutical composition.

3. The system of claim 1, wherein the system has a total volume capacity of less than about 800 µL.

4. The system of claim 1, wherein the RIM comprises an apparatus for separating and recovering a radioactive isotope from an aqueous solution comprising the radioactive isotope, the apparatus comprising:
   an inlet;
   an outlet; and
   a chamber in fluid communication with the inlet and the outlet to form a fluid pathway, the chamber comprising a first electrode and a second electrode,
   wherein the first electrode is a carbon disk formed from a carbon rod;
   wherein the chamber has a volume capacity of no greater than about 50 µL; and wherein the distance between the first electrode and the second electrode is no greater than 0.5 mm.

5. The system of claim 4, wherein the apparatus is configured to receive fluid at a flow rate of at least 0.1 ml/min.

6. The system of claim 4, wherein the RIM is a microfluidic cell.

7. The system of claim 1, wherein the RIM comprises a monolithic body configured to separate the radioisotope from the aqueous solution, and optionally, the RIM's monolithic body is a strong anionic exchange monolith.

8. The system of claim 7, wherein the PM's chromatographic monolithic body is configured to separate one or more impurities from the radiopharmaceutical.

9. The system of claim 1, wherein the radioisotope is [$^{18}$F]fluoride or $^{68}$Ga or a cation thereof.

10. The system of claim 1, further comprising one or more inlets in fluid communication with the RIM for introducing a radiopharmaceutical precursor or protected form thereof.

11. The system of claim 1, wherein the Purification Module (PM) is configured to receive the second sample and separate the radiopharmaceutical from the one or more further components.

12. The system of claim 1, wherein the QCM comprises a microfluidic chip for determining at least one characteristic of the third sample, the microfluidic chip comprising:
a length (Ll), a width (Wl) and a thickness (Tl) wherein Tl<Wl and Tl<Ll; a supply component for introducing the sample into the chip;
a fluid flow path in fluid communication with the supply component; and
a detection channel in the fluid flow path;
wherein the detection channel extends at least partially through the thickness (Tl) of the microfluidic chip and wherein the detection channel is configured to provide both a fluid flow path and a path length along a long axis thereof.

13. The system of claim 12, wherein in use the detection channel provides an optical path length between a detector and a source, such that absorbance of a fluid in the detection channel may be determined.

14. The system of claim 12, wherein the detection channel is axially aligned with a light source and a detector when in use and is enclosed within the microfluidic chip, and optionally the chip further comprises one or more valve elements for directing and/or controlling fluid flow in the fluid flow path.

15. The system of claim 12, wherein at least a portion of the chip comprises a material which is capable of optical transmission.

16. The system of claim 12, wherein the detection channel comprises an upper opening and a lower opening, each contained within the chip, and wherein the detection channel is configured to permit flow of a fluid along a long axis thereof.

17. The system of claim 12, wherein the microfluidic chip comprises a plurality of detection channels.

18. The system of claim 12, wherein the QCM microfluidic chip further comprises:
at least two detection zones, each detection zone comprising a component for performing an analytical technique; and
a plurality of isolation valve elements provided in the fluid flow path to control and/or direct fluid flow in the fluid flow path;
wherein each isolation valve element is movable from an open position to a closed position such that a portion of the third sample is isolated for direction to a detection zone.

19. The system of claim 18, wherein:
the fluid flow path comprises a first microchannel which comprises a plurality of isolation valve elements,
the chip further comprises at least one further microchannel, and
each further microchannel is in fluid communication with a different portion of the first microchannel provided between a pair of isolation valve elements.

20. The system of claim 18, wherein each detection zone comprises one or more components selected from:
an electrochemical cell;
a radiation detector;
a separation element; and
a detection channel.

21. The system of claim 12, wherein the QCM is configured to determine:
pH of the sample;
clarity of the sample;
the presence and/or concentration of bacterial endotoxin in the sample;
the presence and/or concentration of an impurity in the sample; and
optionally the radiation level of the sample.

22. The system of claim 1, wherein the modules are in fluid communication by way of a microfluidic flow path.

23. The system of claim 1, further comprising:
a source; and
a detector.

24. The system of claim 23, wherein:
the source is a light source; and the detector is a spectrometer selected from a visible-near infrared spectrometer, a UV-visible light spectrometer and a Raman spectrometer.

25. The system of claim 23, wherein the source and the detector, and optionally one or more connecting element(s), are aligned such they are orthogonal to a chip of the QCM and aligned with a long axis of the detection channel such that a detection channel provides a path length between the source and the detector.

26. A method of producing a radiopharmaceutical composition comprising:
a) supplying an aqueous solution comprising a radioisotope to a Radioisotope Isolation Module (RIM) and forming a first sample comprising a concentrated and activated radioisotope;
b) supplying the first sample from the RIM to a Radiopharmaceutical Production Module (RPM);
c) supplying a second sample which comprises a radiopharmaceutical or an intermediate and optionally one or more further components to a Purification Module (PM) configured to receive the second sample from the RPM;
d) supplying a third sample which comprises a purified radiopharmaceutical from the PM to a Quality Control Module (QCM); and
e) performing at least one analytical technique on the third sample or a portion thereof to determine at least one characteristic of the third sample;
wherein:
the RIM, RPM, PM and QCM are provided as an integrated system on a single microfluidic chip;
the RIM, RPM, PM and QCM are each independently a microfluidic component of the integrated system having at least one channel for fluid flow of less than 500 µm; and
the PM and QCM each independently comprise a chromatographic inorganic monolithic body that is a cation exchange, anion exchange, normal phase, or reverse phase monolithic body comprising functionalized silica.

27. The method of claim 26, wherein:
i) the RIM further comprises a chromatographic monolithic body and step (a) comprises supplying the aqueous solution to the RIM's chromatographic monolithic body and eluting the aqueous solution through the RIM's chromatographic monolithic body, wherein the RIM's monolithic body is an inorganic monolithic body and is part of a microfluidic flow system; or,
ii) the RIM comprises a microfluidic cell comprising a chamber, the chamber comprising a first electrode and a second electrode, and step (a) comprises:
flowing the aqueous solution to the RIM, generating a first electric field between the first and second electrodes, thereby trapping the radioisotope on the first electrode,
flowing an organic-based solution to the chamber, and
generating a second electric field between the first and the second electrodes, wherein the second electric field has an opposing polarity to the first electric field, thereby releasing the radioisotope from the first electrode into the organic based solution,
wherein the first electrode is formed from a carbon rod or section thereof.

28. The method of claim 26, wherein step (b) further comprises reacting the radioisotope of the first sample with a precursor or protected form thereof to provide the second sample.

29. The method of claim 26, wherein step (c) is carried out on the PM's chromatographic inorganic monolithic body, and optionally comprises:
separating the radiopharmaceutical from an impurity selected from [$^{18}$F]fluoride and endotoxin to form the third sample, using a normal phase monolithic body;
separating the radiopharmaceutical from an impurity selected from acetylated FDG, mannose triflate and Kryptofix 222 to form the third sample, using a reverse phase monolithic body;
separating the radiopharmaceutical from an impurity selected from Kryptofix 222 and sodium hydroxide to form the third sample, using a cation exchange monolithic body; or
separating the radiopharmaceutical from a hydrochloric acid impurity to form the third sample, using an anion exchange monolithic body.

30. The method of claim 26 wherein step (d) comprises performing an analytical technique on the third sample on a detection zone, the analytical technique selected from:
determining pH of the third sample;
determining the presence and/or a concentration of an impurity in the third sample;
determining the concentration of bacterial endotoxin in the third sample;
determining the clarity and/or appearance of the third sample or a portion thereof; and
combinations of any of the foregoing.

31. The method of claim 30, further comprising:
performing a spectroscopic technique on the third sample or a portion thereof or a mixture comprising the third sample or a portion thereof, by positioning a light source and a detector such that a detection zone is provided between the light source and the detector that provides a path length for light emitted by the light source to be transmitted to the detector, and performing the spectroscopic technique.

* * * * *